(12) United States Patent
Vachon et al.

(10) Patent No.: US 8,586,094 B2
(45) Date of Patent: *Nov. 19, 2013

(54) COATED TABLETS

(75) Inventors: Michael Vachon, Montreal (CA);
Mishra K. Awadesh, Montreal (CA);
Robert A. Snow, Westchester, PA (US);
Pol-Henri Guivarc'H, Montreal (CA)

(73) Assignee: Jagotec AG, Muttenz (CH)

(*) Notice: Subject to any disclaimer, the term of this patent is extended or adjusted under 35 U.S.C. 154(b) by 1278 days.

This patent is subject to a terminal disclaimer.

(21) Appl. No.: 10/428,007

(22) Filed: May 2, 2003

(65) Prior Publication Data
US 2004/0091535 A1      May 13, 2004

Related U.S. Application Data

(63) Continuation-in-part of application No. 09/838,541, filed on Apr. 20, 2001, now abandoned.

(60) Provisional application No. 60/377,237, filed on May 3, 2002, provisional application No. 60/234,186, filed on Sep. 20, 2000, provisional application No. 60/241,761, filed on Oct. 20, 2000.

(51) Int. Cl.
*A61K 9/16* (2006.01)
*A61K 9/20* (2006.01)
*A61K 9/48* (2006.01)
*A61K 9/50* (2006.01)

(52) U.S. Cl.
USPC ........... 424/490; 424/489; 424/456; 424/457; 424/464; 424/468; 424/493; 424/494; 424/495; 424/496; 424/497; 424/498

(58) Field of Classification Search
None
See application file for complete search history.

(56) References Cited

U.S. PATENT DOCUMENTS 2,803,582 A    8/1957 Cherney
3,137,631 A    6/1964 Soloway
(Continued)

FOREIGN PATENT DOCUMENTS

CA    2 048 395    2/1992
DE    2 519 797    10/1975
(Continued)

OTHER PUBLICATIONS

La Fuma Polymery 1998 43 nr 2, 104-108 The role of water-soluble polymers at the solid/liquid etc.

(Continued)

*Primary Examiner* — Lakshmi Channavajjala
(74) *Attorney, Agent, or Firm* — Muriel Liberto, Esq.; Mintz Levin Cohn Ferris Glovsky and Popeo, P.C.

(57) ABSTRACT

Disclosed is a pharmaceutically acceptable oral dosage form comprising fenofibrate, phospholipid, a buffer salt, a water-soluble bulking agent selected from maltodextrin, mannitol, and combinations thereof, a cellulosic additive, beads or crystals of a pharmaceutically acceptable water-soluble excipient support material, a polyvinylpyrrolidone or crospovidone, croscarmellose sodium, granular mannitol, sodium dodecyl sulfate, silicon dioxide, and a stearate, wherein the fenofibrate is in the form of microparticles, and wherein at least a portion of the phospholipid is coated on the surfaces of the fenofibrate microparticles, the phospholipid coated microparticles are embedded in a matrix comprising the water-soluble bulking agent, phospholipid that is not coated on the microparticles, the buffer salt and the cellulosic additive, and the matrix is coated on up to 100% of the surfaces of the beads or crystals of the excipient support material.

27 Claims, 3 Drawing Sheets

(A) fenofibrate    (B) Micronized fenofibrate    (C) Microfluidized fenofibrate

Optical microscopic comparison of microfluidized fenofibrate with micronized fenofibrate and fenofibrate

(56) References Cited

U.S. PATENT DOCUMENTS

| | | | |
|---|---|---|---|
| 3,216,897 A | 11/1965 | Krantz | |
| 3,274,063 A | 9/1966 | Nieper et al. | |
| 3,594,476 A | 7/1971 | Merrill | |
| 3,715,432 A | 2/1973 | Merrill | |
| 3,755,557 A | 8/1973 | Jacobs | |
| 3,794,476 A | 2/1974 | Michalik et al. | |
| 3,937,668 A | 2/1976 | Zolle | |
| 3,960,757 A | 6/1976 | Morishita et al. | |
| 3,965,255 A | 6/1976 | Bloch et al. | |
| 3,983,140 A | 9/1976 | Endo et al. | |
| 4,006,025 A | 2/1977 | Swank et al. | |
| 4,016,100 A | 4/1977 | Suzuki et al. | |
| 4,053,585 A | 10/1977 | Allison et al. | |
| 4,056,635 A | 11/1977 | Glen et al. | |
| 4,073,943 A | 2/1978 | Wretlind et al. | |
| 4,078,052 A | 3/1978 | Papahadjopoulos | |
| 4,089,801 A | 5/1978 | Schneider | |
| 4,102,806 A | 7/1978 | Kondo et al. | |
| 4,107,288 A | 8/1978 | Oppenheim et al. | |
| 4,133,874 A | 1/1979 | Miller et al. | |
| 4,145,410 A | 3/1979 | Sears | |
| 4,147,767 A | 4/1979 | Yapel, Jr. | |
| 4,186,183 A | 1/1980 | Steck et al. | |
| 4,219,548 A | 8/1980 | Reller | |
| 4,231,938 A | 11/1980 | Monaghan et al. | |
| 4,235,871 A | 11/1980 | Papahadjopoulos et al. | |
| 4,241,046 A | 12/1980 | Papahadjopoulos et al. | |
| 4,271,196 A | 6/1981 | Schmidt | |
| 4,280,996 A | 7/1981 | Okamoto et al. | |
| 4,294,916 A | 10/1981 | Postle et al. | |
| 4,298,594 A | 11/1981 | Sears et al. | |
| 4,302,459 A | 11/1981 | Steck et al. | |
| 4,308,166 A | 12/1981 | Marchetti et al. | |
| 4,309,421 A | 1/1982 | Ghyczy et al. | |
| 4,316,884 A | 2/1982 | Alam et al. | |
| 4,320,121 A | 3/1982 | Sears | |
| 4,325,871 A | 4/1982 | Sasaki et al. | |
| 4,328,222 A | 5/1982 | Schmidt | |
| 4,329,332 A | 5/1982 | Couvreur et al. | |
| 4,331,654 A | 5/1982 | Morris | |
| 4,332,795 A | 6/1982 | Ghyczy et al. | |
| 4,332,796 A | 6/1982 | Los | |
| 4,340,594 A | 7/1982 | Mizushima et al. | |
| 4,345,588 A | 8/1982 | Widder et al. | |
| 4,346,227 A | 8/1982 | Terahara et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,378,354 A | 3/1983 | Ghyczy et al. | |
| 4,394,372 A | 7/1983 | Taylor | |
| 4,397,846 A | 8/1983 | Weiner et al. | |
| 4,411,894 A | 10/1983 | Schrank et al. | |
| 4,411,933 A | 10/1983 | Samejima et al. | |
| 4,421,747 A | 12/1983 | Ghyczy et al. | |
| 4,427,649 A | 1/1984 | Dingle et al. | |
| 4,448,765 A | 5/1984 | Ash et al. | |
| 4,448,784 A | 5/1984 | Glamkowski et al. | |
| 4,450,171 A | 5/1984 | Hoffman et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,529,561 A | 7/1985 | Hunt et al. | |
| 4,532,089 A | 7/1985 | MacDonald | |
| 4,610,868 A | 9/1986 | Fountain et al. | |
| 4,613,505 A | 9/1986 | Mizushima et al. | |
| 4,622,219 A | 11/1986 | Haynes | |
| 4,675,236 A | 6/1987 | Ohkawara et al. | |
| 4,687,762 A | 8/1987 | Fukushima et al. | |
| 4,725,442 A | 2/1988 | Haynes | |
| 4,727,077 A | 2/1988 | Haga et al. | |
| 4,739,073 A | 4/1988 | Kathawala | |
| 4,756,910 A | 7/1988 | Yagi et al. | |
| 4,761,288 A | 8/1988 | Mezei | |
| 4,762,720 A | 8/1988 | Jizomoto | |
| 4,766,046 A | 8/1988 | Abra et al. | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,837,028 A | 6/1989 | Allen | |
| 4,839,111 A | 6/1989 | Huang | |
| 4,880,634 A | 11/1989 | Speiser | |
| 4,895,726 A * | 1/1990 | Curtet et al. | 424/456 |
| 4,897,402 A | 1/1990 | Duggan et al. | |
| 4,904,646 A | 2/1990 | Karanewsky et al. | |
| 4,906,624 A | 3/1990 | Chucholowski et al. | |
| 4,906,657 A | 3/1990 | Roth | |
| 4,920,109 A | 4/1990 | Onishi et al. | |
| 4,923,861 A | 5/1990 | Picard et al. | |
| 4,929,620 A | 5/1990 | Chucholowski et al. | |
| 4,939,143 A | 7/1990 | Regan et al. | |
| 4,940,727 A | 7/1990 | Inamine et al. | |
| 4,940,800 A | 7/1990 | Bertolini et al. | |
| 4,946,860 A | 8/1990 | Morris et al. | |
| 4,946,864 A | 8/1990 | Prugh et al. | |
| 4,950,675 A | 8/1990 | Chucholowski | |
| 4,957,940 A | 9/1990 | Roth | |
| 4,961,890 A | 10/1990 | Boyer | |
| 4,963,367 A | 10/1990 | Ecanow | |
| 4,963,538 A | 10/1990 | Duggan et al. | |
| 4,968,693 A | 11/1990 | Joshua et al. | |
| 4,970,231 A | 11/1990 | Lee et al. | |
| 4,973,465 A | 11/1990 | Baurain et al. | |
| 4,990,337 A | 2/1991 | Kurihara et al. | |
| 4,992,429 A | 2/1991 | Ullrich et al. | |
| 4,994,494 A | 2/1991 | Regan et al. | |
| 4,996,234 A | 2/1991 | Regan et al. | |
| 4,997,837 A | 3/1991 | Chucholowski et al. | |
| 5,001,128 A | 3/1991 | Neuenschwander et al. | |
| 5,001,144 A | 3/1991 | Regan et al. | |
| 5,017,716 A | 5/1991 | Karanewsky et al. | |
| 5,021,453 A | 6/1991 | Joshua et al. | |
| 5,025,000 A | 6/1991 | Karanewsky | |
| 5,030,453 A | 7/1991 | Lenk et al. | |
| 5,081,136 A | 1/1992 | Bertolini et al. | |
| 5,091,187 A | 2/1992 | Haynes | |
| 5,091,188 A | 2/1992 | Haynes | |
| 5,091,378 A | 2/1992 | Karanewsky et al. | |
| 5,091,386 A | 2/1992 | Kesseler et al. | |
| 5,098,931 A | 3/1992 | Duggan et al. | |
| 5,100,591 A | 3/1992 | Leclef et al. | |
| 5,102,911 A | 4/1992 | Lee et al. | |
| 5,112,857 A | 5/1992 | Vickers | |
| 5,116,870 A | 5/1992 | Smith et al. | |
| 5,130,306 A | 7/1992 | Duggan et al. | |
| 5,132,312 A | 7/1992 | Regan et al. | |
| 5,135,935 A | 8/1992 | Alberts et al. | |
| 5,145,684 A | 9/1992 | Liversidge et al. | |
| 5,166,171 A | 11/1992 | Jendralla et al. | |
| 5,179,079 A | 1/1993 | Hansen et al. | |
| 5,182,298 A | 1/1993 | Helms et al. | |
| 5,196,440 A | 3/1993 | Bertolini et al. | |
| 5,202,327 A | 4/1993 | Robl | |
| 5,217,707 A | 6/1993 | Szabó et al. | |
| 5,246,707 A | 9/1993 | Haynes | |
| 5,250,435 A | 10/1993 | Cover et al. | |
| 5,256,689 A | 10/1993 | Chiang | |
| 5,260,332 A | 11/1993 | Dufresne | |
| 5,262,435 A | 11/1993 | Joshua et al. | |
| 5,273,995 A | 12/1993 | Roth | |
| 5,276,021 A | 1/1994 | Karanewsky et al. | |
| 5,283,256 A | 2/1994 | Dufresne et al. | |
| 5,286,895 A | 2/1994 | Harris et al. | |
| 5,298,262 A | 3/1994 | Na et al. | |
| 5,302,401 A | 4/1994 | Liversidge et al. | |
| 5,302,604 A | 4/1994 | Byrne et al. | |
| 5,317,031 A | 5/1994 | MacConnell et al. | |
| 5,326,552 A | 7/1994 | Na et al. | |
| 5,336,507 A | 8/1994 | Na et al. | |
| 5,340,564 A | 8/1994 | Illig et al. | |
| 5,356,896 A | 10/1994 | Kabadi et al. | |

(56) References Cited

U.S. PATENT DOCUMENTS

| | | | |
|---|---|---|---|
| 5,364,633 A | 11/1994 | Hill et al. | |
| 5,369,125 A | 11/1994 | Berger et al. | |
| 5,385,932 A | 1/1995 | Vickers | |
| 5,389,377 A | 2/1995 | Chagnon et al. | |
| 5,447,710 A | 9/1995 | Na et al. | |
| 5,470,583 A | 11/1995 | Na et al. | |
| 5,510,118 A | 4/1996 | Bosch et al. | |
| 5,527,537 A | 6/1996 | Dietl | |
| 5,545,628 A | 8/1996 | Deboeck et al. | |
| RE35,338 E | 9/1996 | Haynes | |
| 5,569,448 A | 10/1996 | Wong et al. | |
| 5,576,016 A | 11/1996 | Amselem et al. | |
| 5,589,455 A | 12/1996 | Woo | |
| 5,603,951 A | 2/1997 | Woo | |
| 5,622,985 A | 4/1997 | Olukotun et al. | |
| 5,637,625 A | 6/1997 | Haynes | |
| 5,639,474 A | 6/1997 | Woo | |
| 5,645,856 A | 7/1997 | Lacy et al. | |
| 5,662,932 A | 9/1997 | Amselem et al. | |
| 5,700,471 A | 12/1997 | End et al. | |
| 5,776,495 A | 7/1998 | Duclos et al. | |
| 5,778,495 A | 7/1998 | Paugh | |
| 5,785,976 A | 7/1998 | Westesen et al. | |
| 5,827,536 A | 10/1998 | Laruelle | |
| 5,851,275 A | 12/1998 | Amidon et al. | |
| 5,858,410 A | 1/1999 | Muller et al. | |
| 5,880,148 A | 3/1999 | Edgar et al. | |
| 5,922,355 A | 7/1999 | Parikh et al. | |
| 5,976,577 A * | 11/1999 | Green et al. | 424/490 |
| RE36,520 E | 1/2000 | Smith et al. | |
| 6,027,747 A | 2/2000 | Terracol et al. | |
| 6,042,847 A | 3/2000 | Kerč et al. | |
| 6,068,854 A | 5/2000 | Wunderlich et al. | |
| 6,074,670 A * | 6/2000 | Stamm et al. | 424/462 |
| 6,096,338 A | 8/2000 | Lacy et al. | |
| 6,180,138 B1 | 1/2001 | Engh et al. | |
| 6,228,399 B1 | 5/2001 | Parikh et al. | |
| 6,368,628 B1 | 4/2002 | Seth | 424/480 |
| 6,475,510 B1 * | 11/2002 | Venkatesh et al. | 424/441 |
| 6,696,084 B2 * | 2/2004 | Pace et al. | 424/451 |
| 2002/0003179 A1 | 1/2002 | Verhoff et al. | |
| 2002/0012675 A1 * | 1/2002 | Jain et al. | 424/400 |
| 2002/0012704 A1 | 1/2002 | Pace et al. | |
| 2002/0013271 A1 | 1/2002 | Parikh et al. | |
| 2002/0119199 A1 | 8/2002 | Parikh | |
| 2002/0161032 A1 | 10/2002 | Guivarc'h et al. | |

FOREIGN PATENT DOCUMENTS

| | | |
|---|---|---|
| DE | 2 938 807 | 11/1980 |
| DE | 3 421 468 | 12/1985 |
| EP | 052 322 | 5/1982 |
| EP | 114 027 | 7/1984 |
| EP | 272 091 | 6/1988 |
| EP | 304 063 | 2/1989 |
| EP | 330 532 | 8/1989 |
| EP | 391 369 | 10/1990 |
| EP | 418 153 | 3/1991 |
| EP | 455 042 A1 | 11/1991 |
| EP | 456 670 | 11/1991 |
| EP | 456 764 | 11/1991 |
| EP | 475 148 A1 | 3/1992 |
| EP | 0 499 299 A2 | 8/1992 |
| EP | 499 299 | 8/1992 |
| EP | 570 829 | 11/1993 |
| EP | 601 618 | 6/1994 |
| EP | 602 700 | 6/1994 |
| EP | 687 172 | 12/1995 |
| EP | 0 580 690 B1 | 3/1996 |
| EP | 724 877 | 8/1996 |
| EP | 757 911 | 2/1997 |
| EP | 807 431 | 4/1997 |
| EP | 793 958 A2 | 9/1997 |
| EP | 904 781 | 3/1999 |
| FR | 2 617 047 | 12/1988 |
| FR | 2 819 720 | 1/2001 |
| FR | 2 819 720 A1 | 7/2002 |
| GB | 2 046 094 | 11/1980 |
| GB | 2 250 197 | 6/1992 |
| HU | 211 580 B | 6/1995 |
| JP | 55 141 407 | 11/1980 |
| JP | 56 167 616 | 12/1981 |
| JP | 60 208 910 | 10/1985 |
| JP | 63 502 117 | 8/1988 |
| JP | 63 233 915 | 9/1988 |
| JP | 1 502 590 | 9/1989 |
| WO | WO 85/00011 | 1/1985 |
| WO | WO 87/04592 | 8/1987 |
| WO | WO 91/04011 | 4/1991 |
| WO | WO 94/20072 | 9/1994 |
| WO | WO 96/21439 | 7/1996 |
| WO | WO 96/24332 | 8/1996 |
| WO | WO 97/13503 | 4/1997 |
| WO | WO 97/14407 | 4/1997 |
| WO | WO 98/07414 | 2/1998 |
| WO | WO 98/31361 | 7/1998 |
| WO | WO 98/35666 | 8/1998 |
| WO | WO 99/04761 | 2/1999 |
| WO | WO 99/39700 | 8/1999 |
| WO | WO 99/65469 | 12/1999 |
| WO | WO 00/16749 | 3/2000 |
| WO | WO 00/30616 | 6/2000 |
| WO | WO 00/30616 A1 * | 6/2000 |
| WO | WO 00/37057 | 6/2000 |
| WO | WO 00/37078 | 6/2000 |
| WO | WO 00/40220 | 7/2000 |
| WO | WO 00/45817 | 8/2000 |
| WO | WO 01/80828 A2 | 1/2001 |
| WO | WO 01/30372 | 5/2001 |
| WO | WO 02/24169 A1 | 3/2002 |
| WO | WO 02/24193 A1 | 3/2002 |
| WO | WO 02/067901 A1 | 9/2002 |

OTHER PUBLICATIONS

Luckham Pestic. Sci., 1989, 25,25-34 The Physical Stability of Suspension Concentrates with Particular etc.

Calvor et al Pharm. Dev. Tech., 3(3), 297-305, 1998 Production of Microparticles by High Pressure etc.

Siekmann et al Pharm. Pharmacol Lett (1994) 3: 225-228Melt-homogenized solid lipid nanoparticles etc.

Lourenco et al Int. J. Pharm. 138 (1996), 1-12 Steric stabilization of nanoparticles: size and surface properties.

Napper Polymeric Stabilizations of Colloidal Dispersions 1983.

Müller et al Emulsions and Nanosuspensions Chapter 9 1998 p. 163.

Guzman et al 1088 J. Pharm Sci 82 (1993 No. 5 pp. 498-502 "Formation and Characterization of Cyclosporine-Loaded Nanoparticles".

Bangham et al., "Diffusion of Univalent Ions Across the Lamellae of Swollen Phospholipids," J. Mol. Biol., 1965, 13:238-251.

Benz et al., "Electrical Capacity of Black Lipid Films and of Lipid Bilayers made from Monolayers," Biochimica et Biophysica Acta, 1975, 394:323-334.

Bergmann, Ludwig, Der Ultraschall, 5 Aufl., 1949, Struttgart, pp. 551-564 and 665-677.

Bittman, Robert, "Sterol-Polyene Antibiotic Complexation: Probe of Membrane Structure," LIPIDS, vol. 13, No. 10, pp. 686-691 (1978).

Cherney, Leonid S., "Tetracaine Hydroiodide: A Long-Lasting Local Anesthetic Agent for the Relief of Postoperative Pain," Anesthesia and Analgesia, vol. 42, No. 4, Jul.-Aug. 1963, pp. 477-481.

Cudd et al., "Liposomes Injected Intravenously into Mice Associate with Liver Mitochondria," Biochimica et Biophysica Acta, (1984), 774:169-180.

Farnier et al., "Effect of Combined Fluvastatin-Fenofibrate Therapy Compared with Fenofibrate Monoth6rapy in Severe Primary Hypercholesterolemia," the Amer. J. of Cardiology, vol. 85, Jan. 1, 2000, pp. 53-57.

Fleischer et al., "Drug, Meal & Formulation Interactions Influencing Drug Absorption After Oral Adminstration," Clin. Pharmacokinetic, Mar. 1999, :36(3), pp. 233-264.

(56) References Cited

OTHER PUBLICATIONS

Goodman & Gillman's The Pharmacological Basis of Therapeutics, 7th Ed., MacMillan Publishing Co., New York, 1985. p. 312.

Gregoriadis, Gregory, "The Carrier Potential of Liposomes in Biology and Medicine", The New England Journal of Medicine, Sep. 23, 1976, vol. 295, pp. 704-710.

Haynes et al., "Ultra-Long Duration Local Anesthesia Produced by Intra-Dermal Injection of Lecithin-Coated Methoxyflurane Microdroplets", Proceed. Intern. Symp. Control. Rel. Bioact. Mater., (1987), 14:293-294 (Extended abstract).

Haynes et al., "Ultra-long-duration Local Anesthesia Produced by Injection of Lecithin-coated Methoxyfluorene Microdroplets", Anesthesiology, Nov. 1985, vol. 63, No. 5, pp. 490-499.

Haynes, Duncan H., "Divalent Cation-Ligand Interactions of Phospholipid Membranes: Equilibria and Kinetics," Metal-Ligand Interactions in Organic Chemistry and Biochemistry, Pullman and Goldblum, Eds., part 2, © 1977, pp. 189-212.

Huang et al., "Interaction of the N-terminus of Sterol Carrier Protein 2 with Membranes: Role of Membrne Curvature," Biochem. J., (1999), 344:593-603.

Kayikcioglu et al., "Effectiveness and Safety of Alternate-Day Simvastatin and Fenofibrate on Mixed Hyperlipidemia," Excerpta Medica, Inc., © 1999, pp. 1135-1137.

Kirkpatrick et al., "Local Anesthetic Efficacy of Methoxyflurane Microdroplets in Man," Anesthesiology, 1987, 67(3A):A254, Abstract only.

Lehninger Biochemistry, The Molecular Basis of Cell Structure and Function 1970 Chapter 10.

Pan et al., "Lack of a Clinically Significant Pharmacokinetic Interaction between Fenofibrate and Pravastatin in Healthy Volunteers," J. Clin Pharmacol, 2000, 40:316-323.

Rompp, "Emulsion", Chemie-Lexikon, 2 Aufl., Bd. 1, 1950, Stichwort.

Ross, et al., "Aqueous Solutions of Surface-Active Solutes", Colloidal Systems and Interfaces, © 1988, p. 148-151.

Sande et al., "Antimicrobial Agents: Antifungal and Antiviral Agents," p. 1219-1222, 1985.

Sheu, M.T. et al., "Characterization and dissolution of fenofibrate solid dispersion systems", Int. J. Pharm., 1994, 103(2), pp. 137-146.

Weil et al., "The Metabolism and Disposition of 14C-Fenofibrate in Human Volunteers," The Amer. Society for Pharm. and Experimental Therapeutics, vol. 18, No. 1, pp. 115-120, 1990.

Wu et al., "Pharmacokinetics of Methoxyflurane after its Intra-dermal Injection as Lecithin-Coated Microparticles", Journal of Controlled Release, 1989, vol. 9, pp. 1-12.

* cited by examiner

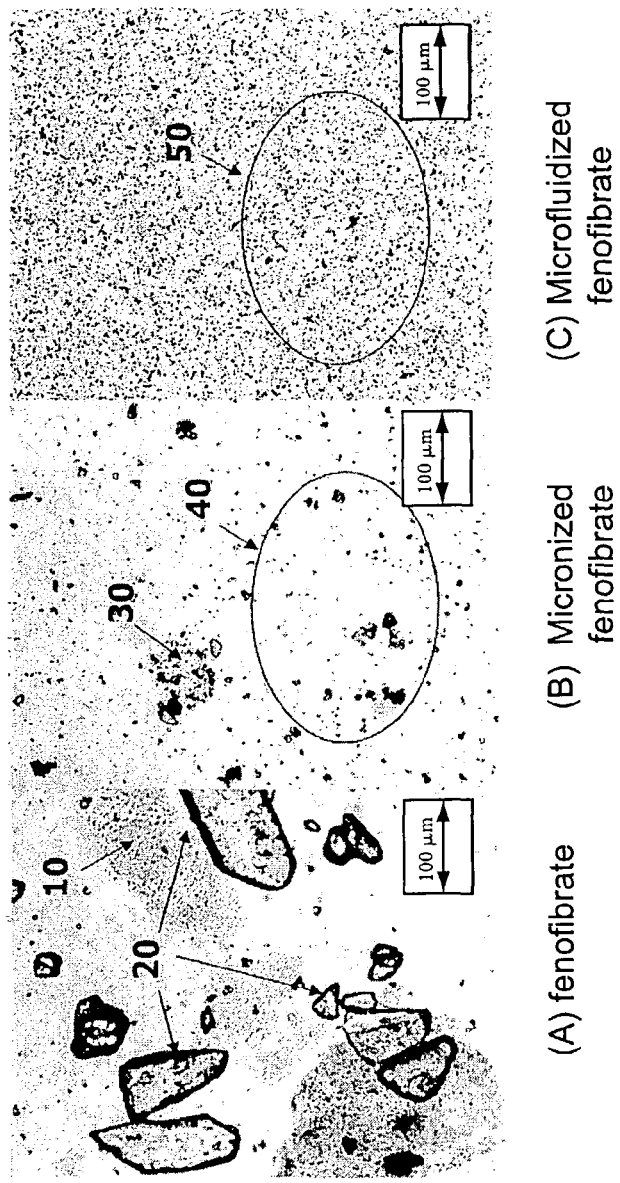
Fig. 1 Optical microscopic comparison of microfluidized fenofibrate with micronized fenofibrate and fenofibrate

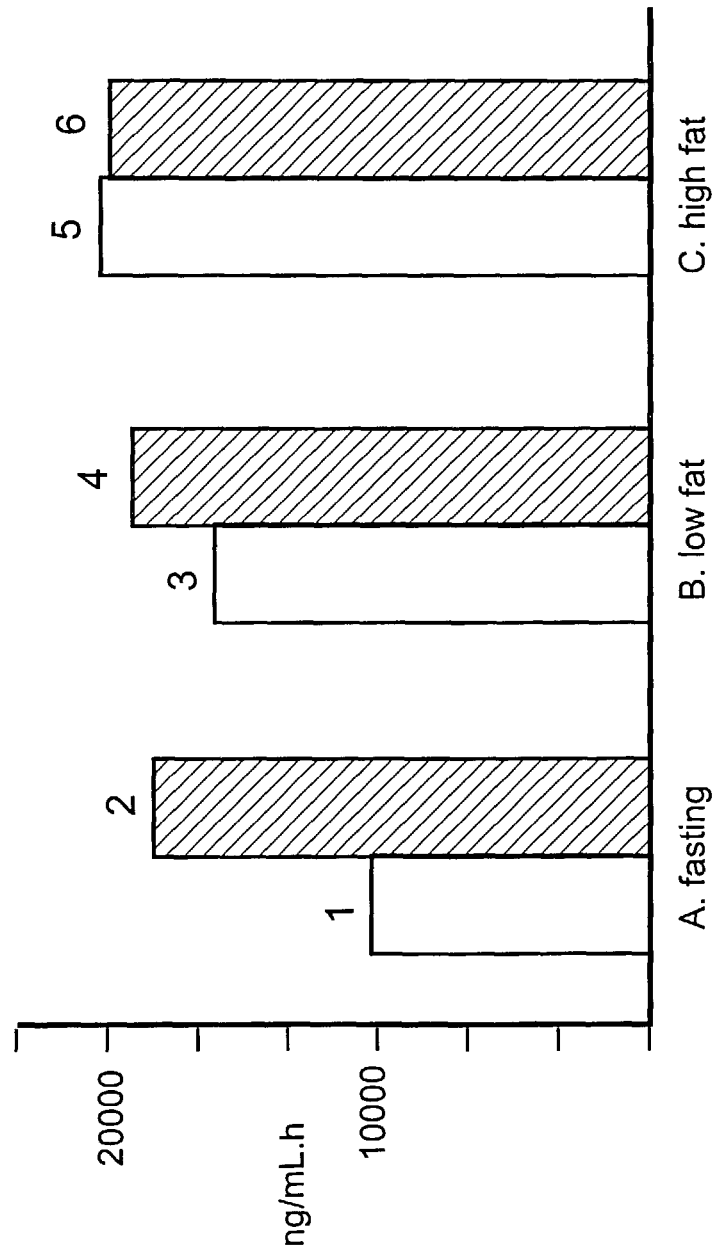
Fig.2 Comparison of oral bioavailability of phospholipid stabilized microparticles of fenofibrate versus micronized fenofibrate in fasted, low fat fed, and high fat fed conditions.

Fig.3A Fenofibric acid Mean Concentration - (Time profile; n=24)
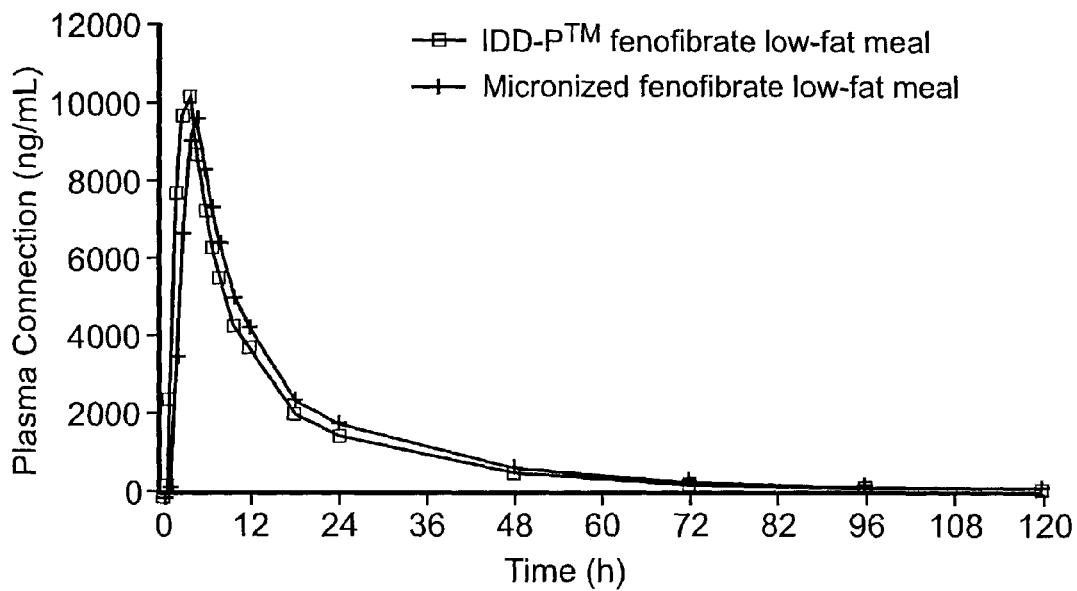
Fig.3B Fenofibric acid (Mean Concentration) - (Time profile; n=24)
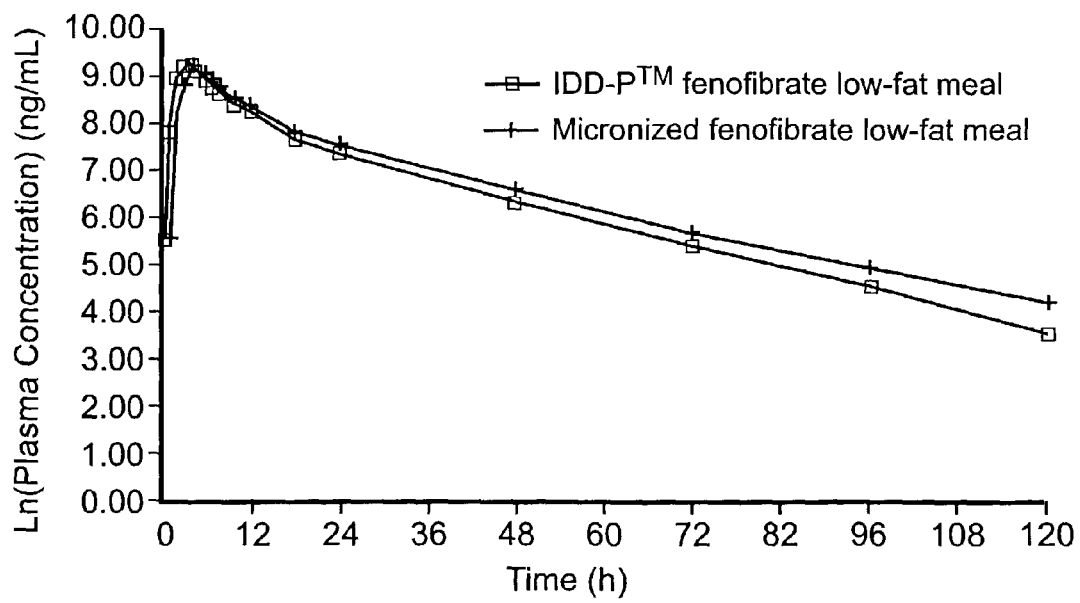

COATED TABLETS

CROSS-REFERENCE TO RELATED APPLICATIONS

This is a continuation-in-part of U.S. patent application Ser. No. 09/838,541, filed Apr. 20, 2001, and claims the benefit of U.S. provisional patent application No. 60/377,237, filed May 3, 2002. The Ser. No. 09/838,541 application claims the benefit of U.S. provisional application Nos. 60/234,186, filed Sep. 20, 2000 and 60/241,761, filed Oct. 20, 2000. The disclosures of the foregoing related applications are incorporated by reference.

FIELD OF THE INVENTION

The present invention relates to a method of treating dislipidemia and dislipoproteinemia in a mammal which comprises administering to the mammal a therapeutically effective oral dosage form comprising microparticles of a solid poorly water-soluble fibrate that are stabilized by a phospholipid surface active substance, wherein the dosage form provides into the blood of the mammal in a fasted state a therapeutically effective amount of the fibrate active species that is at least 90% of the AUC (area under the curve) amount of the fibrate active species provided by the dosage form into the blood of the patient in a fed state.

In a preferred aspect, the present invention relates to a method of treating dislipidemia and dislipoproteinemia in a human patient which comprises administering to the patient a therapeutically effective oral dosage form, particularly a tablet dosage form, comprising microparticles of fenofibrate that are stabilized by a phospholipid surface active substance, the particles suspended as a solid suspension in a matrix of rapidly dissolving and/or rapidly dispersing matrix-forming agent, especially a carbohydrate material such as a mixture of sorbitol and sucrose, which agent or combination of agents can be in an amorphous morphological state or a partially amorphous morphological state and a partially crystalline state or a crystalline state, the solid suspension of microparticles in the matrix-forming agent preferably obtained by freeze drying without substantial increase in particle size of primary particles an aqueous suspension of the primary particles of solid drug such as fenofibrate, the particles of size volume weighted mean particle size distribution of from about 0.1 microns to about 10 microns (preferably from about 0.2 microns to about 5 microns, more preferably from about 0.2 microns to about 3 microns, even more preferably from about 0.2 microns to about 2 microns, and most preferably from about 0.2 microns to about 1.5 microns) stabilized by one or more surface modifier of which at least one is a phospholipid, preferably a natural phospholipid such as egg phospholipid, the particles suspended in an aqueous medium in the presence of the matrix-forming agent or a combination of matrix forming agents, and wherein after freeze-drying of the aqueous suspension to a solid suspension of primary particles suspended in a solid matrix of matrix-forming agents, the suspension is then coarse milling and blended with a pharmaceutically acceptable excipient or a mixture of pharmaceutically acceptable excipients such as silica, a stearate salt such as magnesium stearate, additional bulking agents such as sucrose and maltodextrose to form a powder, which powder is then compressed into a tablet to form a moisture-sensitive tablet, which moisture-sensitive tablet is then coated with a protective coating barrier-layer of a pharmaceutically acceptable polymer, which coating prevents or substantially retards a change in tablet ingredient morphology such as a change from amorphous sugar morphology in which the primary particles are suspended to crystalline sugar morphology in which the primary particles are suspended and/or which coating prevents or substantially retards the rate of particle size increase in the primary particles which can occur with or without a simultaneous change in ingredient morphology, wherein the dosage form provides into the blood of the mammal in a fasted state a therapeutically effective amount of the fenofibrate active species that is at least 90% of the AUC amount of the fenofibrate active species provided by the dosage form into the blood of the patient in a fed state.

The present invention also relates to novel pharmaceutical compositions containing small particles of phospholipid-stabilized fibrates that provide reduced in vivo variability in the bioavailability of the drug active species among fed and fasted patients when administered orally. In particular, the present invention relates to an orally administered pharmaceutical composition comprising microparticles of solid fibrate, especially fenofibrate, that are prepared in the presence of and stabilized by a phospholipid surface active substance, wherein a therapeutically effective amount of the composition provides a quantity of fibrate active species to a human patient in need of treatment by the fibrate that is independent of the amount of food taken by the patient.

In a preferred aspect, the present invention relates to an orally administered pharmaceutical composition comprising microparticles of solid fenofibrate that are prepared in the presence of and stabilized by a phospholipid surface active substance, wherein a therapeutically effective amount of the composition provides a quantity of fenofibrate to a fasted human patient in need of treatment by fenofibrate that is greater than 80% of the quantity of fenofibrate provided by the same amount to the same patient when the patient is fed at least 1000 calories 50% of which are from fat.

BACKGROUND OF THE INVENTION

It has long been known that the bioavailability of many hydrophobic drugs can be improved if the drugs are administered with food, i.e., the drugs uptake into the blood or other part of the body exhibit a food effect. A patient is often instructed to take the drug at meal times or with food. Various explanations of the food effect have been advanced including: delayed gastric emptying to allow more drug to dissolve before reaching the small intestine thereby producing longer residence times at specific absorption sites in the small intestine; direct interaction and solubilization of drug by food, especially by hydrophobic food components such as fats and lipids; food-related increases in hepatic blood flow to cause a decrease in first-pass metabolism; and increased gastrointestinal secretions that can improve drug solubility.

Dosage forms or quantities of compositions containing a fibrate such as fenofibrate have been marketed and prescribed for the treatment of dislipidemia and dislipoproteinemia. Dislipidemia and dislipoproteinemia are herein defined to include the group selected from hypercholesterolemia, abnormal and elevated levels of cholesterol, abnormal and elevated levels of LDL cholesterol, abnormal and elevated levels of total cholesterol, abnormal and elevated levels of plasma cholesterol, abnormal and elevated levels of triglycerides, hypertrigylceridaemia, abnormal levels of lipoproteins, abnormal and elevated levels of low density lipoproteins (LDLs), abnormal and elevated levels of very low density lipoproteins, abnormal and elevated levels of very low intermediate density lipoproteins, abnormal levels of high density lipoproteins, hyperlipidemia, hyperchylomicronemia, abnormal levels of chylomicrons, related disorders, and combinations thereof such as those described in The ILIB Lipid Handbook for Clinical Practice, Blood Lipids and Coronary Heart Disease, Second Edition, A. M. Gotto et al, International Lipid Information Bureau, New York, N.Y., 2000, which is hereby incorporated by reference.

Elevation of serum cholesterol, triglyercides, or both is characteristic of hyperlipidemias. Differentiation of specific abnormalities usually requires identification of specific lipoprotein fractions in the serum of a patient. Lipoproteins transport serum lipids and can be identified by their density and electrophoretic mobility. Chylomicrons are among the largest and least dense of the lipoproteins. Others, in order of increasing density and decreasing size include very low density lipoproteins (VLDL or pre-beta), intermediate low density lipoproteins (ILDL or broad-beta), low density lipoproteins (LDL or beta), and high density lipoproteins (HDL or alpha). Triglycerides are transported primarily by chylomicrons and very low density lipoproteins. Cholesterol is transported primarily by low density lipoproteins. Hyperlipidemia types include type I, type IIa, type IIb, type III, type IV, and type V. These types can be characterized according to the levels relative to normal of lipids (cholesterol and triglycerides) and lipoproteins described above. Hyperlipidemia types are listed in Table 1 below, wherein "N" refers to normal levels of the substance in the left column, "+" refers to slightly elevated levels, "++" refers to elevated levels, "–" refers to slightly decreased levels, and "– –" refers to decreased levels, all relative to normal. The data in the table are derived from Drug Facts and Comparisons, 52nd Edition (1998) page 1066. Treatment of the a patient presenting one of more of the symptoms listed in Table 1 by the method of treatment and composition of the dosage forms of this invention will lead to a lowering in elevated levels of lipids and lipoproteins in the patient.

TABLE 1

Hyperlipidemia types as a function of relative Lipid and Lipoprotein levels.

| Hyperlipidemia type | I | II a | II b | III | IV | V |
|---|---|---|---|---|---|---|
| Lipids | | | | | | |
| Cholesterol | N + | + + | + + | N + + | N + | N + + |
| Triglycerides | + + | N | + + | N + + | + + | + + |
| Lipoproteins | | | | | | |
| Chylomicrons | + + | N | N | N | N | + + |
| VLDL (pre-beta) | N + | N – | + + | N + | + + | + + |
| ILDL (broad-beta) | | | | + + | | |
| LDL (beta) | – – | + + | + + | + + | N – | – – |
| HDL (alpha) | – – | N | N | N | N – | – – |

Fibrates used as lipid regulating agents in the treatment of lipid disorders include fenofibrate (brand name TRICOR), bezafibrate (brand name BEZALIP), clofibrate (brand name ATROMID-S), gemfibrozil (brand nmae LOPID), and ciprofibrate. In this invention preferred fibrates are water-insoluble or poorly water soluble compounds, and preferably solids, either amorphous or crystalline.

Fibrates can act as prodrugs and be metabolized in vivo to provide species that are active species in the treatment of hyperlipidemia. The major metabolite of fenofibrate found in plasma is fenofibric acid, a fibrate active species which has an elimination half-life of approximately twenty hours. Fenofibric acid lowers plasma triglycerides by potentially inhibiting triglyceride synthesis leading to a reduciton of VLDL released into the circulation. Fenofibric acid also stimulates the catabolism of triglyceride-rich lipoprotein (VLDL).

Fenofibrate also reduces serum uric acid levels in hyperuricemic and normal individuals by increasing the urinary excretion of uric acid.

Fenofibrate or 2-[4-(4-chlorobenzoyl)phenoxy]-2-methyl-propanoic acid 1-methylethyl ester is an example of a poorly water soluble compound. It is a benzophenone containing a para-chlorophenyl group and a para-isopropyloxycarbonyl-isopropoxyphenyl group, both of which are substantially hydrophobic groups. Fenofibrate exhibits a melting point reported to be in the range of 79 to 82° C. (Physician's Desk Reference, 1999 Edition, page 477), which is above that of the symmetrically unsubstituted benzophenone with a reported melting point range of 48 to 51° C. but below that of the symmetrically substituted 4,4'-dichlorobenzophenone with a reported range of 144 to 146° C. (Aldrich Chemical Co. catalog, 1999).

Fenofibrate acts as a potent lipid modulator agent offering unique and significant clinical advantages over existing products in the fibrate class of drugs. Fenofibrate produces substantial reductions in plasma triglyceride levels in hypertriglyceridemic patients and in plasma cholesterol and LDL-cholesterol in hypercholesterolemic and mixed dyslipidemic patients.

Fenofibrate is a prodrug that is absorbed and then hydrolyzed by tissue and plasma esterases to fenofibric acid, its active metabolite. Fenofibric acid, responsible for the pharmacological activity, has a plasma half-life of about 20 hours. Fenofibrate is a poorly water soluble drug and is practically insoluble in water. It is normally poorly and variably absorbed, and has to be taken with food.

The major metabolite of fenofibrate found in plasma is fenofibric acid which has an elimination half-life of approximately twenty hours. Measurement of the detected amount of fenofibric acid in the blood of a patient can reflect the efficacy of fenofibrate up. Fenofibric acid lowers plasma triglycerides by potentially inhibiting triglyceride synthesis leading to a reduciton of VLDL released into the circulation. Fenofibric acid also stimulates the catabolism of triglyceride-rich lipoprotein (VLDL).

Fenofibrate also reduces serum uric acid levels in hyperuricemic and normal individuals by increasing the urinary excretion of uric acid.

There have been a number of improvements in dosage forms of fenofibrate in an effort to increase bioavailability of the drug and hence its efficacy. However, there is still a need for a dosage formulation that can substantially reduce or overcome the differential between the bioavailability of the drug in patients who are fasted versus the bioavailability of the drug in patients who are fed.

Fenofibrate was first available in a pharmaceutical dosage form (Lipidil®) consisting of a hard gelatin capsule containing fenofibrate, lactose, pregelatinized starch and magnesium stearate. After oral administration, during a meal, about 60% of the dose of this conventional form is effectively absorbed and found in the blood as fenofibric acid (Weil et al., The metabolism and disposition of 14C-fenofibrate in human volunteers, Drug. Metabol. Dispos. Biol. Fate. Chem., 18 (1990) 115-120).

Historically, in order to improve the intestinal absorption, another pharmaceutical dosage form was introduced (Lipidil Micro®). European Patent Application 330,532 and U.S. Pat. No. 4,895,726 disclose a fenofibrate composition in which fenofibrate powder is co-micronized with a solid wetting agent. Sodium lauryl sulfate is described as the wetting agent of choice. The co-micronized powder so obtained is mixed with capsule filling excipients such as lactose, starch, crosslinked polyvinyl pyrrolidone (PVP), and magnesium stearate. A study comparing this formulation (Lipidil Micro®) to the conventional form (Lipidil®) had showed statistically significant increase in bioavailability with the former. A formulation of fenofibrate that refers to this patent is currently available in the U.S. under the name TRICOR MICRONIZED®.

European Patent Application 724,877 describes fenofibrate powder co-micronized with a wetting agent in association with a vitamin E component (tocopherol and/or its organic acid ester) for treating or preventing disorders associated with lipoprotein oxidation.

U.S. Pat. No. 4,800,079 describes a medicinal composition in the form of granules with controlled release of fenofibrate. Each granule includes an inert core, a layer based on fenofibrate and a protective layer. Fenofibrate is present in the form of crystalline microparticles of dimensions not greater than 30 µm.

U.S. Pat. No. 4,961,890 describes a process for preparing a controlled release formulation containing fenofibrate in an intermediate layer in the form of crystalline microparticles (less than 30 µm in diameter) within a multilayer layer inert matrix.

European Patent Application 757,911 describes a fenofibrate pharmaceutical dosage form in which fenofibrate is in solution in diethylene glycol monoethyl ether (EMDG) which is a non-ionic surfactant.

European Patent Application 904,781 describes a process for making granules of a solid dispersion of a disintegrant in molten fenofibrate by blending a solid dispersing agent into molten fenofibrate, cooling and solidifying the bulk mixture in a tray, and then milling the solid through a screen to produce granules. Disintegrants include polymers such as starch, croscarmellose sodium, sodium starch glycolate, and crospovidone. Such disintegrants are slow to swell and dissolve in aqueous media. Furthermore, when crosslinked as in the case of crospovidone, a polymeric disintegrant will not be uniformly dissolved in molten drug but rather at best will form micro-domains in molten fenofibrate. In addition, polymeric materials can exhibit phase separation phenomena when distributed in a substance with which there is not complete compatibility. This was shown, in part, by Sheu, M. T. et al., "Characterization and dissolution of fenofibrate solid dispersion systems", Int. J. Pharm. (1994), 103(2), 137-46 using differential scanning calorimetry measurements that found fenofibrate to be incompatible with poly(vinyl pyrrolidone). Thus, preparation of a bulk mixture in the melt followed by solidification and grinding can lead to non-uniform distributions and compositions in granules. This can adversely effect the bioavailability of the active component.

U.S. Pat. No. 5,700,471 discloses a process for the micronization of compounds having low solubility in water by exposing such compounds briefly to a temperature above their respective melting points, dispersing them with turbulence in an aqueous or organic phase, and subsequently cooling the phase to form a fine particle dispersion. However, it is specified (column 2, lines 1-9) that certain substances and specifically fenofibrate are not amenable to processing entirely without organic solvents because their aqueous dispersions agglomerate and cannot be metered. Thus, in example 2 of U.S. Pat. No. 5,700,471, fenofibrate is not directly dispersed in water but rather is first dissolved in a four-fold excess of a water-miscible organic solvent (isopropanol) which must be removed in a subsequent step. Organic solvents can pose flammability risks, exposure dangers to process operators, potential environmental problems, and added expense related to their storage, ultimate removal from a formulation, and disposal. Thus it is desirable to overcome the use of organic solvents where possible.

U.S. Pat. No. 4,880,634 describes a method of production of an excipient system containing a pharmacologically active substance for peroral administration comprised of lipid nano-pellets in an aqueous, colloidal suspension. The method comprises forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid. In the process, a pharmacologically effective substance is dissolved in the lipid or mixture of lipids during the preparation of the lipid nano-pellets. Animal and plant phospholipids such as lecithin and their hydrogenated forms may be employed in the process although the use of chloroform is taught in examples citing phospholipon 100H. The pharmacologically effective substance can be added to the melted lipid in molten form or dissolved or dispersed in the molten lipid.

U.S. Pat. No. 4,895,726 discloses a gelatin capsule dosage form of fenofibrate containing a co-micronized mixture of particles of fenofibrate and a solid surfactant. The dosage form exhibits improved dissolution rate and bioavailability of fenofibrate over that of micronized fenofibrate alone or that of micronized fenofibrate subsequently mixed with solid surfactant. However, the surfactant must be a solid so it can be micronized, and the micronized surfactant in the form of particles is not uniformly juxtaposed or coated on the surface of the fenofibrate particles.

U.S. Pat. No. 5,545,628 discloses a melted and cooled pharmaceutical composition in a hard gelatin capsule for treating hyperlipidemia and/or hypercholesterolemia. The composition contains fenofibrate, one or more polyglycolyzed glycerides, and optionally other polyalkylene glycol polymers that are added to adjust HLB value, melting point, and stabiliity. The composition provides an increased bioavailability of fenofibrate with respect to previously marketed forms of fenofibrate (i.e., non co-micronized Lypantyl 200 RTM., and co-micronized Lypantyl 200 M.RTM.). Commercially available formulations of fenofibrate such as TRICOR Micronized exhibit a food effect, for example, the amount of fenofibrate taken up and metabolized to the active fibrate species, fenofibric acid, depends on the amount and kind of food taken proximal (within about +/− one or two hours before or after) the time of taking the fenofibrate oral dosage form (e.g., capsule or tablet).

Ben-Armor solubilized fenofibrate in nonaqueous dimethyl isosorbide with a miscible wetting agent to improve its bioavailability. Colloidal silicon oxide was added to increase the viscosity, and the liquid so obtained was placed in hard gelatin capsules and sealed. In vivo studies with this formulation indicated no statistically significant difference in bioavailability between the liquid formulation and a conventional form when the product was given with food.

U.S. Pat. Nos. 5,645,856 and 6,096,338 disclose a composition and method of improving the in vivo bioavailability of a hydrophobic drug from a pharmaceutical composition comprising the drug dispersed or dissolved in a digestible oil containing a hydrophilic surfactant which substantially inhibits the in vivo lipolysis of the digestible oil, wherein there is added to the composition a lipophilic surfactant capable of reducing the inhibitory effect of the hydrophilic surfactant. They also disclose a carrier system for a hydrophobic drug which comprises a digestible oil and a pharmaceutically acceptable surfactant for dispersing the oil in vivo upon administration of the carrier system, the surfactant comprising a hydrophilic surfactant component which substantially inhibits the in vivo lipolysis of the digestible oil, and a lipophilic surfactant component capable of reducing the inhibitory effect of the hydrophilic surfactant component.

U.S. Pat. Nos. 5,776,495 and 6,027,747 disclose a solid dispersion with enhanced bioavailability of a surface active agent and at least one therapeutic agent in a hydrophilic carrier having enhanced solubility in an aqueous medium. The dispersion is prepared by dissolving the therapeutic agent in a volatile organic solvent containing a very hydrophilic polymer and without strong heat or vacuum evaporating the solvent to dryness to form a co-precipitate of therapeutic agent and hydrophilic polymer.

U.S. Pat. No. 5,827,536 discloses soluble fenofibrate pharmaceutical dosage formulations exhibiting improved bioavailability after oral administration. However, the formulations contain fenofibrate as a solution in a solubilizing agent consisting of diethylene glycol monoethyl ether.

U.S. Pat. No. 6,042,847 discloses a three-phase pharmaceutical form exhibiting constant and controlled release of an amorphous active ingredient stabilized with polymers for a single daily peroral application. The first phase consists of a core containing an amorphous active ingredient, polyvinylpyrrolidone and a cellulose ether as carriers and as inhibitors of its crystallization, and a surfactant that improves the solubility of the active ingredient and promotes the absorption of the amorphous active ingredient from gastrointestinal tract. The second phase contains a cellulose ether and a mixture of mono-, di- and triglycerides as sustained release agents. The third phase is a poorly soluble or gastro-resistant polymeric film coating.

U.S. Pat. No. 6,068,854 discloses a constant release tablet consisting of a matrix of gelatin in which is dispersed as an emulsion, dispersion or colloid a lipophilic and/or poorly water soluble pharmaceutical substance with a particle size below 200 micrometers.

WO 2000037057 discloses a solution formulation comprising a lipid-regulating agent dissolved in at least one propylene glycol fatty acid ester as the primary solvent medium for the agent, optionally together with one or more emulsifiers including phospholipids.

WO 2000016749 discloses a formulation comprising a solution of a lipid-regulating agent dissolved in at least one propylene glycol fatty acid ester as the primary solvent medium for the agent. One or more emulsifiers may be added to the formulation.

WO 98/31361 discloses a pharmaceutical composition of fenofibrate with high biological availability and method for preparing same. The invention concerns a fenofibrate composition with instant release comprising and inert water-soluble support coated with at least a film containing an active fenofibrate principle in micronized form with a size less than 20 micrometers, a hydrophilic polymer and optionally a surfactant, and optionally one or several external phases or films.

U.S. Pat. No. 5,880,148 discloses a combination of fenofibrate and a vitamin E substance where the fenofibrate is a micronized with a solid surfactant.

U.S. Pat. No. 6,074,670 discloses an immediate-release fenofibrate composition comprising an inert hydrosoluble carrier covered with a layer containing fenofibrate in a micronized form having a size less than 20 micrometers, a hydrophilic polymer and, optionally, a surfactant. In an example cited, a suspension of micronized fenofibrate and sodium lauryl sulfate is suspended in a solution of sodium lauryl sulfate and polyvinylpyrrolidone, sprayed onto 100 to 400 micrometers size lactose particles suspended in a fluidized air bed granulator, and the granulate is placed in capsules or transformed into tablets by mixing with cross-linked PVP, microcrystalline cellulose, colloidal silica, and sodium stearyl fumarate. The composition showed enhanced bioavailability of fenofibrate. However, increased dissolution rates of a formulation of fenofibrate do not translate directly or linearly to increase uptake of the drug, and show that an in vitro experimental result can not necessarily predict the results of an in vivo experiment.

It is generally accepted that water insoluble or poorly water soluble drugs can be made more bioavailable when presented in the form of small particles. In many cases, it is known that small particles must be stabilized against particle size growth and agglomeration by the addition of one or more surface active agents at some point in the preparation of the particles, especially in a size reduction process that employs the input of mechanical energy such as homogenization, microfluidization, milling, such as media milling, precipitation such as from a liquified gas, ball milling and the like. Because they are biocompatible and well tolerated in vivo, preferred surface active agents or particle stabilizers are phospholipids, and preferred small particles of fenofibrate are stabilized by phospholipid particle stabilizers that are also referred to herein as phospholipid surface active substances or species. A phospholipid surface active substance can be a single phospholipid compound or a mixture of phospholipid compounds, a natural phospholipid isolated for example from plants such as soy or animal sourses such as hen egg, or a synthetic phospholipid. Phospholipids that are isolated from plants or animals can be purified into different grades of phospholipids including grades sold for us in food and grades sold for use in pharmaceuticals. For example, Lipoid E 80 may contain phosphatidyl choline, phosphatidyl ethanolamine, lysophosphatidyl choline, lysophosphatidyl ethanolamine, sphingomyelin, and trace quantities of triglycerides, cholesterol, free fatty acids, d,l-alpha-tocopherol, and water.

Microparticles of water insoluble or poorly soluble substances are small particles having diameters of from nanometers to micrometers and refer to solid particles of irregular, non-spherical or spherical shapes. When the insoluble and poorly soluble substances are therapeutically and diagnostically useful substances, formulations containing them as microparticles or small particles provide some specific advantages over unformulated non-micronized drug particles. These advantages include improved oral bioavailability of drugs that are poorly absorbed from the GI tract, development of injectable formulations that are currently available only in oral dosage form, less toxic injectable formulations that are currently prepared with organic solvents, sustained release of intramuscular injectable drugs that are currently administered through daily injection or constant infusion, preparation of inhaled, ophthalmic formulation of drugs that otherwise could not be formulated for nasal or ocular use, as well as other advantages.

Current technology for delivering insoluble drugs as described in U.S. Pat. Nos. 5,091,188; 5,091,187 and 4,725,442 focuses on (a) either coating small drug particles with surface active substances that are natural or synthetic phospholipids or (b) dissolving the drug in a suitable lipophilic carrier and forming an emulsion stabilized with surface active substances that are natural or semisynthetic phospholipids.

U.S. Pat. No. 5,145,684 discloses methods for preparation and dispersions of particles consisting of crystalline drug substance having a surface modifier or surface active substance adsorbed to maintain an effective average particle size of less than about 400 nm. However, the method requires a milling step that can result in impurities being added to the formulation from fractured milling media.

U.S. Pat. Nos. 5,470,583 and 5,336,507 disclose methods for preparation of nanoparticles using a charged phospholipid as a cloud point modifier.

U.S. Pat. No. 5,302,401 discloses compositions and methods for forming nanoparticles with a surface modifier and a cryoprotectant adsorbed thereon.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

U.S. Pat. No. 5,785,976 discloses a heated aqueous emulsification and cooling process for the preparation of solid lipid particles. In that process a solid lipid or bioactive agent or a mixture of solid lipids or bioactive agents is melted and stabilizers, i.e., surface active substances, are added either to the lipid or bioactive agent and to the aqueous phase or to the aqueous phase only. The aqueous phase is heated to the temperature of the melt before mixing and may contain stabilizers, isotonicity agents, buffering substances, cryoprotectants and/or preservatives. The molten lipid compounds and the bioactive agents can be emulsified in the aqueous phase by high-pressure homogenization. The homogenized dispersion is then allowed to cool until solid particles are formed by recrystallization of the dispersed agents. Drugs or other bioactive substances to be incorporated into the particles may be melted together with the lipids or may be dissolved, solubilized or dispersed in the lipid melt before an emulsification by homogenization step.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances-in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

WO 00/30616 discloses a rapidly dispersing solid dry dosage form comprised of a water insoluble compound existing as a nanometer or micrometer particulate solid which is surface stabilized by the presence of at least one phospholipid, the particulate solid being dispersed throughout a bulking matrix. When the dosage form is introduced into an aqueous environment, the bulking matrix is substantially completely dissolved within less than 2 minutes thereby releasing the water insoluble particulate solid in an unaggregated and/or unagglomerated state. The matrix is composed of a water insoluble substance or therapeutically useful water insoluble or poorly water soluble compound, a phospholipid and optionally also at least one non-ionic, anionic, cationic, or amphiphatic surfactant, together with a matrix or bulking agent and if needed a release agent. The volume weighted mean particle size of the water insoluble particle is 5 micrometers or less.

U.S. Pat. No. 5,470,581 discloses a method of coating substrates such as pharmaceutical tablets, food and confectionery forms, agricultural seeds and the like, with a protective film comprises the steps of mixing a cellulosic polymer, maltodextrin, and a plasticizer into water to form an aqueous coating suspension, spraying an effective amount of the coating suspension onto the substrates to form a film coating on the substrates, and drying the film coating on the substrates. Optionally, a detackifier, a secondary film former, a flow aid, and/or a colorant may be dispersed into the coating suspension before applying the coating suspension to the substrates. A dry powder edible film coating composition for use in pharmaceuticals, food and confectionery forms, agricultural seeds, and the like, comprises a dry mixture of a cellulosic polymer, maltodextrin, and a plasticizer. Optionally, the dry coating composition may include a detackifier, a secondary film former, a flow aid, and/or a colorant.

U.S. Pat. No. 5,435,840 discloses a method of marking forms such as pharmaceutical tablets, capsules, confectionery and food with a water based ingestible ink comprising mixing pigments, a polymer, and optionally a plasticizer into water to form an ink dispersion, and printing the ink dispersion onto the forms to form a trademark, logo, or the like.

U.S. Pat. No. 3,981,984 discloses a pigment suspension for a film coating for tablets and the like comprising a solvent, pigment particles dispersed in the solvent, and a low molecular weight alcohol soluble polymer which acts as a protective colloid coating the pigment particles and providing for a higher concentration of pigment particles in the pigment suspension. The method of making the pigment suspension comprises the steps of pouring a solvent into a container, stirring the pigment particles into the solvent to disperse the pigment particles evenly, stirring a protective colloid into the liquid in the container and dispersing it therethrough to make the liquid less viscous and more adaptable for accepting additional pigment particles, and stirring additional pigment particles into the container liquid to obtain the desired pigment suspension. A coating suspension for tablets and the like comprising the pigment suspension dispersed in a polymer solution. The method of making the coating suspension includes dispersing a powdered polymer in a first liquid solvent, stirring a second solvent into the liquid until all of the polymer is in solution, and stirring the pigment suspension into the polymer solution. A coated tablet and the like having as the coating material in a thin film comprising a polymer having pigment particles dispersed therethrough, and a protective colloid coating the pigment particles.

U.S. Pat. No. 4,475,919 discloses a pharmaceutical tablet which consists of a substrate containing a medicament and may be covered with a coating, the coating including a pigment comprising a natural water insoluble edible powder dyed with an edible natural dye. The pigment for coloring the tablet, or other pharmaceutical products, as well as food and cosmetics, is made by suspending a natural water insoluble edible powdered substrate in an aqueous vehicle and dyeing the suspended powdered substrate with an edible natural dye. The liquid is removed to obtain the dry pigment powder of the invention which then can be suspended in a suspending medium and used for coating products to be colored such as food, drug and cosmetic products.

U.S. Pat. No. 4,683,256 and U.S. Pat. No. 4,543,370 disclose a dry powder edible film coating composition for use in pharmaceuticals, confectionery and food, comprising a dry mixture including powdered particles of a film forming non-toxic polymer, powdered edible pigment particles, and an edible polymer plasticizer, the dry mixture being solvent free. A method of making a dry powder edible film coating composition of powdered pigment particles for use in pharmaceuticals, confectionery and food, comprising the steps of mixing a powder of a film forming polymer and powdered pigment particles in a blender to form a polymer-pigment mix, and adding the plasticizer to the blender containing the polymer-pigment mix and mixing until the combined mix is blended to form the dry powder edible film coating composition.

U.S. Pat. No. 4,802,924 discloses a method of providing a film coating on pharmaceutical tablets, foods, confectionery forms and the like by coating them with polydextrose, or a combination of polydextrose and cellulosic polymer, or a layer of polydextrose overcoated by a layer of cellulosic polymer.

U.S. Pat. No. 4,704,295 discloses a non-toxic edible enteric film coating dry powder and aqueous enteric coating suspension for coating pharmaceutical tablets and the like; the enteric coated tablets; and methods of making the enteric coating dry powder, the aqueous coating suspension, and of coating the tablets.

US 4,828,841 and US 4,643,894 disclose a pharmaceutical, confectionery or food tablet coated on all its exterior surfaces with maltodextrin, which masks the characteristic taste of the tablet ingredients and does not have a slimy taste, with the coating composition comprising maltodextrin, an effective amount of a plasticizer to make the maltodextrin non-brittle and non-cracking when coated onto a tablet, an effective amount of a detackifier for making the maltodextrin and plasticizer non-tacky, a secondary film former to impart gloss and strength to the maltodextrin film coating, and a colorant for imparting color. A method of making tablets coated with maltodextrin.

In one aspect while it is advantageous in very many cases to use particulate pharmaceutical formulations wherein particle sizes are stabilized by combinations of phospholipids and surface modifiers according to U.S. Pat. No. 5,922,355, it is sometimes desirable to produce pharmaceutical formulations or pre-formulations which are stabilized by biocompatible phospholipids without the use of additional surface active substances. This can be desirable, for example, when there is a subsequent need to modify the composition of a particle-containing formulation in a step following the formation of the particles such as by the addition of one or more additional ingredients that are not compatible with additional surface modifiers shown to be beneficial in U.S. Pat. No. 5,922,355, the disclosure of which is hereby incorporated by reference. In one aspect it is therefore desirable to produce drug particles stabilized by one or more phospholipids in the absence of additional surface modifiers but which exhibit enhanced stability toward particle growth and which maintain sub-micron and micron size particles on subsequent storage as suspension or solid dosage form.

In another aspect, particle size reduction methods such as those disclosed in U.S. Pat. No. 5,922,355 in which particles of a material are reduced in size in the presence of phospholipid and another surface active substance while the material is maintained in the solid phase require processing for a certain length of time to achieve a desired particle size. The time is directly related to the number of homogenization volume passes or turnovers performed on a volume of a suspension of particles in a size reduction process. It is desirable to further reduce that length of time by providing an improved process that can decrease the overall number of turnovers to achieve a desired particle size.

While these disclosures provide compositions and methods to enhance the bioavailabilty of fibrates such as fenofibrate from various dosage forms, none sufficiently address the need to substantially reduce or eliminate the difference between the amount of the drug taken up in patients who are fasting versus the otherwise enhanced uptake of the drug in patients who are fed or take food with or proximal to the taking of a dosage form of a fibrate. D. Fleischer, Cheng Li, Yuji Zhou, Li-Heng Pao and Aziz Karim in "Drug, Meal and Formulation Interactions Influencing Drug Absorption After Oral Administration," Clin. Pharmacokinet. (1999), Mar:36 (3), 233-264 review information regarding oral drug/meal interaction effects on GI drug absorption.

It is thus an object of this invention to provide to a mammal such as a human patient a method of treatment of dislipidemia and dislipoproteinemia and related disorders in the patient comprising administration of an oral pharmaceutical dosage form of a fibrate such as fenofibrate that substantially reduces or substantially eliminates the difference in the amount of the drug or active fibrate species taken up in the patient when in a fasting state versus the amount taken up using the same dosage level in the same patient when in a fed state.

It is another object of this invention to provide a composition of a pharmaceutical dosage form of a fibrate such as fenofibrate that substantially reduces the difference between the amount of the drug taken up in a patient who is fasting versus the amount of the drug take up in the same patient who is fed.

It is another object of this invention to provide a pharmaceutical dosage form of a fibrate such as fenofibrate in a capsule or a tablet form that can be administered to provide substantial reduction or elimination of an effect of food on the uptake of the fibrate into the patient, ie, substantial reduction or elimination of the food effect.

It is another object of this invention to provide a once-a-day pharmaceutically effective dosage form of a fibrate such as fenofibrate that can be administered to a patient in need of treatment by the drug.

BRIEF SUMMARY OF THE INVENTION

The present invention provides a method of treating dislipidemia and dislipoproteinemia in a mammal which method comprises administering to the mammal a therapeutically effective oral dosage form comprising microparticles of a solid fibrate that are stabilized by a phospholipid surface active substance wherein the dosage form provides into the blood of the patient in a fasted state a therapeutically effective amount of a fibrate active species that is at least 90% of the AUC amount of the fibrate active species provided by the dosage form into the blood of the patient when in a fed state.

In a preferred aspect, the present invention provides a method of treating dislipidemia and dislipoproteinemia in a human patient which method comprises administering to the patient a therapeutically effective oral dosage form comprising microparticles of a solid fenofibrate that are stabilized by a phospholipid surface active substance wherein the dosage form provides into the blood of the patient in a fasted state a therapeutically effective amount of fenofibrate active species, fenofibric acid, that is at least 90% of the AUC amount of the fenofibrate active species provided by the dosage form into the blood of the patient in a fed state.

In another aspect the present invention also provides an orally administered pharmaceutical composition comprising microparticles of solid fibrate that are stabilized by a phospholipid surface active substance, wherein the microparticles are prepared in the presence of the phospholipid surface active substance, and wherein a therapeutically effective amount of the composition provides a quantity of fibrate active species to a fasted human patient in need of treatment by the fibrate that is greater than 90% of the quantity of the fibrate active species provided by the amount to the patient when fed a high fat meal.

In a preferred aspect the present invention also provides an orally administered pharmaceutical composition comprising microparticles of solid fenofibrate that are stabilized by a phospholipid surface active substance, wherein the microparticles are prepared in the presence of the phospholipid surface active substance, and wherein a therapeutically effective amount of the composition provides a quantity of fenofibrate active species to a fasted human patient in need of treatment by the fenofibrate that is greater than 90% of the quantity of the fenofibrate active species provided by the amount to the patient when fed a high fat meal.

In another aspect, this invention provides a pharmaceutically effective composition comprising small particles of a fibrate stabilized by a phospholipid stabilizing agent which when dried in the presence of a sugar and optionally also in the presence of a carbohydrate-derived alcohol can be formulated as a an oral dosage form such as a capsule or tablet dosage form for oral administration to patients in need of treatment by the fibrate. The dosage form provides dosage levels of drug or fibrate active species into the blood of a patient in a fasted or fed state wherein the amount of drug or active species that the patient receives in the fasted state differs by less than 25%, preferably by less than 20%, more preferably by less than 15%, even more preferably by less than 10%, and most preferably by less than 5% from the amount of drug or active species that the patient receives in the fed state.

In a preferred aspect, this invention provides a pharmaceutically effective composition comprising small particles of fenofibrate stabilized by a phospholipid stabilizing agent which when dried in the presence of a sugar and optionally also in the presence of a carbohydrate-derived alcohol can be formulated as a capsule or tablet dosage form for oral administration to a patient in need of treatment by fenofibrate. The dosage form provides dosage levels of fenofibrate active species into the blood of a patient in a fasted or fed state wherein the amount of drug or active species that the patient receives in the fasted state differs by less than 25%, preferably by less than 20%, more preferably by less than 15%, even more preferably by less than 10%, and most preferably by less than 5% from the amount of drug or active species that the patient receives in the fed state.

In a clinical study using capsule dosage forms and monitoring the pharmacokinetic comparison of a single dose of a phospholipid-stabilized fenofibrate formulation of this invention versus a comicronized fenofibrate (Lipanthyl 67M) in healthy volunteers under fed and fasted conditions, distinct advantages are seen. For example, under fasted conditions, it was unexpectedly found that the formulation of this invention provided a statistically significant increased relative bioavailability of approximately 1.5 times that of the comicronized formulation as evidenced by an 84% higher mean maximum concentration ($C_{max}$) of the drug and approximately 50% higher mean AUC's. This significant difference between the two formulations disappeared under fed conditions.

When the bioavailability of the comicronized formulation under fed versus fasted conditions was compared, the $C_{max}$ significantly increased by 211% and the mean AUC's significantly increased by over 70%. In addition, the mean terminal half-life appeared to be shortened.

In contrast and unexpectedly, when the bioavailability of the formulation of this invention under fed versus fasted conditions was compared, the $C_{max}$ significantly increased by only 61% and the mean AUC's were increased by only 13%. The relative bioavailability was approximately 1.14 when comparing fasted versus fed conditions using the formulation of this invention. No significant variation in mean terminal half-life was observed.

The phospholipid-stabilized fibrate particle formulation of this invention provides a pharmacokinetic profile in which the effect of ingestion of food on the uptake of the drug is substantially reduced (even up to the point of elimination of the effect of the ingestion of food) over that observed with the commercially available comicronized formulation. In a preferred aspect, the phospholipid-stabilized fenofibrate particle formulation of this invention provides a pharmacokinetic profile in which the effect of ingestion of food on the uptake of the drug is substantially reduced over that observed with the commercially available comicronized formulation.

The small particles or microparticles of solid fibrate of this invention are prepared in the presence of a phospholipid surface active agent as a particle stabilizer. Preferred methods of preparation include the methods of Haynes disclosed in U.S. Pat. Nos. 5,091,187 and 5,091,188 which are hereby incorporated by reference and by improved processes described herein as well as the methods in U.S. Ser. No. 60/198,579 and U.S. Ser. No. 60/203,366. Other useful methods of preparation include the methods of Parikh et al disclosed in U.S. Pat. No. 5,922,355 which is hereby incorporated by reference, PCT/US99/13755 which is hereby incorporated by reference, and potentially other milling methods such as ball milling, media milling and the like for example such as disclosed in U.S. Pat. Nos. 4,727,077, 4,006,025, and 4,294,916 if these methods are applied using a phospholipid or a mixture of phospholipids as a particle stabilizer.

Small particles or microparticles of fenofibrate of this invention are conveniently prepared by an energy input process, and especially by a microfluidization process to provide the small particles in the form of an aqueous suspension. The microfluidization process is a wet or aqueous, one- or two-stage size reduction process that is done in the presence of a liquefied or vesiclar surface active agent (e.g., one or more pharmaceutically acceptable phospholipids such a single phospholipid or a mixture of phospholipids such as soy-derived phospholipid, egg phospholipid, and especially Lipoid E80—a purified egg phospholipid, natural phospholipids, synthetic phospholipids, purified natural phospholipids, fractions of natural phospholipids, charged anionic or cationic phospholipids, and combinations thereof), and optionally in the presence of pharmaceutically acceptable additives or excipients such as sucrose, sorbitol, other surface active agents, and preferably in an aqueous sodium phosphate buffer. When the microfluidization is done in two stages or processing steps wherein the first stage is run at a temperature above the melting point of the drug and the second stage is run below the melting point of the drug, we refer to such a process as a hot melt microfluidization process. Water is then subsequently removed from the suspension by a lyophilization (i.e., a freeze-drying step) to form a lyophilized and substantially dry powder comprising the solid particles of fenofibrate. The water can also be removed by other means such as by spray drying.

Small particles of fenofibrate of this invention stabilized by phospholipid can be prepared as a suspension by a process comprising the steps of (a) mixing at high shear an admixture of a poorly water soluble drug and one or more than one surface active substance in an aqueous carrier in the absence of an organic solvent within a first temperature range at or above the melting point of the poorly water soluble drug to form a heated suspension containing the drug, then (b) homogenizing the heated suspension in a first pressure range and within the first temperature range to form a heated homogenate containing the drug, then (c) cooling the heated homogenate to a second temperature range below the melting temperature of the poorly water soluble drug to form a transiently stable cooled homogenate containing the drug, then (d) applying a particle stabilizing energetic process to the cooled homogenate within a second temperature range below the melting point of the drug and in a second pressure range to form a cooled dispersion of stabilized small particles containing the drug, and then (e) optionally drying the cooled dispersion to form dried small particles containing the poorly water soluble drug.

In a typical procedure, a premix of fenofibrate, phospholipid Lipoid E80 (dispensed frozen but liquefied or vesiclized at processing temperatures), sorbitol, and sucrose in 10 millimolar aqueous phosphate buffer at pH 8 is microfluidized above the melting temperature of fenofibrate for about 3 to 10 volume passes, cooled, and further microfluidized for another 10 volume passes to form a suspension of microparticles of fenofibrate stabilized by phospholipid in aqueous sorbitol/sucrose/phosphate buffer.

Particularly important to the preparation of the composition of this invention is the use of two homogenization steps separated by a cooling step. The first homogenization step is done on a heated suspension having the poorly water soluble drug in a molten phase in the presence of one or more than one surface active substance to provide a heated homogenate containing the drug. The heated homogenate is usually in the form of a microemulsion comprising small molten particles or droplets of drug stabilized by one or more than one surface active substance. The heated homogenate containing the drug is then cooled to provide a transiently stable cooled homogenate containing the drug. The transiently stable cooled homogenate comprises small particles of drug in which the drug is in a solid phase which may be amorphous, crystalline, or a combination of both. The small particles of the cooled homogenate are stabilized by the surface active substance or substances but the particles are transiently stable with respect to particles size growth and eventual precipitation of solid drug from the aqueous carrier.

The second homogenization step is done on the cooled homogenate after a cooling step to produce a cooled dispersion of small particles containing the drug and having greater stability to particle growth and precipitation than the cooled homogenate. The second homogenization step is a stabilizing energetic process. It provides small particles that are more stable than the transiently stable particles of the cooled homogenate prepared in the first homogenization step and prevents relatively large crystals and/or agglomerates of the poorly water soluble drug from forming. The second homogenization step thereby facilitates the formation of stabilized small particles of the poorly water soluble drug. It also provides overall rapid formation of desired small particles containing the poorly water soluble drug. Optionally, the small particles can be isolated by a drying process, for example by lyophilization or by spray drying. Thus, the process can provide dried small particles containing a poorly water soluble drug. In the absence of the second homogenization step, very large amounts of the poorly water soluble drug can precipitate from the transiently stable aqueous cooled homogenate or can form a sediment by precipitation from the aqueous carrier.

In one aspect of this invention, we have unexpectedly found that small particles containing the poorly water soluble drug fenofibrate can be prepared by a process comprising the steps of (a) mixing at high shear an admixture of fenofibrate and one or more than one surface active substance in an aqueous carrier in the absence of an organic solvent within a first temperature range above the melting point of fenofibrate to form a heated suspension containing fenofibrate, then (b) homogenizing the heated suspension in a first pressure range and within the first temperature range to form a heated homogenate containing fenofibrate, then (c) cooling the heated homogenate to a second temperature range below the melting temperature of fenofibrate to form a transiently stable cooled homogenate containing fenofibrate, then (d) applying a particle stabilizing energetic process to the cooled homogenate within a second temperature range and in a second pressure range to form a cooled dispersion of stabilized small particles containing fenofibrate, and then (e) optionally drying the cooled dispersion to form dried small particles containing fenofibrate. Particularly important to this aspect of the invention is the use of two homogenization steps separated by a cooling step and the use of a phospholipid as a surface active substance. The first homogenization step is done on a heated suspension in the presence of a phospholipid as a surface active substance, in the absence of an organic solvent, and wherein fenofibrate is molten to provide a homogenized microemulsion containing fenofibrate. The second homogenization step is done on a transiently stable cooled homogenate in the presence of the phospholipid and wherein the fenofibrate is a solid to provide a homogenized dispersion of small particles containing fenofibrate. In the absence of the second homogenization step, relatively large crystals of fenofibrate readily form from the transiently stable cooled homogenate. In the absence of a heated first homogenization step on the molten drug, homogenization of solid fenofibrate to provide a suspension of small particles of fenofibrate takes a prolonged or much longer time in the same homogenization apparatus under substantially the same homogenization conditions of pressure and temperature relative to the time taken in the second homogenization step of this invention.

It is an advantage of this invention that small particles containing a poorly water soluble drug stabilized with one or more than one surface active substances can be prepared as a dispersion in an aqueous carrier or as dried small particles.

It is another advantage of this invention that small particles containing a poorly water soluble drug can be prepared in the absence of an organic solvent.

It is another advantage of this invention that small particles containing a poorly water soluble drug can be prepared using pharmaceutically acceptable excipients such as phospholipids, sugars and polyols.

It is a further advantage of this invention that a suspension of small particles containing a poorly water soluble drug can be prepared which suspension is relatively stable to mechanical agitation and to growth of larger crystals of the drug over a period of time.

It is another advantage of this invention that small particles containing fenofibrate can be prepared without the use of an organic solvent.

It is a further advantage of this invention that a suspension of small particles containing fenofibrate can be prepared which suspension is relatively stable to mechanical agitation and to growth of larger crystals of the drug over a period of time.

It is a further advantage of this invention that a composition of a pharmaceutical dosage form of fenofibrate is provided that substantially reduces the difference between the amount of the drug taken up in patients who are fasting versus the amount of the drug in patients who are fed.

It is yet another advantage of this invention that a pharmaceutical dosage form of fenofibrate is provided that can be administered orally in a capsule or a tablet form.

It is still another advantage of this invention that a once-a-day pharmaceutically effective dosage form of fenofibrate is provided that can be administered orally to a patient in need of treatment by the drug without regard to the amount of food a patient has ingested prior to or following administration of the dosage form. These and other advantages will be readily apparent from the description of the invention.

BRIEF DESCRIPTION OF THE DRAWINGS

FIG. 1 is an optical microscopic comparison of microfluidized fenofibrate with micronized fenofibrate and fenofibrate compositions prepared in the presence of starch.

FIG. 2 is a comparison of the oral bioavailability of microparticles of fenofibrate prepared by microfluidization in the presence of a phospholipid stabilizing agent versus the oral bioavailability of micronized fenofibrate under fasting, low fat fed, and high fat fed conditions.

FIG. 3A is a graph of fenofibric acid mean plasma concentration (in ng/ml) versus time (in hours) found after oral administration of a 160 mg fenofibrate-containing tablet prepared according to this invention compared to that of a commercially available 200 mg TRICOR capsule each take proximal to ingestion of a low fat meal (n=24).

FIG. 3B is a graph of fenofibric acid Ln mean plasma concentration (in mg/ml) versus time (in hours) found after oral administration of a 160 mg fenofibrate-containing tablet prepared according to this invention compared to that of a commercially available 200 mg TRICOR capsule taken proximal to ingestion of a low fat meal (n=24).

DETAILED DESCRIPTION OF THE INVENTION

The present invention provides a method of treating dislipidemia and dislipoproteinemia in a mammal which method comprises administering to the mammal a therapeutically effective oral dosage form comprising microparticles of a solid fibrate that are stabilized by a phospholipid surface active substance wherein the dosage form provides into the blood of the patient in a fasted state a therapeutically effective amount of the fibrate that is at least 90% of the AUC amount of the fibrate provided by the dosage form into the blood of the patient in a fed state. AUC refers to area under the curve.

In a preferred aspect, the present invention provides a method of treating dislipidemia and dislipoproteinemia in a human patient which method comprises administering to the patient a therapeutically effective oral dosage form comprising microparticles of a solid fenofibrate that are stabilized by a phospholipid surface active substance wherein the dosage form provides into the blood of the patient in a fasted state a therapeutically effective amount of fenofibrate active species that is at least 90% of the AUC amount of the fenofibrate active species provided by the dosage form into the blood of the patient in a fed state.

In another aspect the present invention also provides an orally administered pharmaceutical composition comprising microparticles of solid fibrate that are stabilized by a phospholipid surface active substance, wherein the microparticles are prepared in the presence of the phospholipid surface active substance, and wherein a therapeutically effective amount of the composition provides a quantity of fibrate active species to a fasted human patient in need of treatment by the fibrate that is greater than 90% of the quantity of the fibrate active species provided by the amount to the patient when fed a high fat meal.

In a preferred aspect the present invention also provides an orally administered pharmaceutical composition comprising microparticles of solid fenofibrate that are stabilized by a phospholipid surface active substance, wherein the microparticles are prepared in the presence of the phospholipid surface active substance, and wherein a therapeutically effective amount of the composition provides a quantity of fenofibrate active species to a fasted human patient in need of treatment by the fenofibrate that is greater than 90% of the quantity of the fenofibrate active species provided by the amount to the patient when fed a high fat meal.

In another aspect, this invention provides a pharmaceutically effective composition comprising small particles of a fibrate stabilized by a phospholipid stabilizing agent which when dried in the presence of a sugar and optionally also in the presence of a carbohydrate-derived alcohol can be formulated as a capsule or tablet dosage form for oral administration to patients in need of treatment by the fibrate. The dosage form provides dosage levels of drug or fibrate active species into the blood of a patient in a fasted or fed state wherein the amount of drug or active species that the patient receives in the fasted state differs by less than 25%, preferably by less than 20%, more preferably by less than 15%, even more preferably by less than 10%, and most preferably by less than 5% from the amount of drug or active species that the patient receives in the fed state.

In a preferred aspect, this invention provides a pharmaceutically effective composition comprising small particles of fenofibrate stabilized by a phospholipid stabilizing agent which when dried in the presence of a sugar and optionally also in the presence of a carbohydrate-derived alcohol can be formulated as a capsule or tablet dosage form for oral administration to a patient in need of treatment by fenofibrate. The dosage form provides dosage levels of fenofibrate active species into the blood of a patient in a fasted or fed state wherein the amount of drug or active species that the patient receives in the fasted state differs by less than 25%, preferably by less than 20%, more preferably by less than 15%, even more preferably by less than 10%, and most preferably by less than 5% from the amount of drug or active species that the patient receives in the fed state.

This invention describes an orally administered pharmaceutical composition comprising microparticles of solid fenofibrate that are stabilized by a phospholipid surface active substance, wherein the microparticles are prepared in the presence of the phospholipid surface active substance, and wherein a therapeutically effective amount of the composition provides a quantity of fenofibrate to a fasted human patient in need of treatment by fenofibrate that is greater than 80% of the quantity of fenofibrate provided by the amount to the patient when fed a high fat meal comprising at least 1000 calories 50% of which are from fat.

This invention also describes an orally administered pharmaceutical composition comprising microparticles of solid fenofibrate that are stabilized by a phospholipid surface active substance, wherein the microparticles are prepared in the presence of the phospholipid surface active substance and one or more excipients, and wherein a therapeutically effective amount of the composition provides a quantity of fenofibrate to a fasted human patient in need of treatment by fenofibrate that is greater than 80% of the quantity of fenofibrate provided by the amount to the patient when fed a high fat meal comprising at least 1000 calories 50% of which are from fat.

As used herein, a fasted patient is defined as a patient who has not eaten any food, i.e., has fasted for at least 10 hours before the administration of a dosage form of fenofibrate and who does not eat any food and continues to fast for at least 4 hours after the administration of the dosage form. The dosage form is administered with 180 ml of water during the fasting period, and water can be allowed ad libitum after 2 hours.

As used herein, a fed patient is defined as a patient who has fasted for at least 10 hours overnight and then has consumed an entire test meal within 30 minutes of first ingestion. The dosage form is administered with 180 ml of water within 5 minutes after completion of the meal. No food is then allowed for at least 4 hours post-dose. Water can be allowed ad libitum after 2 hours. A high fat test meal provides approximately 1000 calories to the patient of which approximately 50% of the caloric content is derived from fat content of the meal. A representative high fat high calorie test meal comprises 2 eggs fried in butter, 2 strips of bacon, 2 slices of toast with butter, 4 ounces of hash brown potatoes, and 8 ounces of whole milk to provide 150 protein calories, 250 carbohydrate calories, and 500 to 600 fat calories. High fat meals can be used in clinical bioequivalence and bioavailability studies of fenofibrate. High fat meals promote increased absorption and uptake of fenofibrate.

The absence or elimination of a food effect can be concluded when the 90% confidence intervals for the ratio of the geometric means based on log-transformed data in clinical studies of fed and fasted treatments fall within 80% to 125% for AUC (area under the concentration time curve) and 70% to 143% for $C_{max}$ (peak concentration). The presence of a food effect can be concluded when the 90% confidence intervals for the ratio of the geometric means based on log-transformed data in clinical studies of fed and fasted treatments fall outside 80% to 125% for AUC and outside 70% to 143% for $C_{max}$.

As used herein, "small particle" refers to a particle or a distribution of particles having a diameter or an average diameter, respectively, of from nanometers to micrometers. Small particles are microparticles, as used herein, and also refer to solid particles of irregular, non-spherical or spherical shapes.

By "transiently stable" we mean that the small particles of the cooled homogenate remain as small particles in a dispersion of the aqueous carrier at the size finally produced in the first homogenization step for a relatively short period of time and not indefinitely. The period of time that a cooled homogenate remains transiently stable can vary from up to about one second to up to about 48 hours, and preferably from up to about 15 minutes to up to about 24 hours, and most preferably from up to about 6 hours to up to about 24 hours although though the period of time can vary with many factors. For example as commonly seen in recrystallization of a crystalline substance from an organic solvent, the growth and precipitation of crystals can be induced or enhanced by the presence of seed crystals, by stirring of a cooled supersaturated solution of drug, and by scratching the internal surface of a vessel containing supersaturated dissolved drug below the level of the liquid thereby creating nucleation sites for crystallization. Such crystal growth is not desirable in the present invention. The transiently stable particles can grow slightly in size (i.e., in average diameter) over the relatively short period of time by as much as 1000% of their original size or more from that size produced in the heated homogenization step, but preferably will remain at the size at which they were produced in the first homogenization step up to a size about 100% larger in diameter, and more preferably up to a size about 50% larger in diameter. After the relatively short period of time, the particles will continue to become larger such as by Ostwald ripening and crystallization. After the relatively short period of time, drug may also crystallize in the form of large particles from the suspension. The particles of the heated homogenate may also irreversibly agglomerate after the relatively short period of time. Additionally, after the relatively short period of time, the components of the formulation may phase separate from the aqueous carrier and optionally precipitate and separate into components that contain largely drug and largely surface active substance.

Water insoluble and poorly water soluble compounds are those having poor solubility in water at or below normal physiological temperatures, that is <5 mg/ml at physiological pH (6.5-7.4). Preferably their water solubility is <1 mg/ml, and more preferably <0.1 mg/ml. It is desirable that the drug be stable in water as a dispersion. Otherwise or in addition a dried form such as a lyophilized or spray-dried solid form may be desirable for example for use in formation of drug delivery compositions including capsules, tablets, and formulations with additional excipients and drugs.

Examples of some preferred water-insoluble drugs that are also suitable for preparation into small particles and dosage forms according to this invention include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antarrhythmics, antihypertensive agents, antineoplastic agents, hormones, and nutrients. A detailed description of these and other suitable drugs may be found in Remington's Pharmaceutical Sciences, 18th edition, 1990, Mack Publishing Co. Philadelphia, Pa. which is hereby incorporated by reference.

Drugs that are poorly soluble in water can have pharmaceutical efficacy in a number of therapeutic and diagnostic imaging areas. Non-limiting classes of compounds and agents from which poorly water soluble drugs that melt without decomposition and are useful in this invention can be selected include anesthetic agents, ace inhibiting agents, antithrombotic agents, anti-allergic agents, antibacterial agents, antibiotic agents, anticoagulant agents, anticancer agents, antidiabetic agents, antihypertension agents, antifungal agents, antihypotensive agents, antiinflammatory agents, antimitotic agents, antimigraine agents, antiparkinson agents, antirheumatic agents, antithrombins, antiviral agents, beta blockering agents, bronchospamolytic agents, calcium antagonists, cardiovascular agents, cardiac glycosidic agents, carotenoids, cephalosporins, contraceptive agents, cytostatic agents, diuretic agents, enkephalins, fibrinolytic agents, growth hormones, immunosupressants, insulins, interferons, lactation inhibiting agents, lipid-lowering agents, lymphokines, neurologic agents, prostacyclins, prostaglandins, psycho-pharmaceutical agents, protease inhibitors, magnetic resonance diagnostic imaging agents, reproductive control hormones, sedative agents, sex hormones, somatostatins, steroid hormonal agents, vaccines, vasodilating agents, and vitamins.

Preferred drugs suitable for processing into small particles according to the method of this invention melt without decomposition in admixtures, suspensions, dispersions, and homogenates, preferably in a temperature range from about physiological temperature 37° C. to about 275° C., and more preferably in a temperature range from just above physiological temperature, about 40° C., to about 230° C. In one aspect, preferred suitable drugs melt without decomposition in the range from physiological temperature at about 37° C. to the boiling point of water at atmospheric pressure, i.e., up to about 100° C. but not including 100° C. In this case, the aqueous carrier can be maintained at the first temperature range generally without the need of pressurization to maintain the aqueous carrier as a liquid during the heated homogenization process. In another aspect of this invention, preferred suitable drugs melt without decomposition in the range from at the boiling point of the aqueous carrier under ambient pressure, i.e., from 100° C. up to 275° C. In this case, the aqueous carrier can be maintained at the first temperature range generally by using a pressurized apparatus to maintain the aqueous carrier as a liquid during the heated homogenization process. Of course, if desired, a pressurized apparatus can be used in the range below the boiling point of the aqueous carrier such as in the region of from 50° C. to about 100° C., and the aqueous carrier will also be maintained as a liquid.

Non-limiting examples of representative poorly soluble drugs suitable for use in the hot melt process that is described herein for the preparation of microparticles of fenofibrate stabilized with one or more (i.e., a mixture of) phospholipid stabilizing agents and that melt without decomposition in admixtures, suspensions, dispersions, and homogenates of this invention at temperatures at or below 275° C. can be selected from the group consisting albendazole (m.p. 208-210° C.), albendazole sulfoxide, alfaxalone (m.p. 172-174° C.), acetyl digoxin, acyclovir analogs melting at or below 275° C., alprostadil, aminofostin, anipamil, antithrombin III, atenolol (m.p. 146-148° C.), azidothymidine, beclobrate (m.p. 200-204° C.), beclomethasone (m.p. 117-120° C.), belomycin, benzocaine (m.p. 88-90° C.) and derivatives, beta carotene (m.p. 183° C.), beta endorphin, beta interferon, bezafibrate (m.p. 186° C.), binovum, biperiden (m.p. 112-116° C.), bromazepam (m.p. 237-238° C.), bromocryptine, bucindolol, buflomedil (m.p. 192-193° C.), bupivacaine (m.p. 107-108° C.), busulfan (m.p. 114-118° C.), cadralazine (m.p. 160-162° C.), camptothesin (m.p. 264-267 and 275° C.), canthaxanthin (m.p. 217° C.), captopril (m.p. 103-104° C.), carbamazepine (m.p. 190-193° C.), carboprost, cefalexin, cefalotin, cefamandole (m.p. 190° C.), cefazedone, cefluoroxime, cefinenoxime, cefoperazone (m.p. 169-171° C.), cefotaxime, cefoxitin (m.p. 149-150° C.), cefsulodin (m.p. 175° C.), ceftizoxime, chlorambucil (m.p. 64-66° C.), chromoglycinic acid, ciclonicate (m.p. 127-128° C.), ciglitazone, clonidine (m.p. 130° C.), cortexolone, corticosterone (m.p. 180-182° C.), cortisol (m.p. 212-220° C.), cortisone (m.p. 220-224° C.), cyclophosphamide (m.p. 41-45° C.), cyclosporin A (m.p. 148-151° C.) and other cyclosporins, cytarabine (m.p. 212-213° C.), desocryptin, desogestrel (m.p. 109-110° C.), dexamethasone esters such as the acetate (m.p. 238-240° C.), dezocine, diazepam (m.p. 125-126° C.), diclofenac, dideoxyadenosine (m.p. 160-163° C.), dideoxyinosine, digitoxin (m.p. 256-257° C.), digoxin, dihydroergotamine (m.p. 239° C.), dihydroergotoxin, diltiazem (m.p. 207-212° C.), dopamine antagonists, doxorubicin (m.p. 229-231° C.), econazole (m.p. 87° C.), endralazine (m.p. 185-188° C.), enkephalin, enalapril (m.p. 143-145° C.), epoprostenol, estradiol (m.p. 173-179° C.), estramustine (m.p. 104-105° C.), etofibrate (m.p. 100° C.), etoposide (m.p. 236-251° C.), factor ix, factor viii, felbamate (m.p. 151-152° C.), fenbendazole (m.p. 233° C.), fenofibrate (m.p. 79-82° C.), flunarizin (m.p. 252° C.), flurbiprofen (m.p. 110-111° C.), 5-fluorouracil (m.p. 282-283° C.), flurazepam (m.p. 77-82° C.), fosfomycin (m.p. 18 94° C.), fosmidomycin, furosemide (m.p. 206° C.), gallopamil, gamma interferon, gentamicin (m.p. 102-108° C.), gepefrine (m.p. 155-158° C.), gliclazide (m.p. 180-182° C.), glipizide (m.p. 208-209° C.), griseofulvin (m.p. 220° C.), haptoglobulin, hepatitis B vaccine, hydralazine (m.p. 172-173° C.), hydrochlorothiazide (m.p. 273-275° C.), hydrocortisone (m.p. 212-220° C.), ibuprofen (m.p. 75-77° C.), ibuproxam (m.p. 119-121° C.), indinavir, indomethacin (m.p. 155° C.), iodinated aromatic x-ray contrast agents melting below 275° C. such as iodamide (m.p. 255-257° C.), ipratropium bromide (m.p. 230-232° C.), ketoconazole (m.p. 146° C.), ketoprofen (m.p. 94° C.), ketotifen (m.p. 152-153° C.), ketotifen fumarate (m.p. 192° C.), K-strophanthin (m.p. ~175° C.), labetalol, lactobacillus vaccine, lidocaine (m.p. 68-69° C.), lidoflazin (m.p. 159-161° C.), lisuride (m.p. 186° C.), lisuride hydrogen maleate (m.p. 200° C.), lorazepam (m.p. 166-168° C.), lovastatin, mefenamic acid (m.p. 230-231° C.), melphalan (m.p. 182-183° C.), memantin, mesulergin, metergoline (m.p. 146-149° C.), methotrexate (m.p. 185-204° C.), methyl digoxin (m.p. 227-231° C.), methylprednisolone (m.p. 228-237° C.), metronidazole (m.p. 158-160° C.), metisoprenol, metipranolol (m.p. 105-107° C.), metkephamide, metolazone (m.p. 253-259° C.), metoprolol, metoprolol tartrate, miconazole (m.p. 135° C.), miconazole nitrate (m.p. 170 and 185° C.), minoxidil (m.p. 248° C.), misonidazol, molsidomin, nadolol (m.p. 124-136° C.), nafiverine (m.p. 220-221° C.), nafazatrom, naproxen (m.p. 155° C.), natural insulins, nesapidil, nicardipine (m.p. 168-170° C.), nicorandil (m.p. 92-93° C.), nifedipine (m.p. 172-174° C. niludipin, nimodipine, nitrazepam (m.p. 224-226° C.), nitrendipine, nitrocamptothesin, 9-nitrocamptothesin, oxazepam (m.p. 205-206° C.), oxprenolol (m.p. 78-80° C.), oxytetracycline (m.p. 181-182° C.), penicillins such as penicillin G benethamine (m.p. 147-147° C.), penecillin O (m.p. 79-81° C.), phenylbutazone (m.p. 105° C.), picotamide, pindolol (m.p. 171-173° C.), piposulfan (m.p. 175-177° C.), piretanide (m.p. 225-227° C.), piribedil (m.p. 98° C.), piroxicam (m.p. 198-200° C.), pirprofen (m.p. 98-100° C.), plasminogenic activator, prednisolone (m.p. 240-241° C.), prednisone (m.p. 233-235° C.), pregnenolone (m.p. 193° C.), procarbacin, procaterol, progesterone (m.p. 121° C.), proinsulin, propafenone, propanolol, propentofyllin, propofol, propranolol (m.p. 96° C.), rifapentin, simvastatin, semi-synthetic insulins, sobrerol (m.p. 130° C.), somastotine and its derivatives, somatropin, stilamine, sulfinalol whose hydrochloride melts at 175° C., sulfinpyrazone (m.p. 136-137° C.), suloctidil (m.p. 62-63° C.), suprofen (m.p. 124° C.), sulproston, synthetic insulins, talinolol (m.p. 142-144° C.), taxol, taxotere, testosterone (m.p. 155° C.), testosterone propionate (m.p. 118-122° C.), testosterone undecanoate, tetracane HI (m.p. 150° C.), tiaramide (HCl m.p. 159-161° C.), tolmetin (m.p. 155-157° C.), tranilast (m.p. 211-213° C. triquilar, tromantadine (HCl m.p. 157-158° C.), urokinase, valium (m.p. 125-126° C.), verapamil (m.p. 243-246° C.), vidarabine, vidarabine phosphate sodium salt, vinblastine (m.p. 211-216° C.), vinburin, vincamine (m.p. 232-233° C.), vincristine (m.p. 218-220° C. vindesine (m.p. 230-232° C.), vinpocetine (m.p. 147-153° C.), vitamin A (m.p. 62-64° C.), vitamin E succinate (m.p. 76-78° C.), and x-ray contrast agents. Drugs can be neutral species or basic or acidic as well as salts such as exist in the presence of an aqueous buffer. While compositions of microfluidized fenofibrate stabilized with a phospholipid surface active agent and formulated according to this invention provide substantial reduction to elimination of the food effect observed with other formulations of fenofibrate, the hot melt method of production of such microparticles has application to other drugs, especially water insoluble or poorly water soluble drugs and to other surface active substances.

Examples of some suitable surface active substances that are useful in the hot melt microfluidization process include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxypropylcellulose, hydroxypropylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylarnmonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances include one or combination of the following: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Speciality Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide.

Preferred surface active substances are phospholipid surface active substances. By phospholipid surface active substances or phospholipid surface active agents is meant a single phospholipid or a mixture of two or more phospholipids, for example a mixture of two or three or four or five or from six to about ten phospholipids. Suitable phospholipids include animal and plant phospholipids; egg phospholipids; soya bean phospholipids; corn phospholipids; wheat germ, flax, cotton, and sunflower seed phospholipids; milk fat phospholipids; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bonds such as dioleoyl phosphatidylcholine and egg phosphatidylcholine that are not stable as powders but are hygroscopic and can absorb moisture and become gummy; phospholipids composed of saturated fatty acids that are stable as powders and are less amenable to absorption of moisture; phosphatidylserines; phosphatidylcholines; phosphatidylethanolamines; phosphatidylinositols;

Phosphatidylglycerols such as dimyristoyl phosphatidylglycerol, L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available phospholipids such as those available from Avanti Polar Lipids, Inc. of Alabaster, Ala., USA. In the absence of an internal counterion in the phospholipid, a preferred counterion is a monovalent cation such as sodium ion. The phospholipid may be salted or desalted, hydrogenated, partially hydrogenated, or unsaturated, natural, synthetic, or semisynthetic.

Preferred phospholipids include Lipoid E80, Lipoid EPC, Lipoid SPC, DMPG, Phospholipon 100H a hydrogenated soybean phosphatidylcholine, Phospholipon 90H, Lipoid SPC-3, and combinations thereof. A currently most preferred phospholipid is Lipoid E80.

The concentration of surface active substance added to the formulations prepared according to this invention can be present in the range of 0.1 to 50%, preferably 0.2 to 20%, and more preferably 0.5 to 10%. A currently preferred level of Lipoid E80 is from about 1% to 15%, more preferably from about 2% to about 10%, and most preferably from 3 to 5%.

In a preferred aspect, a process is provided for the preparation of small particles containing fenofibrate and a phospholipid surface stabilizing substance which comprises the steps of (a) mixing at high shear an admixture of the poorly water soluble drug and a phospholipid substance in an aqueous carrier in the absence of an organic solvent and optionally in the presence of one or more than one surface active substances within a first temperature range at or above the melting point of the drug to form a heated suspension containing the drug, then (b) homogenizing the heated suspension in a first pressure range and within the first temperature range to form a heated homogenate containing the drug, then (c) cooling the heated homogenate to a second temperature range below the melting temperature of the drug to form a transiently stable cooled homogenate containing the drug, then (d) applying a particle stabilizing energetic process to the cooled homogenate within a second temperature range and in a second pressure range to form a cooled dispersion of stabilized small particles containing the drug, and then (e) optionally drying the cooled dispersion to form dried small particles containing the drug.

In a specific aspect, the present invention is directed to a composition and a process for the preparation of microparticles of fenofibrate, which small particles are used to prepare an orally administered pharmaceutical composition comprising the microparticles of solid fenofibrate that are stabilized by a phospholipid surface active substance, wherein the microparticles are prepared in the presence of the phospholipid surface active substance, and wherein a therapeutically effective amount of the composition provides a quantity of fenofibrate to a fasted human patient in need of treatment by fenofibrate that is greater than 80% of the quantity of fenofibrate provided by the amount to the patient when fed at least 1000 calories 50% of which are from fat.

The process comprises the steps of (a) mixing at high shear an admixture of the poorly water soluble drug fenofibrate and a phospholipid substance in an aqueous carrier in the absence of an organic solvent and optionally in the presence of one or more than one surface active substances within a first temperature range at or above the melting point of the drug to form a heated suspension containing the drug, then (b) homogenizing the heated suspension in a first pressure range and within the first temperature range to form a heated homogenate containing the drug, then (c) cooling the heated homogenate to a second temperature range below the melting temperature of the drug to form a transiently stable cooled homogenate containing the drug, then (d) applying a particle stabilizing energetic process to the cooled homogenate within a second temperature range and in a second pressure range to form a cooled dispersion of stabilized small particles containing the drug, and then (e) optionally drying the cooled dispersion to form dried small particles containing the drug.

An admixture of a poorly water soluble drug and a surface active substance such as a phospholipid substance can be prepared by adding a surface active substance and the poorly water soluble drug to an aqueous carrier and then mixing at high shear, for example for up to 30 minutes at a shear rate of up to 10,000 rpm. As an example, an admixture of fenofibrate and a phospholipid substance can be prepared by adding a phospholipid substance and fenofibrate to an aqueous carrier and then mixing at high shear for up to 30 minutes at a shear rate of up to 10,000 rpm. Preferably the drug used to form the admixture is in the form of a powder or small crystals or small pieces that are less than about 5 mm in diameter to facilitate mixing. Larger sized crystals or masses of drug can be milled to about 5 mm or smaller before forming the admixture of used in this invention to facilitate mixing.

Suitable aqueous carriers include water, sterile water, water for injection, and buffered water such as phosphate buffered water. The pH of the buffer can be in the range of from 4 to 10, preferably from 7 to 9, and most preferably from 7.5 to 8.5. A preferred aqueous carrier is 0.01 to 10 mM sodium phosphate buffer. The pH of the carrier is preferably established at room temperature before mixing with the phospholipid substance and the poorly water soluble drug and before heating to a first temperature. The pH may be adjusted by addition of an acid or base such as HCl or NaOH to a solution of a phosphate salt. Preferably the aqueous carrier contains no dissolved oxygen. A currently most preferred aqueous carrier is 10 mM phosphate buffer.

In one aspect, the aqueous carrier can initially be at a temperature between about 1° C. to about 100° C., preferably between 20° C. and 90° C., and more preferably between 20° C. and 50° C. This is particularly useful for fenofibrate. The aqueous carrier can be heated to the desired first temperature range before or after the addition of the admixture.

In another aspect, the aqueous carrier can be heated to a temperature higher than 100° C., for example superheated up to 275° C. In this case, the aqueous carrier can be contained in a closed vessel or apparatus at a pressure higher than ambient pressure. The superheated aqueous carrier and the admixture can be contained in a pressurized closed system such as a stainless steel vessel or bomb in which high speed shear can be applied. The vessel is preferably connected through suitable piping and values to a heated homogenization apparatus which further comprises a reservoir and optionally a return pipe that can carry homogenate from the homogenizer back to the vessel if used in a continuous or batch-wise mode. The vapor pressure of water at 100° C. is approximately 14.7 psi and it rises as the temperature is increased. For example, at 120° C. the vapor pressure of water is approximately 28.8 psi; at 140° C. it is approximately 52.4 psi; at 160° C. it is approximately 89.6 psi; at 180° C. it is approximately 145.4 psi; at 200° C. it is approximately 225.5 psi; at 220° C. it is approximately 337 psi; at 240° C. it is approximately 486 psi; at 260° C. it is approximately 680 psi; and at 275° C. it is approximately 863 psi. A closed system useful in this invention can safely contain the heated components of this invention at least at these and higher-pressures and temperatures and used to provide small particles of poorly water soluble drug according to this invention.

After the poorly water soluble drug and surface active substance such as fenofibrate and a phospholipid substance are added to the aqueous carrier, the admixture can then be heated if not already so, preferably in the absence of oxygen such as under a nitrogen or argon atmosphere, until the temperature rises to a first temperature range that is at or above the melting point of the drug. In the case of fenofibrate the admixture in the aqueous carrier can be heated to between 79° C. (the reported lowest melting point of fenofibrate) and 99° C., preferably between 79° C. and 95° C., and most preferably between 80° C. and 90° C. In general it is preferred that the temperature is at or up to about 20° C. above the melting point of the drug. Thus, the preferred first temperature range is in general from the melting point of the drug to about 20° C. above the melting point of the drug. The aqueous carrier can be heated to the first temperature range before or after the addition of the drug and the surface active substance. The admixture is maintained at the first temperature range while high shear mixing is applied. The admixture when thus prepared comprises a crude emulsion of melted drug and surface active substance in the heated aqueous carrier.

During the heating of the admixture, high shear mixing is applied. Suitable shear is derived for example from propeller-containing mixers, homogenizers, blenders, sonicators or other devices capable of producing a heated suspension. Suitable shear rates can range between 500 to 10,000 rpm, preferably 2,000 to 5,000 rpm. High shear mixing can be continued for up to 30 minutes or even longer if needed to form a heated suspension containing the drug. High shear mixing of the admixture when the temperature is below the melting point of the drug provides a suspension of the admixture in the aqueous carrier, and such suspension is useful as an antecedent to the heated suspension that is produced when the temperature is increased to or above the melting point of the drug. Continued application of high shear mixing or application of more vigorous or ultra-high shear mixing when the temperature is above the melting point of the drug can produce a heated homogenate of the admixture in the aqueous carrier. When the temperature is above the melting point of the drug, the heated suspension is a suspension of melted drug and surface active substance in the aqueous carrier. In one aspect, the heated suspension is an emulsion of melted drug and surface active substance in the aqueous carrier. High shear mixing and ultra-high shear mixing can be produced by the input of mechanical energy for example using a mechanical mixer or stirrer or mill configured with a mixing blade or propeller that can induce efficient mixing and particle size reduction through high shear turbulence, turbulent eddies, transfer of high fluid kinetic energy, high energy dissipation, pressure induced cavitation, and similar known mechanisms of homogenization.

In one aspect, devices useful in the preparation of a heated suspension of this invention can be employed in the preparation of the heated homogenate of this invention if sufficient energy is transferred to the particles of the heated suspension to produce a heated homogenate. In this case, heating of the admixture to form a heated suspension and then homogenization of the heated suspension to form a heated homogenate can be done as a continuous step combining step (a) and step (b) into a single step wherein a heated suspension is formed and then converted into a heated homogenate with out substantial change in apparatus or without substantial increase in energy applied to the heated admixture formulation.

As used herein, homogenization refers to the creation of a homogenate or uniform distribution of small particles containing drug in an aqueous carrier as a result of an energetic process being applied to an antecedent composition such as a mixture, admixture, blend, emulsion, suspension, dispersion or other composition of solids or solid particles or liquids or liquid particles or droplets comprising drug and one or more than one surface active substance in an aqueous carrier wherein the homogenate and the small particles produced are at least transiently stable toward phase separation into larger particles or droplets or non-uniform solid or liquid domains. Homogenization, particularly with respect to the formation of a heated suspension and a heated homogenate, can be achieved by input of mechanical energy such as by high shear mixing, ultra high shear mixing, high speed blending, microfluidization, and milling such as by dispersion milling, ball milling, attritor milling, vibrator milling, and media milling, or by application of sonic energy in the form of sonication. Preferably in the case of a mill being used in this process wherein the mill contains media or grinding media, such media is removed in a filtration or other suitable separation process to provide homogenized compositions of this invention. Homogenization is preferably achieved by passing an antecedent composition under high pressure, for example under more than 1000 psi, through a tiny orifice which can result in a decrease in the average diameter and an increase in the number and surface area of particles or droplets in the antecedent composition and produce small particles. A preferred homogenization method comprises passing an antecedent composition under high pressure through a tiny orifice and includes microfluidization, particularly with respect to homogenization to prepare a cooled dispersion of this invention.

The drug can be added to the aqueous carrier as a solid. Preferably for example the drug such as fenofibrate can be added in the form of particles ranging in size up to about 10 mm such as milled or micronized particles or powders. Milled particles can be obtained for example by air jet milling of bulk powdered or crystalline fenofibrate. The drug can also be added to the aqueous carrier as a molten material, i.e., heated at or above its melting point, preferably at the melting point of the drug to about 20° C. above the melting point of the drug but at a temperature less than its decomposition point. For fenofibrate the preferred temperature can be from about 80° C., the melting point of the drug, to about 100° C. although temperatures up to the decomposition point of the drug are also suitable.

The concentration of the surface active substance in the aqueous carrier can vary between 0.1% w/w and 90% w/w, preferably between 0.1% w/w and 50% w/w, and more preferably between 0.2% and 20%, and most preferably between 0.5% to 10% w/w. The concentration of the drug such as fenofibrate in the aqueous carrier can vary between 0.1% w/w and 90% w/w, preferably between 0.5% w/w and 50% w/w, and more preferably between 1% and 20% w/w. For example, in one aspect a currently preferred composition comprises 3% to 10% of a phospholipid substance as a surface active substance and 10% of the poorly water soluble drug fenofibrate in 10 mM phosphate buffer at pH 8 as an aqueous carrier.

The surface active substance can be added to the aqueous carrier at any temperature below its decomposition point. When used as a mixture of surface active substances, the individual components can be added separately to the aqueous carrier or combined as mixtures before addition. The surface active substance can be added together with the drug, for example with fenofibrate or separately to the aqueous carrier.

The admixture of the drug, for example fenofibrate, and a surface active substance such as a phospholipid substance in an aqueous carrier is heated to a first temperature range during the application of a high shear mixing to produce a heated suspension containing the drug.

The heated suspension containing the drug is then homogenized at the first temperature range to form a heated homogenate. The first temperature range is maintained during this homogenization to ensure that the drug is maintained in a molten state. For fenofibrate, the first temperature range is preferably from 79° C. to 100° C. and more preferably from 80° C. to 100° C. provided that fenofibrate remains molten.

Homogenization of the heated suspension containing the drug can be carried out in equipment suitable for that process. Useful equipment includes commercially available high pressure homogenization equipment such as APV Gaulin M15, Avestin Emulsiflex C5 or C50, and MFIC Microfluidizer M110EH and other commercially available microfluidizers and commercially available microfluidizers modified to accommodate heat exchangers and temperature monitoring devices and piping and valves to carry heated suspensions or emulsions. The microfluidizers can be heated to the first temperature range, for example by use of electrical resistance, heated air bath, or heated fluid bath such as a water or silicone oil bath heated to the first temperature range that is at or above the melting point of the drug.

Homogenization of the heated suspension containing the drug is done at a first pressure range in the homogenization chamber of a heated homogenization apparatus while the drug is maintained in its molten state. The first pressure range can be from 2,000 psi to 30,000 psi, preferably about 5,000 psi to 20,000 psi, and more preferably from about 3,000 psi to about 10,000 psi.

The heated suspension containing the drug can be processed into the homogenization chamber of the homogenization apparatus by gravity feed from a heated and optionally stirred reservoir or by aid of a pump, for example a peristaltic pump, from a reservoir heated to the first temperature range through the heated homogenization chamber of the heated homogenizer and thence into a heated receiving vessel heated to the first temperature range in such a manner as to ensure the entire fluid volume of the heated suspension is subjected to discrete homogenization resulting in a homogeneous suspension of heated submicron or micron molten particles. In one aspect of this invention, between each homogenization pass the processed heated suspension is returned batch-wise from the heated receiving vessel back into the heated reservoir such as by means of a pump or by pouring, and the heated homogenization step is repeated. In another aspect, the processed heated suspension is fed directly back into the heated reservoir in a continuous process. If the aqueous carrier is heated above 100° C., the system is contained as a closed system under pressure during the feeding of the admixture to the homogenization apparatus and during the return of the homogenized or partially or not-completely homogenized heated suspension to the heated reservoir. If the initial volume of the heated suspension before homogenization is defined as a volume pass, then the number of volume passes made through the homogenizer in this manner can range from one to about 20, preferably from one to ten, more preferably from 2 to 8, and most preferably from 4 to 7 to produce a heated homogenate that is initially at the first temperature range at or above the melting point of the drug. A preferred drug in this process is fenofibrate which has a preferred first temperature range of from 80° C. to about 95° C.

While it is not known with certainty, it is appreciated that forcing a drug and a surface active substance such as a phospholipid under conditions of elevated pressure and temperature through a microfluidizing chamber can cause transient gradients in temperature, the microfluidization process being exothermic and causing a rise in the temperature of the processed suspension of particles or emulsions during particle size reduction. While the transient rise in temperature is usually controlled by a temperature regulating device such as a heat exchanger, it is possible that transient concentration gradients of poorly water soluble drug and stabilizer are established or continue to exist in the rapidly moving non-equilibrium state of the microfluidizer. Water insoluble or poorly soluble components of the formulation (e.g., fenofibrate and phospholipid) may be forced into solution temporarily, perhaps at a molecular level thereby creating a supersaturated or molecularly distorted environment which if left undisturbed will subsequently achieve equilibrium again. It is postulated that transient concentration gradients may be established in the microfluidization process wherein molecules of drug and stabilizer are forced into an aqueous environment to give a transiently stable but novel composition and non-equilibrium condition.

We have found that this heated homogenate can be cooled to a transiently stable or metastable cooled homogenate. By metastable stable we mean that upon agitation or long-term standing the transiently stable particles of the cooled homogenate will convert to larger particles of crystallized or precipitated drug and can demonstrate phase separation of components of the homogenate from the aqueous carrier. For example, under these conditions fenofibrate forms a transiently stable or metastable cooled homogenate that on standing or application of manual agitation such as shaking or stirring produces larger crystals. However, we have surprisingly found that the lifetime of the transiently stable particles of the cooled homogenate can be moderately extended by control of cooling conditions. Additional prolonged stability of the small particles can be obtained and by subsequent homogenization at a second temperature range that is below the melting point of the drug. We have also found that the total number of homogenization volume passes used in the heated and cooled homogenization processes of this invention is substantially fewer than the number of volume passes needed to produce a comparable drug suspension starting from the powdered or micronized drug that was used to prepared the admixture in this invention but homogenized while the drug was maintained entirely in the solid state according to prior art methods.

In one aspect particle size of the heated homogenate can be measured using a laser light diffraction based instrument such as a Malvern Mastersizer Microplus and shown to be less than one micrometer.

If an attempt is made to collect the heated homogenate in a receiving vessel that is not preheated to the first temperature, a poorly water soluble drug such as fenofibrate immediately precipitates from the heated homogenate as a solid, and in the case of fenofibrate as crystals. This is very likely related to agitation of the transiently stable dispersion.

In the case of fenofibrate, microscopic examination of a heated homogenate shows it to be comprised of small and non-crystalline particles in suspension, but there is a tendency for fenofibrate to crystallize out on the microscope slide. This rapid crystallization is also seen if the heated homogenate is collected in a receiver at ambient temperature.

A transiently stable or metastable cooled homogenate can be obtained from a heated homogenate derived from an admixture of drug and a surface active substance such as a phospholipid substance in an aqueous carrier by rapidly cooling the heated homogenate under non-agitating conditions from a first temperature range at or above the melting temperature of the drug to a second temperature range below the melting point of the drug, preferably to the range of 1° C. to about 20° C. In some cases, depending on how readily the drug crystallizes, under non-stirred conditions the cooled homogenate can retain small non-crystalline particles very similar to those detected initially in the heated homogenate. Optionally, the heated homogenate can be held at the first temperature range that is above the melting point of the drug, for a holding time before the onset of cooling to the second temperature range. Agitation during the holding period above the melting point of the drug does not effect crystallization of the drug. However, agitation such as by stirring of the cooled homogenate can induce growth in particle size and crystallization and precipitation of drug.

In particular, in the case of fenofibrate we have found that a transiently stable or metastable cooled homogenate can be obtained from a heated homogenate derived from an admixture of fenofibrate and a phospholipid substance in an aqueous carrier by rapidly cooling the heated homogenate under non-agitating conditions from a first temperature range at or above the melting temperature of fenofibrate to a second temperature range below the melting point of fenofibrate, preferably to the range of 1° C. to about 20° C. Under non-stirred conditions the cooled homogenate retains small non-crystalline particles very similar to those detected initially in the heated homogenate. Optionally, the heated homogenate can be held at the first temperature range, for example at 80° C. to 90° C., for a holding time before the onset of cooling to the second temperature range. Agitation during the holding period does not effect crystallization of the fenofibrate.

To determine a minimum holding time at 80 to 90° C. before the induction of cooling for a fenofibrate-containing heated homogenate, the holding time was varied at 15 minute intervals from 0 to 60 minutes and a cooling period in a bath held at 5° C. was kept constant at 30 minutes after the onset of cooling. In these experiments we find that particle mean diameters of the cooled homogenate are similar under all conditions studied. Thus, samples of freshly prepared heated homogenate can be held at a first temperature range for a holding period or they can be immediately cooled to a second temperature range after completion of the first homogenization step.

A number of cooling methods can be applied to the heated homogenate containing a poorly water soluble drug to cool it from the first temperature range at or above the melting point of the drug to a temperature below the melting point of the drug to form a cooled homogenate. Examples of several methods are listed and illustrated with respect to fenofibrate as follows.

Method 1: slow cooling in ambient air optionally in a closed vessel that excludes oxygen and air by allowing the heated homogenate to stand unagitated and to cool from above the melting point of the drug to ambient room temperature;

Method 2: slow unagitated cooling from above the melting point of the drug which for fenofibrate is about 85° C. in a water bath at ambient temperature which is approximately 15° C. to 20° C;

Method 3: slow stepwise cooling at 1 degree Centigrade per minute in a stirred oil bath from above the melting point of the drug to ambient temperature;

Method 4: slow stepwise cooling from above the melting point of the drug to about 20° C. below the melting point of the drug which for fenofibrate is from about 85° C. down to 65° C., followed by cooling to 4° C. in an isothermally cooled 4° C. water bath;

Method 5: fast cooling in an isothermally cooled 4° C. water bath;

Method 6: slow stepwise cooling from above the melting point of the drug to about 40° C. below the melting point of the drug which for fenofibrate is from about 85° C. to about 40° C. at the rate of 1 Centigrade degree per minute.

For cooling from temperatures initially above 100° C. the heated homogenate is maintained in a pressurized vessel. After cooling, the pressure can then be optionally adjusted to ambient without agitation of the contents of the vessel typically by means of a valve that permits pressure equalization to ambient pressure conditions. Preferably an inert atmosphere such as a nitrogen or argon atmosphere is maintained in contact with the formulations of this invention.

The effect of stirring during the cooling phase was examined for fenofibrate as an example. In some studies, samples were left unagitated while others were stirred magnetically at 250 rpm using Teflon-coated magnetic stirring bars during cooling methods. Additionally, in some experiments, heated homogenate was diluted ten fold with additional aqueous carrier that had been heated to the first temperature, the diluted heated homogenate was then swirled to evenly distribute the added aqueous carrier, and then the diluted heated homogenate was cooled.

Particle size determinations were carried out using a Malvern Microplus Mastersizer. Samples were examined at two to three hours after the initiation of cooling. Results are reported as volume weighted averages or D(4,3). Samples were also examined microscopically under bright polarized light using both in-phase and out-of-phase modes. In-phase light allowed determination of the primary particle size and the detection of aggregates. Out-of-phase examination gave an indication of the amount of crystals formed in the composition. Morphologically small crystalline particles of fenofibrate were easily distinguished from large fenofibrate crystals.

When 3% Lipoid E80 (also sometimes referred to as E80 herein below) was used as a phospholipid substance in a single pass homogenization preparation of a heated homogenate containing 10% fenofibrate, little difference was observed in the particle characteristics when cooled by either method 1 or 2 (average particle size at 3 hours was 2.42 and 2.96 micrometers, respectively). The particles were initially non-crystalline, spherical and submicron but crystals appeared within 3 hours. In contrast, when 3% Lipoid E80 was used as a phospholipid substance in a two pass homogenization preparation of a heated homogenate containing 10% fenofibrate, a smaller particle size was unexpectedly observed when a sample was cooled by method 1 versus when a sample was cooled by method 2 (0.56 and 1.64 micrometers, respectively after 3 hours of cooling). This difference was different from that seen in heated homogenates prepared with saturated lipids such as phospholipon 100H (also sometimes referred to as 100H herein below) and phospholipon 90H (also sometimes referred to as 90H herein below) when processed for two passes. In these formulations, the particle size at 2 to 3 hours after initiation of cooling was significantly higher than that seen using Lipoid E80. For heated homogenates prepared using 3% phospholipon 100H in two passes and cooled for 3 hours according to methods 1 and 2, the average particle sizes were 14.72 and 10.31 micrometers, respectively. For heated homogenates prepared using 3% phospholipon 90H in two passes and cooled for 2 hours according to methods 1 and 2, the average particle sizes were 6.07 and 5.23 micrometers, respectively. Microscopically the cooled homogenates containing phospholipon 100H and phospholipon 90H consisted of particle aggregates with crystals appearing over time. Aggregates were not typically seen in Lipoid E80 formulations but crystal growth occurred over time.

It was unexpectedly found that increasing the cooling rate in the absence of agitation produced cooled homogenates that maintained small particles containing the poorly water soluble drug fenofibrate to a greater degree than those produced by slow cooling methods. This was especially true when Lipoid E80 was used as the phospholipid substance. For example, when a sample of heated homogenate prepared from 3% Lipoid E80 as the surface active substance and 10% fenofibrate in two homogenization passes was cooled by method 5 (fast cooling) and compared to a cooled sample of heated homogenate of the same composition cooled according to methods 1 or 2 (slow cooling), the particle size at 3 hours for fast cooling was 0.63 micrometers versus 0.76 micrometers for slow cooling.

For non-stirred samples, minimal particle size increases can be observed in all cooling methods while under stirred conditions substantial crystallization or precipitation or agglomeration of poorly water soluble drug can be observed. For example, for non-stirred samples containing fenofibrate, minimal particle size increases were observed in all cooling methods. In contrast, under stirred conditions substantial crystallization of fenofibrate was observed for all cooling methods. For samples cooled in a slow step process, crystal growth occurred at temperatures lower than about 20° C. below the melting point of the drug, i.e., for fenofibrate below about 60° C.

It can be seen that energy imparted to the cooled homogenate by mechanical stirring for example using a stirring bar or spatula is not sufficient to impart stability to the particles of the cooled homogenate. To be effective, a particle stabilizing energetic process must impart sufficient energy to the particles of the cooled homogenate to convert them from a transiently stable homogenate into a longer lived dispersion of particles. Otherwise, undesirably large particles will be produced from the transiently stable cooled homogenate. Preferred particle stabilizing energetic processes include sonication and homogenization. A most preferred particle stabilizing energetic process is homogenization. It is believed that enough energy must be applied to the particles to modify some aspect of the particle composition which, while currently unknown, may be related to further reduction in particle size in the presence of a surface active substance or reorganization of drug and/or surface active substance molecules at or on the surface of the particle, or other phenomena.

Oral formulations of fenofibrate microparticles stabilized by phospholipid surface active substance and prepared by homogenization or microfluidization or hot melt homogenization or sonication provide unexpected reduction in food effect on the uptake of fenofibrate between fasted and fed conditions.

Diluting the heated homogenate ten fold with additional heated aqueous carrier was found unexpectedly to have a beneficial effect on the size of particles when cooled. Results for fenofibrate as an example are displayed in Table 2. Attention is drawn to the bottom two rows of Table 2 which show that the particle size of diluted suspension of fenofibrate is smaller than that of undiluted suspension.

TABLE 2

Effect of dilution with aqueous carrier on cooled particle sizes in micrometers of heated homogenate containing 10% fenofibrate and 3% phospholipid

| Phospholipid (one pass) | E80 | E80 | 100H | 100H | 90H | 90H |
| --- | --- | --- | --- | --- | --- | --- |
| Cooling method (time of cooling) | 1 (3 h) | 2 (3 h) | 1 (3 h) | 2 (3 h) | 1 (2 h) | 2 (2 h) |
| Undiluted average particle size | 2.42 | 2.96 | 11.46 | 9.71 | 4.83 | 4.12 |
| Diluted average particle size | 1.84 | 1.69 | 3.29 | 3.77 | 2.17 | 2.73 |

Cooled homogenate having particle size of less than 1 micrometer can usually be achieved by subjecting the heated homogenate containing melted drug to multiple homogenization passes prior to rapid cooling. The effect of multiple homogenization is to produce smaller particles, but the size reducing effect is non-linear and shows decreasing rates of return, i.e., the average particle size decreases non-linearly with an increasing number of passes.

In the case of fenofibrate, it was also found that increasing the number of heated homogenization passes from one to two followed by cooling produced a cooled homogenate with smaller particle size with Lipoid E80 but not with Phospholipon 100H or Phospholipon 90H. For example, at 3 hours after cooling, a cooled homogenate sample containing fenofibrate prepared according to method 1 had a particle size of 0.56 micrometers when the antecedent heated homogenate had been subjected to two passes of homogenization compared to a particle size of 2.42 micrometers when the antecedent heated homogenate had been subjected to one homogenization pass. When a heated homogenate had been subjected to 10 homogenization passes, the cooled homogenate had a particle size of 0.29 micrometers. It was generally found that cooled homogenate having particle size of about 0.3 micrometers could be achieved from heated homogenate that had been subjected to at least 5 homogenization passes. Additional homogenization produced smaller particles, but at decreasing rates per volume pass. For examples, particles as small as 0.05 micrometers can be achieved under homogenization conditions. Results for one and two homogenization volume passes as a function of phospholipid are displayed in Table 3.

TABLE 3

Difference between one and two heated homogenization passes on cooled particle sizes in micrometers of heated homogenates containing 10% fenofibrate and 3% phospholipid

| Phospholipid (no. of passes) | E80 | E80 | 100H | 100H | 90H | 90H |
|---|---|---|---|---|---|---|
| Cooling method | 1 | 2 | 1 | 2 | 1 | 2 |
| (time of cooling) | (3 h) | (3 h) | (3 h) | (3 h) | (2 h) | (2 h) |
| One pass average particle size | 2.42 | 2.96 | 11.46 | 9.71 | 4.83 | 4.12 |
| Two pass average particle size | 0.56 | 1.64 | 14.72 | 10.31 | 6.07 | 5.23 |

We have also found that the pass dependent particle size of the cooled homogenate can be a function of the ratio of the concentration of surface active substance to drug. For example, a heated homogenate prepared using 3% Lipoid E80 as the surface active substance and 10% fenofibrate as the drug and subjected to 10 homogenization passes produced a cooled homogenate by method 6 that had a particle size of 0.35 micrometers while a heated homogenate prepared using 10% Lipoid E80 as the surface active substance and 10% fenofibrate as the drug and subjected to 10 homogenization passes produced a cooled homogenate by method 6 that had a particle size of 1.3 micrometers.

Furthermore, when a heated homogenate was prepared using 3% Phospholipon 100H as the surface active substance and 10% fenofibrate as the drug, subjected to 10 homogenization passes and cooled, a cooled homogenate was produced by method 5 that had a particle size of 1.45 micrometers. In comparison, when a heated homogenate was prepared using 3% Lipoid E80 as the surface active substance and 10% fenofibrate as the drug, subjected to 10 homogenization passes and cooled, a cooled homogenate was produced that had a particle size of 1.3 micrometers.

Fast cooling of heated homogenates in a 4° C. bath under non-stirred conditions produces cooled homogenates with minimum change in morphology and particle size from that observed in the heated homogenates prior to cooling. For example, we have discovered that fast cooling of heated homogenates containing a phospholipid as the surface active substance and fenofibrate as the drug in a 4° C. bath under non-stirred conditions produced non-crystalline cooled homogenates with minimum change in morphology and particle size from that observed in the heated homogenates prior to cooling. When samples of heated homogenate were held at 80° C. for up to one hour and then cooled to form cooled homogenates that were held for 30 minutes at 5° C., no differences in particle size could be detected as a function of the time the heated homogenate was held at 80° C. before cooling. For optimum processing speed, freshly prepared samples of heated homogenate can be cooled from the first temperature range to a second temperature range immediately after an adequate number of homogenization passes such as five passes of heated homogenization to provide cooled homogenates. However, cooled homogenates thus prepared appear to be transiently stable or metastable toward formation of crystals of drug that can grow larger and precipitate from the suspension of the cooled homogenate if allowed to stand. The formation of larger particles and crystals is enhanced if the cooled homogenate is disturbed such as by stirring or shaking.

Preferably, the average particle size of the microparticles of fenofibrate stabilized with phospholipid is less than 10 microns, more preferably less than 5 microns, even more preferably less than 4 microns, yet even more preferably less than 3 microns, yet even more preferably less than 2 microns, and most preferably less than 1 micron. Microparticles that are less than about 0.5 microns are especially preferred.

In another aspect of this invention, bulking agents or bulking agent excipients can be added as solids or in solutions of aqueous carrier to the admixture of drug and a surface active substance in an aqueous carrier in the process of this invention.

A bulking agent is herein defined as compound useful in assisting redispersion of dried small particles back into a suspension such as an aqueous suspension. Suitable bulking agents include hydroxyl-containing, hydrophilic, relatively low molecular weight (less than 50,000) compounds such as monosaccharides, disaccharides, trisaccharides, sucrose, lactose, mannitol, sorbitol, trehalose, glycerol, dextrose, fructose, sugars, pentoses, hexoses, xylitol, and combinations thereof. Bulking agents are useful as protectants in a drying process such as cryoprotectants in a lyophilization process or as additives in a spray drying process or an evaporation process, preventing or substantially reducing particle fusion, combination, suspension degradation and agglomeration during drying, and assisting in the resuspension of particles from a dried state. Dry small particles containing a poorly water soluble drug can be produced for example as a lyophilizate which is a solid produced from a cooled dispersion of particles by the process of freezing the aqueous carrier to a solid comprising a dispersion in ice and then removing the water by subliming the ice under reduced pressure. Bulking agents can also reduce or depress the freezing point of aqueous compositions in which they are dissolved or partially dissolved.

Bulking agents can be added in amounts from 0.1% to about 50% w/w or more depending on the intended us. Additional amounts of bulking agents can be added to the phospholipid-stabilized microparticles after they have been prepared as a suspension, for example prior to a drying step such as a spray drying step or a lyophilization step, or after they have been dried or substantially dried. Mixing of bulking agents to dried or substantially dried microparticles can be done by mixing the ingredients or by adding one or more bulking agents to the microparticles or vice versa and subsequently blending the ingredients. Alternatively, the microparticles can be resuspended in a liquid or fluid such as an aqueous fluid and admixed with bulking agents as solutions, suspensions, or as dried substances, and the liquid or fluid can be subsequently removed. Depending on the intended use and ultimate formulation and dosage form, bulking agents such as monosaccharides, disaccharides, trisaccharides, sucrose, lactose, mannitol, sorbitol, trehalose, glycerol, dextrose, fructose, sugars, pentoses, hexoses, xylitol, and combinations thereof can be added in amounts varying from about 0.1% up to their solubility limits. A preferred range of these ingredients is such to provide from about 1% to about 90% of a tablet or capsule dosage form. A preferred range for the active ingredient, a fibrate such as fenofibrate in a tablet form 10% to about 90% by weight of the tablet, with a more preferred range being from about 15% to about 60%.

In yet another aspect of this invention, the phospholipid-stabilized microparticles can be sprayed onto the surface of a bulking agent, for example if the bulking agent is in the form of a particle or bead, a suspension of phospholipid-stabilized microparticles optionally containing dissolved or suspended bulking agent can be spray coated onto the surface of the bulking agent particle or bead to create a layer and optionally a multilayer derived from repetitive spray coating.

In a preferred embodiment of this invention, a suspension comprising microparticles of fenofibrate, which microparticles are stabilized with a one or more surface active agent wherein at least one surface active agent is a phospholipid, is sprayed onto the surface of a bulking agent, which bulking agent is in the form of support such as a bead or powder or crystal of a pharmaceutically acceptable excipient. A preferred method of spray coating is fluid bed drying such as top spray fluid bed drying or fluid bed granulation or bottom spray fluid bed drying. The suspension can contain one or more added excipients or bulking agents which can be dissolved or partially dissolved or suspended or partially dissolved and suspended therein. The suspension can be spray coated or spray dried onto the surface of a support using a fluid bed dryer such as, for example, an Aeromatic TS-5, a Glatt Fluid Bed Dryer, Model WSG-GPCG-5, a Glatt GPCG-5, a Glatt Fluid Bed Spray Granulator Dryer, Model WSG 15, a Glatt Fluid Bed Drier, Model WSG 60, a Niro Aeromatic Stainless Steel Fluid Bed Dryer, Model T-7, an Aeromatic Fielder Fluid Bed Spray Dryer, Mdl S6, a Niro 30, a Glatt Powder Coater/Granulator/Dryer, Model GPCG-5 or other commercially available fluid bed drying and granulating equipment.

A preferred suspension of fenofibrate according to this invention can be prepared from a pre-mix comprising a buffer, an aqueous medium, fenofibrate, and a phospholipid or mixture of phospholipid and one or more additional surface active agent and optionally one or more pharmaceutically acceptable excipient or bulking agent. While the suspension can be prepared by a process that reduces the size of the fenofibrate from its form in the premix which may be as crystals of size preferably from about 10 micrometers to about 1 millimeter or even larger in size in the premix, a preferred method to prepare the suspension comprises heating the premix above the melting point of the fenofibrate, for example to about 85° C. to about 99° C., homogenizing the melted fenofibrate and other components of the premix, for example using a microfluidizer, which can be operated at from about 1000 to 8000 psig, and preferably from about 3000 to 5000 psig. Microfluidization of the premix can be done in a continuous mode, for example with three and or more microfluidizer size reduction chambers linked in series and heated to maintain the fenofibrate in a melted state, or it can be done in batch mode wherein the fenofibrate and other premix materials are passed through a microfluidization chamber and recycled by heated piping back to the inlet chamber of the microfluidizer. Preferably, the melted fenofibrate is passed at least three times through a microfluidization chamber to achieve a desired molten suspension. The suspension of melted fenofibrate particles thus produced is then rapidly cooled below the melting point of fenofibrate, preferably to about 5° C. to about 15° C., and subjected to an energy stabilizing step such as a microfluidization at about 18000 psig to about 4000 psig for about 4 to 10 volume passes with continuous cooling to about 5° C. to about 15° C. A preferred mean particle size of the phosholipid-stabilized fenofibrate in the suspension thus produced is from about 0.5 micrometers to about 1.5 micrometers, more preferably from about 0.5 micrometers to about 1 micrometer.

A preferred suspension of fenofibrate can be prepared from a pre-mix comprising a buffer such as a phosphate buffer such as sodium phosphate. The buffer can be dissolved to form a solution in an aqueous medium such as water, in an aqueous solution, an aqueous suspension, or mixture of an aqueous solution or suspension with a solid or insoluble excipient. The buffer can be at a concentration in the range of about 1 mM to about 50 mM, preferably at a concentration of about 2 mM to about 20 mM, and more preferably from about 2 mM to about 15 mM. An especially preferred concentration is from about 2 mM to about 10 mM and a preferred buffer is sodium phosphate in water. The pH of the buffered aqueous medium in the premix should preferably be in the range from about 7 to about 8.5, and more preferably in the range from about pH 7.8 to about 8.2.

A preferred suspension of fenofibrate can be prepared from a pre-mix comprising a phospholipid such a phospholipid from an egg or plant origin, preferably in purified form, such as chicken egg phospholipid, for example Lipoid E80, or other purified egg phospholipid. The premix can contain about 0.1% w/w to about 10% w/w of phospholipid, preferably from about 0.5% w/w to about 6% w/w, and more preferably from about 1% w/w to about 5% w/w of phospholipid. Useful amounts include 1 and ⅔ (i.e., 1.67) % w/w and 3⅓ (i.e., 3.33) % w/w.

In one aspect, egg phospholipid useful in the pre-mix to form a suspension of phospholipid comprises phosphatidyl choline. Phosphatidyl choline can be present in an amount from about 50% to about 100% of the total weight of phospholipid in the suspension, preferably from about 75% to about 98% of the total weight of phospholipid in the suspension, more preferably from about 80% to about 95% of the total weight of phospholipid in the suspension, and more preferably from about 85% to 90% of the total weight of phospholipid in the suspension.

In one aspect, egg phospholipid useful in the pre-mix to form a suspension of phospholipid comprises phosphatidyl choline. Phosphatidyl choline can be present in an amount up to 20% of the total weight of phospholipid in the suspension, preferably in a range from about 0.1% to about 15% of the total weight of phospholipid in the suspension, and more preferably from about 1% to about 10% of the total weight of phospholipid in the suspension.

In one aspect, egg phospholipid useful in the pre-mix to form a suspension of phospholipid comprises sphingomyelin. Sphingomyelin can be present in an amount up to 5% of the total weight of phospholipid in the suspension, preferably in a range from about 0.1% to about 4% of the total weight of phospholipid in the suspension, and more preferably from about 1% to about 3% of the total weight of phospholipid in the suspension.

In one aspect, egg phospholipid useful in the pre-mix to form a suspension of phospholipid comprises lysophospholipid. Lysophospholipid can be present in an amount up to 5% of the total weight of phospholipid in the suspension, preferably in a range from about 0.1% to about 4% of the total weight of phospholipid in the suspension, and more preferably from about 0.5% to about 3% of the total weight of phospholipid in the suspension.

In one aspect, egg phospholipid useful in the pre-mix to form a suspension of phospholipid is mixed with additional lipid components such as one or more pharmaceutically acceptable triglycerides each of which is a glycerol triester of one or a mixture of C8 to C20 saturated or unsaturated fatty acids, one or more pharmaceutically acceptable diglycerides each of which is a glycerol diester of one or a mixture of C8 to C20 saturated or unsaturated fatty acids, one or more pharmaceutically acceptable monoglycerides each of which is a glycerol monoester of a C8 to C20 saturated or unsaturated fatty acid, a C8 to C20 saturated or unsaturated non-esterified fatty acid, a C8 to C20 saturated or unsaturated fatty acid esterified with ethanol, cholesterol, alpha-tocopherol such as a mixture of D and L forms or a pure D or a pure L form or an acetate ester of alpha-tocopherol, and combinations thereof. The amount of additional lipid component can be up to about 10% of the total weight of phospholipid used in the suspension, preferably from 0.01% to about 10% of the total weight of phospholipid in the suspension, and more preferably from about 0.01% to about 5% of the total weight of phospholipid in the suspension, and more preferably from about 0.01% to about 3% of the total weight of phospholipid in the suspension.

To the cooled suspension of fenofibrate can be added, with stirring or mixing such as with a high-speed or high-speed propeller mixer or stirrer such as a Barnant propeller mixer, one or more bulking agents.

In one aspect, a preferred bulking agent that is added to the suspension is selected from the group consisting of maltodextrin, mannitol, sucrose, trehalose, lactose, a carboxymethylcellulose such as sodium carboxymethylcellulose, and combinations thereof.

In one aspect, a preferred bulking agent that is added to the suspension is maltodextrin such as, for example, commercially available maltodextrin known as Maltrin M180, Maltrin M100, Maltrin M040, and the like.

In one aspect, a preferred bulking agent that is added to the suspension is mannitol.

In one aspect, a preferred bulking agent that is added to the suspension is a cellulosic additive such as a carboxymethylcellulose such as a sodium carboxymethylcellulose such as that available under the name CMC 7L2P.

In a preferred aspect, the suspension of phospholipid-stabilized fenofibrate microparticles containing added bulking agent is subjected to fluid bed drying onto a support. Preferably, the support is a pharmaceutically acceptable bulking agent material. A preferred support material for fluid bed drying according to this invention comprises beads or crystals such as beads or crystals of a sugar such as lactose. The fluid bed drying can be done by spraying the suspension containing fenofibrate microparticles onto the support by means of a top-spray technique, for example using a Glatt WSG-3 or equivalent fluid bed drying apparatus equipped with, for example, a 0.8 mm spray nozzle for top-spray.

In a preferred aspect, the inlet temperature is maintained at less than 50° C., preferably between about 30 and 35° C. The spray pressure is maintained between 0.5 and 4 barr, preferably between about 0.8 and 2 barr. The suspension flow rate is maintained at about 5 to 20 g/min, preferably at about 8 to 15 g/min. Air or an inert gas can be used in the drying process, preferably an inert gas such as nitrogen. The air or gas is preferably dry or bone dry or has a relative humidity of less than 15%.

In a preferred aspect, 750 g of lactose beads can be used as a support to be sprayed with a suspension of microparticles such that the spray-dried material from the suspension on the lactose contains about 250 to 350 mg of fenofibrate per gram of lactose. As a result of fluid bed drying of the suspension comprising phospholipid-stabilized fenofibrate microparticles, phosphate buffer salt, and added bulking agent, the composition produced comprises granules of lactose beads coated with bulking agent in the form of a matrix in which is embedded phospholipid not associated with the fenofibrate microparticles, phospholipid-stabilized fenofibrate microparticles, and phosphate buffer salt. The granules can be separate or can be agglomerated.

The support, e.g., beads, can be of any suitable size; for example, lactose beads, in an embodiment, can have a diameter of from 0.2 mm to 2 mm.

In one embodiment, the granules can be milled or ground to form a powder with a size smaller than 1.2 mm.

In another embodiment, the granules can be submitted to pressure such as by use of a roller or mill at temperatures below the melting point of the granule composition or components of the granule composition to produce fractured granules wherein a granule is cleaved or broken to expose a portion of the lactose bead or crystal support material that is not covered by the fenofibrate microparticles, the phospholipid, and the phosphate buffer salt in the matrix material. There is thus produced a granule comprising a support material in the core of the granule, the surface of which core material is covered from about 90% to about 20%, in embodiments about 80% to about 50%, by area, with a fluid bed dried composition comprising bulking agent as a matrix in which is embedded phospholipid, phospholipid-stabilized microparticles of fenofibrate, and phosphate buffer salt, and which core contains an exposed surface area comprising about 10% to about 80% of support substance that is not covered with a fluid bed dried composition comprising bulking agent as a matrix in which is embedded phospholipid, phospholipid-stabilized microparticles of fenofibrate, and phosphate buffer salt. Such exposed surface of a water soluble support such as lactose will be readily hydrated and dissolve when exposed to an aqueous medium together with the matrix bulking agent and buffer salt and liberate the phospholipid-coated microparticles at a rate that is 1.1 to 10 times, or even to 100 times, or even to 1000 times faster than the rate of release from a granule comprising a support that is completely coated with the fluid bed dried composition comprising bulking agent as a matrix in which is embedded phospholipid, phospholipid-stabilized microparticles of fenofibrate, and phosphate buffer salt at 20° C. or at 37° C.

In a preferred embodiment, the size distribution of granules coated with a fluid bed dried suspension matrix of fenofibrate microparticles comprise:

less than 1% w/w and preferably less than 0.1% w/w of granules in the range greater than 850 μm to 1 mm;

not more than 25% w/w and preferably less than 20% w/w of granules in the range from 600 μm to 850 μm;

not more than 70% w/w and preferably about 40% to 60% w/w of granules in the range from 425 μm to 600 μm;

not more than 40% w/w and preferably about 20% to 30% w/w of granules in the range from 75 µm to 425 µm; and not less than 0.5% w/w and preferably about 1-5% w/w of granules in the range from 75 µm to 1 µm.

The granules that are produced by fluid bed spray coating of support material comprise a support material in the core of each granule, the surface of which core material is covered in whole or in part as described above with a fluid bed dried composition comprising bulking agent as a matrix in which is embedded phospholipid, phospholipid-stabilized microparticles of fenofibrate, and phosphate buffer salt can be blended with additional excipients and tableting aids, for example by using a V-blender to mix solid materials. The resulting mixture can be formed into tablets or capsules as individual dosage forms. Tablets can be made using conventional tableting equipment. Tablets can be made using equipment such as an automated single station press, for example, a Cadmach tablet press model CMS-15, or a multiple station rotary press, for example, a multiple station rotary press available from Manesty or Korsch.

Examples of useful tableting excipients and tableting aids that can be blended with the fluid bed dried granules include pharmaceutically acceptable synthetic polymers such as polyvinylpyrrolidone (or PVP), crosslinked polyvinylpyrrolidone, crospovidone such as Kollidon-CL; croscarmellose; croscarmellose sodium such as Ac-di-Sol SD-711; mannitol in powder form, mannitol in crystalline form, mannitol in granular form such as Pearlitol 200 SD and Pearlitol 400 DC; lauryl sulfates such as sodium lauryl sulfate and dodecyl sulfates such as sodium dodecyl sulfate or SDS; silicon dioxide such as colloidal silicon dioxide or silica such as Cab-o-Sil M-5P; stearate salts such as magnesium stearate.

In a preferred tablet dosage form prepared from a fluid bed dried suspension of phospholipid-coated microparticles, each tablet comprises:

fenofibrate in the range of about 15% w/w to about 20% w/w of the tablet, preferably about 18% w/w to about 19.5% w/w of the tablet;

phospholipid such as egg lecithin in a range of about 1% w/w to about 8% w/w, preferably about 2% w/w to about 6% w/w of the tablet;

buffer salt such as sodium phosphate in the range of about 0.1% w/w to about 0.5% w/w, preferably from 0.1% w/w to about 0.2% w/w of the tablet;

a bulking agent that was added to the suspension before spray coating of the suspension, which bulking agent is preferably selected from the group consisting of maltodextrin in the range from about 7% w/w to about 20% w/w or more preferably from about 9% w/w to about 20% w/w of the tablet, and mannitol in the range of from about 7% w/w to about 20% w/w of the tablet;

a cellulosic additive such as a carboxymethylcellulose such as a sodium carboxymethylcellulose in the range of from about 3% w/w to about 8% w/w, preferably from about 4% w/w to about 6% w/w of the tablet;

a support material such as lactose beads or crystals on to which was sprayed by fluid bed drying a suspension comprising phospholipid-coated microparticles such as lactose beads in the range of about 12% w/w to 16% w/w, preferably about 14% w/w to about 15% w/w of the tablet; and tableting excipients including:

polyvinylpyrrolidone or crospovidone in the range of about 5% w/w to about 30% w/w, preferably in the range from about 6% w/w to about 26% w/w of the tablet;

croscarmellose sodium in the range of about 1% w/w to about 6% w/w, preferably in the range of about 2% w/w to about 5% w/w of the tablet;

mannitol in the range of about 3% w/w to about 30% w/w, preferably in the range from about 5% w/w to about 27% w/w of the tablet;

sodium dodecyl sulfate or SDS or SLS in the range of about 1% w/w to about 4% w/w, preferably in the range from about 2% w/w to about 3% w/w of the tablet;

silicon dioxide such as colloidal silicon dioxide in the range up to about 1% w/w, preferably from about 0.5% w/w to about 0.8% w/w of the tablet; and a stearate such as magnesium stearate in the range up to about 1% w/w, preferably from about 0.2% w/w to about 0.5% w/w of the tablet. Preferred bulking agents include trehalose, sucrose, sorbitol, and combinations thereof. Preferred levels of these bulking agents in the admixture range from about 1% to about 30% w/w, and more preferably from about 2% to about 25% w/w.

The phospholipid-stabilized microparticles that exhibit a substantial reduction in food effect as described in this invention can be employed in a number of dosage forms. Particularly useful are the dosage forms disclosed in WO 00/30616 the contents of which is hereby incorporated by reference.

Bulking agents can be added to the admixture, to the heated suspension, to the heated homogenate, to the cooled homogenate to the cooled dispersion, and to the dried particles. They can be added as solids or as liquids or as solutions in aqueous carrier.

The stability of cooled homogenate formulations with respect to the effect of addition of a bulking agent or a combination of bulking agents was examined. When bulking agents were added as solids or liquids to heated admixtures of fenofibrate and a phospholipid substance as a surface active substance in an aqueous carrier, then processed for example using 10 heated homogenization passes at 80° C. and subsequently cooled in a 4° C. water bath, particle size estimates suggested that with the exception of the bulking agent sucrose (10%), there was little increase in particle mean diameter measurements over a 2 h period. However microscopic observations revealed the presence of a significant number of large crystals after the cooling step. Addition of 2-fold hot buffer solution containing either nothing or bulking agents to the processed formulations caused a large increase in the mean particle diameter. This was attributed by microscopic examination to be due to particle aggregation together with large crystals also present.

When trehalose was added to an admixture of fenofibrate and a phospholipid substance in an aqueous carrier, on stirring crystals were detected indicating that trehalose did not stabilise these metastable formulations with respect to crystal formation and precipitation. PVP 17 and glycerol were added to heated homogenates, and in both cases crystal growth was observed microscopically under stirred conditions. When glycerol alone or glycerol and trehalose were added to the admixture and then homogenized, results from stirring experiments again showed that these formulations were unstable with extensive crystallization observed over time. Thus, adding bulking agents or PVP to either the admixture or to the heated homogenate does not result in stabilization of the metastable formulation under stirring conditions.

Whereas a cooled homogenate can be unstable with respect to agitation such as stirring or manual shaking, we have surprisingly found that a cooled homogenate can be transformed into a more stable cooled dispersion by application of a particle stabilizing energetic process applied at the second temperature range and in a second pressure range.

For example, although the aforementioned cooled homogenates of fenofibrate were found to be unstable with respect to agitation such as stirring or manual shaking that lead to the formation of crystals of fenofibrate, we have found that the cooled homogenate can be transformed into a more stable cooled dispersion by application of a particle stabilizing energetic process applied at the second temperature range and in a second pressure range.

Examples of suitable particle stabilizing energetic processes include homogenization, microfluidization, and sonication. Microfluidization is generally considered to be a method of homogenization. Microfluidization of fenofibrate in the presence of a phospholipid stabilizing agent produces a novel composition that when formulated into a suitable dosage form as a dried solid optionally in the presence of one or more excipients such as sucrose, sorbitol, trehalose, Tween 80, mannitol, other sugars and starch, and the like provides a novel oral dosage form of the drug which when taken by a fasting or a fed patient exhibits a differential uptake of the drug by the fasted patient of at least 80% of the AUC amount of drug taken up by a patient fed a high fat meal. The unexpected and sizable reduction in food effect on the uptake of drug by fasted and fed patients is useful in the prescription of the drug to a patient undergoing treatment in that the patient will receive comparable and therapeutically useful levels of the drug regardless of whether the patient is fed or fasted.

The mechanism of obviation of food effect in patient taking the dosage form of fibrate in this invention is not yet fully understood, but it can be postulated that the phospholipid is uniquely involved in several aspects that lead to this novel discovery. For example, the phospholipid is involved in the stabilization of the fibrate particles during their formation and manipulation during formation of the dosage form; the phospholipid is involved in the reconstitution and continued stabilization of the particles during disintegration of the oral dosage form in vivo; and the phospholipid is perhaps involved in a mechanism leading to dissolution of the particles in vivo and/or uptake of the drug into the blood, e.g., molecular association between phospholipid and drug and other in vivo substance in some sort of transport mechanism.

In one aspect, particles of a heated homogenate containing a poorly soluble drug can be non-crystalline while the cooled dispersion particles produced as a result of application of a particle stabilizing energetic process can be crystalline. While stirring can induce significant particle growth in a cooled homogenate, stirring does not induce significant particle growth in a cooled dispersion formed from the cooled homogenate. The cooled dispersion thus produced is more robust toward particle growth than the cooled homogenate. The particles of the cooled dispersion are preferably in the micron and submicron range. Depending on the number of stabilizing processing steps, i.e., volume passes, employed in the preparation of the cooled dispersion, the cooled dispersion can also comprise weakly associated aggregates of particles that can be readily broken up or dispersed or de-aggregated by stirring the dispersion. Preferably, an increase in the number of processing steps from 1 to a range of from 5 to 20, preferably from 10 to 20, can produce fewer and more easily dispersed aggregates. Formulation instability toward stirring can be increased as a result of the particle stabilizing energizing process.

Microscopically, in the case of fenofibrate as an example of a poorly soluble drug, heated homogenate particles are non-crystalline while cooled dispersion particles produced as a result of application of a particle stabilizing energetic process are crystalline. Importantly, while stirring can induce significant particle growth in a cooled homogenate, stirring does not induce significant particle growth in a cooled dispersion formed from the cooled homogenate. The cooled dispersion thus produced is more robust toward particle size growth than the cooled homogenate. One possible explanation is that the number of nucleation sites for formation of crystals of the poorly soluble drug is substantially increased by application of a particle stabilizing energetic process such as microfluidization in the presence of a surface active substance giving rise to stable small crystalline particles in the micron and submicron range.

A preferred particle stabilizing energetic process is microfluidization for example using a Microfluidix M110EH apparatus. Microfluidization can be accomplished using from 1 to 20 volume passes, preferably from 2 to 20 volume passes, more preferably from 5 to 20 volume passes, and most preferably from 10 to 20 volume passes. Microfluidization can be done in continuous mode or in batch mode. A preferred second temperature range is the second temperature range used for the preparation of the cooled homogenate and is preferably from 1° C. to 40° C., more preferably form 4° C. to 20° C. and most preferably from 4° C. to 15° C. A useful pressure range for the preparation of the cooled dispersion is a second pressure range, that is, from 2,000 to about 30,000 psi, preferably from 5,000 to about 20,000 psi, and most preferably from 5,000 to 18,000 psi.

Microscopically, in the case of fenofibrate as an example, the cooled dispersion is a suspension of crystalline fenofibrate particles. Depending directly on the number of stabilizing processing steps or volume passes employed in the preparation of the cooled dispersion, the cooled dispersion can also comprise weakly associated aggregates of crystalline fenofibrate particles that can be broken up or dispersed or de-aggregated by stirring the suspension.

FIG. 1 is an optical microscopic comparison of microfluidized fenofibrate with micronized fenofibrate and fenofibrate compositions prepared in the presence of starch. In FIG. 1(A), crystals of fenofibrate 20 and domains of starch 10 are large with respect to the 100 micrometer scale. In FIG. 1(B), encircled micronized fenofibrate 40 is seen to be non uniformly sized and dispersed and particles are entrained in starch domain 30. In FIG. 1(C), encircled microfluidized fenofibrate particles 40 that are stabilized with phospholipid are uniformly distributed in an average size smaller than micronized fenofibrate of FIG. 1(B).

A reduction in the cooled dispersion particle mean diameter can be achieved by increasing the number of volume passes during the cold homogenization step. For example, as shown in Table 4 for a formulation derived from an admixture of 3% Lipoid E80 as the surface active substance and 10% fenofibrate as a poorly water soluble drug processed first for 10 volume passes to form a heated homogenate containing the drug, cooled according to method 5 to form a transiently stable cooled homogenate containing the drug, and then microfluidized for 2 volume to 10 volume passes to form a cooled dispersion of small particles containing the drug, the observed mean diameter was 0.26 to 0.54 micrometers as a cooled homogenate prior to undergoing a particle stabilizing energizing process, 1.45 micrometers as a cooled dispersion when processed for 2 volume passes, and 0.9 micrometers when processed for 10 volume passes. Surprisingly, formulation instability toward stirring was dramatically increased as a result of the particle stabilizing energizing process. Without the additional particle stabilizing energizing process, the average particle size of the cooled homogenate increased by two orders of magnitude with stirring within 30 minutes. However, after application of the particle stabilizing energizing process, the average particle size did not increase substantially with stirring up to 24 hours. In addition, the average particle size of the cooled dispersion was smaller and remained smaller up to 5 days when the formulation was processed for 10 volume passes.

TABLE 4

Particle size changes of cooled homogenate and cooled dispersion From an admixture of 10% Fenofibrate, 3% Lipoid E80 as the surface active substance in 10 mM phosphate buffer at pH 8. Keeping temperature was 4° C.

|  | Time (minutes) | Average size not stirred (micrometers) | Average size stirred (micrometers) |
|---|---|---|---|
| Cooled homogenate (10 volume Passes) | 0 | 0.26 | 0.26 |
|  | 30 | 0.26 | 14.22 |
|  | 60 | 0.54 | 9.44 |
| Cooled dispersion (2 volume Passes) | 0 | 1.45 | 1.45 |
|  | 30 | 1.45 | 1.29 |
|  | 60 | 1.37 | 1.37 |
|  | 1440 | Not measured | 1.12 |
| Cooled dispersion (10 volume passes) | 0 | 0.87 | Not measured |
|  | 1140 | 0.93 | Not measured |
|  | 5700 | 0.97 | Not measured |

When egg lecithin Lipoin E80 was replaced with phospholipon H 100, the cooled homogenate particle size was higher after the 10 passes than with Lipoid E80 equivalent (2.3 micrometers versus 0.3 micrometers, respectively). In addition after processing to form a cooled dispersion of small particles containing the drug, a further relative increase in particle size of cooled dispersion was detected. This can be attributed to aggregation of the primary particles. For both the Lipoid E80 formulation and the phospholipon H 100 formulation, aggregate sizes could be decreased over time with stirring.

Scanning electron microscopic (SEM) analysis of cooled dispersions prepared originally from fenofibrate and a phospholipid as a surface active substance in the admixture and by 10 volume passes revealed them to exist as single crystalline particles each about 1 micron in mean diameter. Cooled dispersions are comparable to microfluidized formulations of phospholipid and fenofibrate that can be prepared by microfluidization below the melting point of fenofibrate such as according to IDD-P™ technology developed by RTP Pharma Inc. as described in U.S. Pat. No. 5,091,187 which is hereby incorporated by reference. However, to achieve such particle size reduction without first melting the drug can require substantially more volume passes of microfluidization, for example as many as 200 passes at ca. 18,000 psi.

In another aspect of this invention, more than one surface active substance can be used to prepare formulations according to this invention. At least one surface active substance is needed to prepare the initial admixture of this invention, and in one aspect can suffice in the preparation of subsequent heated suspensions, heated homogenates, cooled homogenates, cooled dispersions and dried particles prepared according to this invention. In another aspect, addition of more than one surface active substance can be made to the admixture, the heated suspension, the heated homogenate, the cooled homogenate, and the cooled dispersion of this invention. Such additions can be made at one individual step in the process or at more than one step in the process. For example, a second surface active agent can be added to the admixture or to the heated suspension, and additional amounts of the second surface active agent or a third surface active agent can be added to the cooled homogenate or to the cooled suspension or even to the dried small particles prepared according to this invention.

The total concentration of one or of more than one surface active substance added to the formulations prepared according to this invention can be in the range of 0.1 to 50%, preferably 0.2 to 20%, and more preferably 0.5 to 10%, w/w.

In another aspect of this invention, bulking agents can be added to the admixture, to the heated homogenate, to the cooled homogenate, and to the cooled dispersion. Bulking agents can be added as solids, as mixtures, as solutions in aqueous carrier, and in combinations of solids and solutions. Bulking agents can be added at the beginning or end of the steps leading to the formation of a heated homogenate, cooled homogenate, and cooled dispersion, and they can be added at more than one stage during the process. The amount of total bulking agents that can be added ranges from about 0.1% to about 50%, preferably from 1% to about 25%, and more preferably from about 2% to about 20%, w/w. Bulking agents can be added as individual agents at these levels or in combination such that the total amount of bulking agent resides within these levels.

Addition of a variety of bulking agents at different steps in the process of this invention does not produce a substantial increase the mean particle diameter of a cooled dispersion over a period of time such as over 24 hours. For example, when bulking agents sorbitol (5%) and sucrose (10%) were added to a 3% Lipoid E80 and 10% fenofibrate admixture and the formulation was processed for 10 passes to form a cooled homogenate and for 10 passes to form a cooled dispersion of small particles containing the drug, the particle size of the cooled dispersion (0.97 micrometers) was very similar in size to that of an analogous formulation composition (i.e., 0.91 micron) where the same bulking agents were added after the formation of the cooled dispersion.

Homogenization of the cooled homogenate containing the drug can be carried out in equipment suitable for that process. Useful equipment includes but is not limited to commercially available high pressure homogenization equipment such as APV Gaulin M15[AKM1], Avestin Emulsiflex C5 or C50, MFIC Microfluidizer M110EH, and other microfluidizers and homogenizers. Homogenization can also be carried out using high shear and ultra high shear mechanical mixers and mills and propeller-containing mixers than can impart sufficient turbulence or energy transfer to the particles to form stable small particles. The apparatus is cooled to maintain the cooled homogenate and cooled dispersion at the second temperature range. Cooling can be done by use of a cooled air bath, a cooled fluid bath such as a water or ice/water bath, or a suitable heat exchanger that is cooled and maintained at or below the second temperature range that is below the melting point of the drug.

In a final step of the process to prepare microparticulate fenofibrate, the cooled dispersion can be dried to provide dry small particles containing the poorly soluble drug. Drying can be done using a number of commonly known methods, for example by spray drying, lyophilization, and evaporation. Preferably one or more than one bulking agent is present in the formulation undergoing drying.

When drying is done by spray drying the cooled dispersion is feed into the spray dryer as a liquid, preferably at a temperature in the second temperature range and preferably as a dispersion comprising one or more than one bulking agent.

When drying is done by evaporation, the aqueous carrier of the cooled dispersion can be maintained as a liquid and water is removed under reduced pressure and with application of enough heat to keep at least some and preferably all of the aqueous carrier in the cooled dispersion that is drying in the liquid state until it is dried.

When drying is done by lyophilization, the aqueous carrier of the cooled dispersion is frozen and lyophilized under reduced pressure and application of heat to the frozen suspension to provide a lyophilizate comprising small particles containing poorly soluble drug. Freezing and lyophilization are preferably done in a conventional freeze dryer, for example, in a Virtis Corporation Unitop freeze dryer using conventional techniques. Lyophilization can be done on cooled dispersions added to trays or on cooled dispersions added to vials, for example in 2 mL or 10 mL vials. Bulking agents can be added to the formulation to facilitate reconstitution of the lyophilizate.

In the case of fenofibrate as an example, in a final step of the process, the cooled dispersion can be dried by freezing the aqueous carrier in the dispersion and lyophilizating the frozen dispersion under reduced pressure and by application of heat to provide a lyophilizate comprising small particles containing fenofibrate. Optionally, the cooled suspension can be spray dried to provide a dried powder of particles containing fenofibrate. Alternatively, the water in aqueous carrier of the cooled dispersion can be evaporated, for example under reduced pressure to provide dried small particles containing fenofibrate.

By small particles containing a poorly water soluble drug is meant particles in the range of 0.1 micron to 20 micrometers in average diameter containing a poorly water soluble drug, preferably in the range of 0.1 to 5 micrometers containing a poorly water soluble drug, and most preferably in the range of 0.1 to 2 micron containing a poorly water soluble drug.

By small particles containing fenofibrate is meant particles in the range of 0.1 micron to 20 micrometers in average diameter containing fenofibrate, preferably in the range of 0.1 to 5 micrometers containing fenofibrate, and most preferably in the range of 0.1 to 2 micron containing fenofibrate.

Addition of bulking agents such as sucrose and sorbitol either to the admixture before processing or to the cooled dispersion just prior to drying provides particle size suspensions on reconstitution similar in size to those of the antecedent cooled dispersion. Drying can be done by spray drying or preferably by lyophilization.

Addition of bulking agent such as trehalose either to the admixture before processing, to the heated homogenate, to the cooled homogenate, or to the cooled dispersion just prior to drying provides particle size suspensions on reconstitution that are similar in size to those of the antecedent cooled dispersion.

Samples of cooled homogenate can be dried for example by lyophilization with bulking agents and reconstituted in modified simulated gastric fluid (SGF) with gentle inversion immediately after lyophilization. The particle sizes of the dispersions on reconstitution can be similar to, i.e., the same or slightly larger than, those of the antecedent cooled homogenates. Microscopically, the reconstituted suspensions can exist primarily as single crystalline particles together with occasional aggregates. For example, a cooled dispersion prepared from an admixture of 3% Lipoid E80 as the surface active substance, 10% fenofibrate, 10% sucrose, and 5% sorbitol as an antecedent cooled dispersion has an average particle size of 0.96 micrometers. On reconstitution of the corresponding lyophilizate, the average particle size of the reconstituted suspension is 1.57 micrometers. For the compositionally equivalent formulation where the bulking agents are added to the cooled dispersion, mean particle diameters before and after lyophilization are 0.91 and 1.38 micrometers, respectively.

Other bulking agents, for example glycerol at 2%, sucrose at 5%, also yield dried particles that reconstitute easily and provide suspensions of single crystalline particles.

The period of stability of the particles of the cooled dispersion of stabilized small particles containing the drug can extend from the stability period of the transiently stable particles of the cooled homogenate up to several months. Stability of more than a year is also contemplated.

Formulations prepared by this invention may be dried into powders, which can be resuspended or filled into capsules or converted into granules or tablets with the addition of binders and other excipients known in the art of tablet making such as, for example, silica as a flow aid and magnesium stearate. A currently preferred capsule formulation for oral administration of phospholipid stabilized fenofibrate microparticles comprises fenofibrate (10% w/w) as microparticles prepared by microfluidization in 10 mM phosphate buffer with phospholipid Lipoid E80 (3% w/w), sucrose (10% w/w), and sorbitol (5% w/w). The suspension of microparticles prepared by microfluidization of these ingredients is dried by lyophilization to remove water and form a solid which is blended with colloidal silicon dioxide (up to 1% w/w) and magnesium stearate (up to 5% w/w). This blend is then filled into capsules or compressed into tablets for oral delivery. The amount of fenofibrate per unit oral dosage form such as per capsule or tablet can range from about 50 mg to about 300 mg, but is preferably 50 mg, 67 mg, 100 mg, 134 mg, 150 mg, 160 mg, 200 mg, 213 mg, 250 mg, and 300 mg. Useful dosage levels for tablets and capsules include in the high end of the range milligram levels that are divisible by three such as 150 mg (giving related lower dosage levels of 100 mg and 50 mg), 159 mg (giving related lower dosage levels of 106 mg and 53 mg), 156 mg (giving related lower dosage levels of 104 mg and 52 mg), 153 mg (giving related lower dosage levels of 102 mg and 51 mg). Multiples of this type have the advantage of assisting a physician to titrate a patient to a therapeutically acceptable level starting with a low dose of the fibrate and changing the dose in well defined increments until a desire result is achieved, such as a lowering of levels of cholesterol, low density lipoproteins, and other species outlined in Table 1. Additional currently preferred dosage levels contain 50 mg, 67 mg, 100 mg, 134 mg, 150 mg, 160 mg, 200 mg and 213 mg of fenofibrate as microparticles stabilized with phospholipid. Capsules and tablets for oral administration provide fenofibrate to a human patient in need of treatment by fenofibrate that is relatively independent of food effect. Thus, a patient in a fasted state will receive at least 80% of the dose of the drug that a patient in a fed state will receive by taking the same capsule or tablet dosage form (at the same level of drug per unit dosage form, i.e., at the same number of mg of drug per tablet or capsule given to the same patient when fasted as when fed). More preferably, a patient in a fasted state will receive at least 85% of the dose of the drug that a patient in a fed state will receive by taking the same capsule or tablet dosage form. Even more preferably, a patient in a fasted state will receive at least 87% of the dose of the drug that a patient in a fed state will receive by taking the same capsule or tablet dosage form.

The tablets containing the fibrate dosage form of this invention can be prepared by compression of solid particles in a bulking agent such as a sugar as described herein. Optionally, the tablets can be coated with a pharmaceutically acceptable coating material such as pharmaceutically acceptable polymer for example carboxymethyl cellulose, sodium carboxymethyl cellulose, povidone, PVP, polyethylene, PEG, shellac, cellulose acetate, CAP, polyvinyl acetate phthalate, PVAP, hydroxypropyl methyl cellulose phthalate, HPMCP, polymers of methacrylic acid and its esters, Eudragit polymers, methyl cellulose, MC, ethyl cellulose, EC, hydroxyethyl cellulose, HEC, methylhydroxyethyl cellulose, MHEC, hydroxypropyl cellulose, HPC, hydroxypropylmethyl cellulose, HPMC, and combinations thereof and at levels well known in the art of tablet coating. The coatings can be applied in pharmaceutically acceptable form which is well known in the art such as suspension coating, fluid coating, spray coating, Escaravage coating which is coating method for individual tablets using a solution of coating materials applied with a brush, film coating, preferably from a water based solution and optionally from a water-solvent such as water-ethanol based solution, and dried to form a dried film-coating. The added weight to the table can be from about 0.1% to about 20%, preferably from 1% to about 5%. The solutions used to coat the tablet dosage form can of course optionally contain mixtures of ingredients such as sugars, pharmaceutically acceptable plastisizers, antioxidants, pH modifiers such as carboxylic acids or carboxylate salts, vitamin E, beta-carotene, and the like. The coating can be applied in a single layer or optionally in several layers with each layer being the same composition or a different composition of ingredients.

Additional coating materials are commercially available from Colorcon Inc. of Westpoint, Pa. and from Berwind Pharmaceutical Services of Westpoint Pa. Additional coating materials particularly useful in this invention include Opagloss—a shellac based polymer coated from an organic solvent, Opadry$^R$ AMB—a PVA based polymer coated from an aqueous solvent, Opadry$^R$, and Opadry$^R$ II—a HPMC based coating material coated from an aqueous solvent such as water, each available from Colorcon Inc. Opadry$^R$ II is a blend of a combination of polymer and plasticizer and optional pigment and polysaccharides (which are carbohydrates). Coatings can be applied as a single coating or and a multi-player coating of two or more layers of which the first is a sub-coating or primary coating and the second or later coating is an overcoat of the subcoat or a topcoat. The coatings can have the same or different compositions of coating materials such as different polymer or polymers, different polysaccharides, different plastizisers, different pigments, and different amounts of residual water when dried.

Particles of drug provided according to this invention have bioavailability comparable to or better than similar sized particles prepared by alternate methods. This is illustrated graphically in FIG. 2 which compares the oral bioavailability of microparticles of fenofibrate prepared by microfluidization in the presence of a phospholipid stabilizing agent versus the oral bioavailability of micronized fenofibrate under fasting, low fat fed, and high fat fed conditions. In FIG. 2, part A, the fenofibrate in microfluidized phospholipid-stabilized microparticles (bar 2) is nearly twice as bioavailable as that in a micronized formulation (bar 1) in the fasted state. In FIG. 2, part B, the fenofibrate in microfluidized phospholipid-stabilized microparticles (bar 4) is more bioavailable than that in a micronized formulation (bar 3) in a low fat fed state. In FIG. 2, part C., there is no significant difference in bioavailability between the fenofibrate in microfluidized phospholipid-stabilized microparticles (bar 6) and in a micronized formulation (bar 5). Bioavailability of fenofibrate increases by more than a factor of two when comparing bars 1, 3, and 5 that refer to a micronized formulation of fenofibrate. However, bioavailability of fenofibrate is approximately constant when comparing bars 2, 4, and 6 that refer to fenofibrate in a microfluidized phospholipid-stabilized microparticle formulation. The bioavailability of fenofibrate in formulations of microfluidized phospholipid-stabilized microparticles is seen to increase by less than 25% when comparing fasting and high fat fed conditions (bars 2 and 6), preferably increasing by less than 20%, and more preferably by less than 15% (bars 2 and 6). The clinical data used to produce bars 2 and 6 indicate an increase of 14% in the bioavailability of fenofibrate between fasted and high fat fed conditions, i.e., a factor of 1.14 between bioavailabilities represented by bar 2 (fasted) versus bar 6 (high fat fed). Blood levels of fenofibric acid were measured to obtain the data from which FIG. 2 was generated.

This invention discloses a method of treatment of dislipidemia and dislipoproteinemia in a mammal patient which comprises administering to the mammal a therapeutically effective oral dosage form comprising microparticles of a solid fibrate that are stabilized by a phospholipid surface active substance, wherein the dosage form provides into the blood of the mammal patient in a fasted state a therapeutically effective amount of the fibrate active species that is at least 90% of the AUC (that is, area under the curve) amount of the fibrate active species provided by the dosage form into the blood of the mammal patient in a fed state.

In one aspect of the disclosed method of treatment dislipidemia and dislipoproteinemia in a mammal patient, the dislipidemia comprises hypercholesterolemia, hyperlipidemia, hypertrigylceridaemia, and combinations thereof.

In one aspect of the disclosed method of treatment dislipidemia and dislipoproteinemia in a mammal patient, the fibrate is poorly water soluble or insoluble in water.

In one aspect of the disclosed method of treatment dislipidemia and dislipoproteinemia in a mammal patient, the dosage form is selected from the group consisting of a tablet, a film-coated tablet, a moisture resistant tablet, a tablet coated with a pharmaceutically acceptable polymer, and a capsule.

In one aspect of the disclosed method of treatment dislipidemia and dislipoproteinemia in a mammal patient, the method of treatment comprises administering to the mammal patient a therapeutically effective oral dosage form comprising microparticles of a solid fenofibrate that are stabilized by a phospholipid surface active substance wherein the dosage form provides into the blood of the patient in a fasted state a therapeutically effective amount of fenofibrate active species that is at least 90% of the AUC (that is, area under the curve) amount of the fenofibrate active species provided by the dosage form into the blood of the mammal patient in a fed state.

This invention discloses an orally administered pharmaceutical composition comprising microparticles of solid fibrate that are stabilized by a phospholipid surface active substance, wherein the microparticles are prepared in the presence of a phospholipid surface active substance, and wherein a therapeutically effective amount or dose of the composition provides a quantity of fibrate active species to a fasted human patient in need of treatment by the fibrate that is greater than 90% of the quantity of the fibrate active species provided by the therapeutically effective amount or dose to the patient when the patient is fed a high fat meal.

This invention discloses an orally administered pharmaceutical composition comprising microparticles of solid fenofibrate that are stabilized by a phospholipid surface active substance, wherein the microparticles are prepared in the presence of a phospholipid surface active substance, and wherein a therapeutically effective amount or dose of the composition provides a quantity of fenofibrate active species to a fasted human patient in need of treatment by the fenofibrate that is greater than 90% of the quantity of the fenofibrate active species provided by the therapeutically effect amount or dose of the composition to the patient when the patient is fed a high fat meal.

This invention discloses a capsule or tablet dosage form for oral administration comprising a pharmaceutically effective amount of a composition of small particles of a fibrate stabilized by a phospholipid stabilizing agent, a sugar, and optionally a carbohydrate-derived alcohol, wherein a dosage amount or dose of the dosage form provides a level of fibrate active species into the blood of a patient in a fasted state that differs by less than 25% of the level of the fibrate active species that the patient receives from the dose when the patient is in a fed state.

This invention discloses a capsule or tablet dosage form for oral administration comprising a pharmaceutically effective amount of a composition of small particles of a fibrate stabilized by a phospholipid stabilizing agent, a sugar, and optionally a carbohydrate-derived alcohol, wherein a dosage amount or dose of the dosage form provides a level of fibrate active species into the blood of a patient in a fasted state that differs by less than 20% of the level of the fibrate active species that the patient receives from the dose when in a fed state.

This invention discloses a capsule or tablet dosage form for oral administration comprising a pharmaceutically effective amount of a composition of small particles of a fibrate stabilized by a phospholipid stabilizing agent, a sugar, and optionally a carbohydrate-derived alcohol, wherein a dosage amount or dose of the dosage form provides a level of fibrate active species into the blood of a patient in a fasted state that differs by less than 15% of the level of the fibrate active species that the patient receives from the dose when in a fed state.

This invention discloses a capsule or tablet dosage form for oral administration comprising a pharmaceutically effective amount of a composition of small particles of a fibrate stabilized by a phospholipid stabilizing agent, a sugar, and optionally a carbohydrate-derived alcohol, wherein a dosage amount or dose of the dosage form provides a level of fibrate active species into the blood of a patient who is in a fasted state that differs by less than 10% of the level of the fibrate active species that the patient receives from the dose when in a fed state.

This invention discloses a capsule or tablet dosage form for oral administration comprising a pharmaceutically effective amount of a composition of small particles of a fibrate stabilized by a phospholipid stabilizing agent, a sugar, and optionally a carbohydrate-derived alcohol, wherein a dosage amount or dose of the dosage form provides a level of fibrate active species into the blood of a patient who is in a fasted state that differs by less than 5% of the level of the fibrate active species that the patient receives from the dose when in a fed state.

This invention discloses a tablet dosage form that comprises a dried film-coating.

This invention discloses a tablet dosage form comprising a pharmaceutically acceptable polymer in a coating.

This invention discloses a tablet dosage form comprising a pharmaceutically acceptable carbohydrate in a coating.

This invention discloses a tablet dosage form comprising a pharmaceutically acceptable carbohydrate in a coating, wherein the carbohydrate in the coating is a sugar.

This invention discloses a tablet dosage form and a capsule dosage form, each comprising a fibrate, wherein the fibrate is fenofibrate.

This invention discloses a tablet dosage form and a capsule dosage form, each comprising one or more excipients selected from the group consisting of monosaccharides, disaccharides, trisaccharides, sucrose, lactose, mannitol, sorbitol, trehalose, glycerol, dextrose, fructose, sugars, pentoses, hexoses, xylitol, and combinations thereof.

This invention discloses a tablet dosage form and a capsule dosage form, each comprising a phospholipid surface-active substance, wherein the phospholipid surface-active substance comprises a mixture of phospholipids.

This invention discloses a tablet dosage form and a capsule dosage form, each comprising a phospholipid surface-active substance, wherein the phospholipid surface active substance is selected from the group consisting of egg phospholipid, Lipoid E80, Lipoid EPC, Lipoid SPC, DMPG, Phospholipon 100H, a hydrogenated soybean phosphatidylcholine, Phospholipon 90H, Lipoid SPC-3, and combinations thereof.

This invention discloses a composition comprising solid fenofibrate, wherein the solid fenofibrate is crystalline.

This invention discloses a composition comprising microparticles, wherein the microparticles are smaller than 5 micrometers.

This invention discloses a composition comprising microparticles, wherein the microparticles are smaller than 4 micrometers.

This invention discloses a composition comprising microparticles, wherein the microparticles are smaller than 3 micrometers.

This invention discloses a composition comprising microparticles, wherein the microparticles are smaller than 2 micrometers.

This invention discloses a composition comprising microparticles, wherein the microparticles are smaller than 1 micrometer.

This invention discloses a composition comprising microparticles, wherein the microparticles are smaller than 0.5 micrometers.

This invention discloses a dosage form comprising microparticles of fenofibrate, wherein the microparticles are prepared by a process selected from the group consisting of homogenization, microfluidization, hot melt microfluidization, sonication, precipitation, media milling, ball milling, jet milling, and combinations thereof.

This invention discloses a dosage form comprising microparticles of fenofibrate, wherein the microparticles are prepared by a process of homogenization, microfluidization, or hot melt microfluidization.

This invention discloses a dosage form comprising a therapeutically effective amount of fenofibrate, wherein the therapeutically effective amount is selected from the group consisting of 50 mg of fenofibrate, 51 mg of fenofibrate, 52 mg of fenofibrate, 53 mg of fenofibrate, 54 mg of fenofibrate, 67 mg of fenofibrate, 100 mg of fenofibrate, 102 mg of fenofibrate, 103 mg of fenofibrate, 104 mg of fenofibrate, 134 mg of fenofibrate, 150 mg of fenofibrate, 153 mg of fenofibrate, 156 mg of fenofibrate, 159 mg of fenofibrate, 160 mg of fenofibrate, 200 mg of fenofibrate, 213 mg of fenofibrate, 250 mg of fenofibrate, and 300 mg of fenofibrate.

This invention discloses an orally administered pharmaceutical composition, for example as a tablet or capsule dosage form, comprising microparticles of solid fenofibrate that are stabilized by a phospholipid surface active substance, wherein the microparticles are prepared in the presence of a phospholipid surface active substance, and wherein a therapeutically effective dosage amount of the composition (or dose) provides a quantity of fenofibrate to a fasted human patient in need of treatment by fenofibrate that is greater than 85% of the quantity of fenofibrate provided by the dosage amount or dose to the patient when the patient is fed at least 1000 calories, 50% of which are from fat.

This invention discloses an orally administered pharmaceutical composition, for example as a tablet or capsule dosage form, comprising microparticles of solid fenofibrate that are stabilized by a phospholipid surface active substance, wherein the microparticles are prepared in the presence of a phospholipid surface active substance, and wherein a therapeutically effective dosage amount or dose of the composition provides a quantity of fenofibrate or fenofibrate active species to a fasted human patient in need of treatment by fenofibrate that is greater than 90% of the quantity of fenofibrate or fenofibrate active species provided by the dosage amount or dose to the patient when the patient is fed at least 1000 calories, 50% of which are from fat.

This invention discloses an orally administered pharmaceutical composition, for example as a tablet or capsule dosage form, comprising microparticles of solid fenofibrate that are stabilized by a phospholipid surface active substance, wherein the microparticles are prepared in the presence of a phospholipid surface active substance, and wherein a therapeutically effective dosage amount or dose of the composition provides a quantity of fenofibrate or fenofibrate active species to a fasted human patient in need of treatment by fenofibrate that is greater than 95% of the quantity of fenofibrate or fenofibrate active species provided by the dosage amount or dose to the patient when the patient is fed at least 1000 calories, 50% of which are from fat.

This invention discloses a composition comprising phospholipid-stabilized fenofibrate microparticles and one or more excipients selected from the group consisting of monosaccharides, disaccharides, trisaccharides, sucrose, lactose, mannitol, sorbitol, trehalose, glycerol, dextrose, fructose, sugars, pentoses, hexoses, xylitol, and combinations thereof.

This invention discloses a composition comprising a phospholipid surface active substance, wherein the phospholipid surface active substance is selected from the group consisting of egg phospholipid, Lipoid E80, Lipoid EPC, Lipoid SPC, DMPG, Phospholipon 100H, a hydrogenated soybean phosphatidylcholine, Phospholipon 90H, Lipoid SPC-3, and combinations thereof.

This invention discloses a composition comprising microparticles of phospholipid-stabilized fenofibrate, wherein the microparticles are prepared by a process selected from the group consisting of homogenization, microfluidization, hot melt microfluidization, and sonication.

This invention discloses a composition comprising microparticles of phospholipid-stabilized fenofibrate, wherein the microparticles of fenofibrate are prepared by a process comprising the steps of:

(a) mixing at high shear an admixture of fenofibrate and a phospholipid substance in an aqueous carrier in the absence of an organic solvent within a first temperature range at or above the melting point of fenofibrate to form a heated suspension wherein fenofibrate is molten;

(b) homogenizing the heated suspension in a first pressure range and within a first temperature range to form a heated homogenate containing fenofibrate;

(c) cooling the heated homogenate to a second temperature range below the melting temperature of fenofibrate to form a transiently stable cooled homogenate containing fenofibrate;

(d) applying a particle stabilizing energetic process to the cooled homogenate within a second temperature range below the melting temperature of fenofibrate and in a second pressure range to form a cooled dispersion of small particles containing fenofibrate, and (e) drying the cooled dispersion to form dried small particles containing fenofibrate.

This invention also discloses the above process comprising an admixture, wherein the admixture further comprises a bulking agent.

This invention also discloses the above process comprising a heated suspension, wherein the heated suspension further comprises a bulking agent.

This invention also discloses the above process comprising a heated homogenate, wherein the heated homogenate further comprises a bulking agent.

This invention also discloses the above process comprising a cooled homogenate, wherein the cooled homogenate further comprises a bulking agent.

This invention also discloses the above process comprising a cooled dispersion, wherein the cooled dispersion further comprises a bulking agent.

This invention also discloses the above process comprising a bulking agent, wherein the bulking agent is selected from the group consisting of a monosaccharide, a disaccharide, a trisaccharide, sucrose, lactose, mannitol, sorbitol, trehalose, glycerol, dextrose, fructose, a sugar, a pentose, a hexose, xylitol, and combinations thereof.

This invention also discloses the above process comprising a bulking agent, wherein the bulking agent is selected from the group consisting of trehalose, sucrose, sorbitol, and combinations thereof.

This invention also discloses the above process comprising a bulking agent, wherein the bulking agent is trehalose.

This invention also discloses the above process comprising a bulking agent, wherein the bulking agent is a mixture or combination of sucrose and sorbitol.

This invention also discloses the above process comprising a phospholipid substance, wherein the phospholipid substance is selected from the group consisting of egg phospholipid, Lipoid E80, Lipoid EPC, Lipoid SPC, DMPG, Phospholipon 100H, Lipoid SPC-3, and combinations thereof.

This invention also discloses the above process comprising a phospholipid substance, wherein the phospholipid substance is Lipoid E80.

This invention also discloses the above process comprising a first temperature range, wherein the first temperature range is at or above the melting point of fenofibrate or in the range of about 82° C. to about 100° C.

This invention also discloses the above process comprising a first temperature range, wherein the first temperature range is from the melting point of fenofibrate to about 20° C. above the melting point of fenofibrate.

This invention also discloses the above process comprising a second temperature range, wherein the second temperature range is below the melting point of fenofibrate.

This invention also discloses the above process comprising a second temperature range, wherein the second temperature range is from about 4° C. to about 40° C., and wherein fenofibrate is not molten.

This invention also discloses the above process comprising an aqueous carrier, wherein the aqueous carrier is selected from the group consisting of water, sterile water, water for injection, and phosphate buffered water having a pH from 4 to 10.

This invention also discloses the above process comprising an aqueous carrier, wherein the aqueous carrier is phosphate buffered water having a pH from 7 to 9.

This invention also discloses the above process comprising an aqueous carrier, wherein the aqueous carrier is phosphate buffered water having a pH from 7.5 to 8.5.

This invention also discloses the above process comprising a first pressure range, wherein the first pressure range is from 2,000 to 30,000 psi.

This invention also discloses the above process comprising a second pressure range, wherein the second pressure range is 18,000 to 5,000 psi.

This invention also discloses the above process comprising small particles, wherein the small particles have size in the range from 0.05 to 2 micrometers.

This invention also discloses a method of treating dislipidemia and dislipoproteinemia in a mammal patient which comprises administering to the mammal once a day a dosed amount of a therapeutically effective oral dosage form such as a tablet or capsule dosage form comprising microparticles of a solid fibrate that are stabilized by a phospholipid surface active substance, wherein the dosed amount of the dosage form provides into the blood of a mammal patient who is in a fasted state a therapeutically effective amount of the fibrate or fibrate active species that is at least 90% of the AUC (i.e., area under the curve) amount of the fibrate or fibrate active species that is provided by the same dosed amount of the dosage form into the blood of the mammal patient when the patient is in a fed state.

This invention also discloses a method of treating dislipidemia and dislipoproteinemia in a mammal patient which comprises administering to the mammal once a day a dosed amount of a therapeutically effective oral dosage form such as a tablet or capsule dosage form comprising microparticles of a solid fenofibrate that are stabilized by a phospholipid surface active substance, wherein the dosed amount of the dosage form provides into the blood of a mammal patient who is in a fasted state a therapeutically effective amount of the fenofibrate or fenofibrate active species that is at least 90% of the AUC (i.e., area under the curve) amount of the fenofibrate or fenofibrate active species that is provided by the same dosed amount of the dosage form into the blood of the mammal patient when the patient is in a fed state.

This invention also discloses a dosage form comprising phospholipid-stabilized fenofibrate microparticles in a tablet as described herein, which tablet is coated with one or more barrier layers that are substantially impermeable to moisture.

In one aspect, the dose of fenofibrate tablets or capsules of this invention consists of one tablet or one capsule taken once a day.

In one aspect, the dose of fenofibrate tablets or capsules of this invention consists of one tablet or one capsule taken twice a day.

In one aspect, the dose of fenofibrate tablets or capsules of this invention consists of one tablet or one capsule taken three times a day.

In one aspect, the dose of fenofibrate tablets or capsules of this invention consists of two to four tablets or two to four capsules taken once a day.

In one aspect, the dose of fenofibrate tablets or capsules of this invention consists of two to four tablets or two to four capsules taken twice a day.

In one aspect, the dose of fenofibrate tablets or capsules of this invention consists of two to four tablets or two to four capsules taken three times a day.

In an embodiment, the present invention provides a pharmaceutically acceptable oral dosage form comprising fenofibrate, phospholipid, a buffer salt, a water-soluble bulking agent selected from maltodextrin, mannitol, and combinations thereof, a cellulosic additive, beads or crystals of a pharmaceutically acceptable water-soluble excipient support material, a polyvinylpyrrolidone or crospovidone, croscarmellose sodium, granular mannitol, sodium dodecyl sulfate, silicon dioxide, and a stearate, wherein the fenofibrate is in the form of microparticles, and wherein at least a portion of the phospholipid is coated on the surfaces of the fenofibrate microparticles, the phospholipid coated microparticles are embedded in a matrix comprising the water-soluble bulking agent, phospholipid that is not coated on the microparticles, the buffer salt and the cellulosic additive, and the matrix is coated on up to 100% of the surfaces of the beads or crystals of the excipient support material.

In an embodiment, the fenofibrate is present in an amount of from about 15% w/w to about 20% w/w of the dosage form.

In an embodiment, the phospholipid is present in an amount of from about 1% w/w to about 8% w/w of the dosage form.

In an embodiment, the buffer salt is present in an amount of from about 0.1% w/w to about 0.5% w/w of the dosage form.

In an embodiment, the water-soluble bulking agent is present in an amount of from about 7% W/w to about 20% w/w of the dosage form.

In an embodiment, the cellulosic additive is present in an amount of from about 3% w/w to about 8% w/w of the dosage form.

In an embodiment, the water-soluble excipient support material is present in an amount of from about 12% w/w to 16% w/w of the dosage form.

In an embodiment, the polyvinylpyrrolidone or crospovidone is present in an amount of from about 5% w/w to about 30% w/w of the dosage form.

In an embodiment, the croscarmellose sodium is present in an amount of from about 1% w/w to about 6% w/w of the dosage form.

In an embodiment, the granular mannitol is present in an amount of from about 3% w/w to about 30% w/w of the dosage form.

In an embodiment, the sodium dodecyl sulfate is present in an amount of from about 1% w/w to about 4% of the dosage form.

In an embodiment, the silicon dioxide is present in an amount of up to about 1% w/w of the dosage form.

In an embodiment, the stearate is present in an amount of up to about 1% w/w of the dosage form.

In an embodiment, the phospholipid is an egg lecithin.

In an embodiment, the buffer salt is sodium phosphate.

In an embodiment, the water-soluble bulking agent is maltodextrin.

In an embodiment, the cellulosic additive is carboxymethylcellulose.

In an embodiment, the water-soluble excipient support material is in the form of a bead or crystal.

In an embodiment, the water-soluble excipient support material is lactose.

In an embodiment, the The silicon dioxide is colloidal silica.

In an embodiment, the stearate is magnesium stearate.

In an embodiment, the dosage form is a tablet or capsule.

In an embodiment, the matrix is coated on about 80% to about 50% of the surfaces of the beads or crystals of the excipient support material.

In an embodiment, the dosage form further includes a protective coating.

The present invention further provides a pharmaceutically acceptable tablet dosage form of fenofibrate comprising fenofibrate present in an amount of from about 15% w/w to about 20% w/w of the dosage form;

phospholipid present in an amount of from about 1% w/w to about 8% w/w of the dosage form;

a buffer salt present in an amount of from about 0.1% w/w to about 0.5% w/w of the dosage form;

a water-soluble bulking agent selected from maltodextrin, mannitol, and a combination thereof present in an amount of from about 7% w/w to about 20% w/w of the dosage form;

a cellulosic additive present in an amount of from about 3% w/w to about 8% w/w of the dosage form;

beads or crystals of a pharmaceutically acceptable water-soluble excipient support material present in an amount of from about 12% w/w to 16% w/w of the dosage form;

a polyvinylpyrrolidone or crospovidone present in an amount of from about 5% w/w to about 30% w/w of the dosage form;

croscarmellose sodium present in an amount of from about 1% w/w to about 6% w/w of the dosage form;

granular mannitol present in an amount of from about 3% w/w to about 30% w/w of the dosage form;

sodium dodecyl sulfate present in an amount of from about 1% w/w to about 4% of the dosage form;

silicon dioxide present in an amount of up to about 1% w/w of the dosage form; and a stearate present in an amount of up to about 1% w/w of the dosage form;

wherein the fenofibrate is in the form of microparticles, and wherein at least a portion of the phospholipid is coated on the surfaces of the fenofibrate microparticles, and wherein the phospholipid coated microparticles are embedded in a matrix comprising the water-soluble bulking agent, phospholipid that is not coated on the microparticles, the buffer salt and the cellulosic additive, and wherein the matrix is coated on up to 100% of the surfaces of the beads or crystals of the excipient support material.

In an embodiment, the fenofibrate is present in an amount of from about 18% w/w to about 19.5% w/w of the tablet.

In an embodiment, the phospholipid is present in an amount of from about 2% w/w to about 6% w/w of the tablet.

In an embodiment, the buffer salt is present in an amount of from 0.1% w/w to about 0.2% w/w of the tablet.

In an embodiment, the bulking agent is maltodextrin present in an amount of from about 9% w/w to about 20% w/w of the tablet.

In an embodiment, the bulking agent is mannitol present in an amount of from about 7% w/w to about 20% w/w of the tablet.

In an embodiment, the cellulosic additive is a carboxymethylcellulose.

In an embodiment, the cellulosic additive is sodium carboxymethylcellulose.

In an embodiment, the cellulosic additive is present in an amount of from about 4% w/w to about 6% w/w of the tablet.

In an embodiment, the water-soluble excipient support material present is present in an amount of from about 14% w/w to about 15% w/w of the tablet.

In an embodiment, the polyvinylpyrrolidone or crospovidone is present in an amount of from about 6% w/w to about 26% w/w of the tablet.

In an embodiment, the croscarmellose sodium is present in an amount of from about 2% w/w to about 5% w/w of the tablet.

In an embodiment, the granular mannitol is present in an amount of from about 5% w/w to about 27% w/w of the tablet.

In an embodiment, the sodium dodecyl sulfate is present in an amount of from about 2% w/w to about 3% w/w of the tablet.

In an embodiment, the silicon dioxide is colloidal silicon dioxide present in an amount of from about 0.5% w/w to about 0.8% w/w of the tablet.

In an embodiment, the stearate is magnesium stearate present in an amount of from about 0.2% w/w to about 0.5% w/w of the tablet.

The present invention further provides a process for preparing an oral dosage form comprising:

(a) forming an aqueous suspension comprising phospholipid coated microparticles of fenofibrate and buffer;

(b) forming an admixture of the aqueous suspension with one or more bulking agents;

(c) drying the admixture on the pharmaceutically acceptable water-soluble excipient support material to produce a solid;

(d) course milling and blending the solid with one or more pharmaceutically acceptable excipients to provide a dried powder; and (e) forming said dried powder into an oral dosage form.

The present invention further provides a method of treating dislipidemia or dislipoproteinemia in a mammal comprising administering to sadi mammal a therapeutically effective oral dosage form as described above, for example, a method wherein the dosage form provides into the blood of said mammal in a fasted state a therapeutically effective amount of said fenofibrate that is at least 90% of the area under the curve (AUC) amount of the fenofibrate provided by the dosage form into the blood of said mammal in a fed state.

In an embodiment, the fenofibrate is present in an amount of from 45 to 51 mg per dosage form.

In an embodiment, the fenofibrate is present in an amount of from 45 to 51 mg per tablet dosage form.

In an embodiment, the fenofibrate is present in an amount of 48 mg per dosage form.

In an embodiment, the fenofibrate is present in an amount of 48 mg per tablet dosage form.

In an embodiment, the fenofibrate is present in an amount of from 135 to 155 mg per dosage form.

In an embodiment, the fenofibrate is present in an amount of from 135 to 155 mg per tablet dosage form.

In an embodiment, fenofibrate is present in an amount of 144 or 145 mg per dosage form.

In an embodiment, fenofibrate is present in an amount of 144 or 145 mg per tablet dosage form.

In an embodiment, fenofibrate is present in an amount of from 120 to 130 mg per dosage form.

In an embodiment, fenofibrate is present in an amount of from 120 to 130 mg per tablet dosage form.

The invention is additionally illustrated in connection with the following examples, which are considered to be illustrative of the present invention. It should be understood, however, that the invention is not limited to the specific details of the Examples.

EXAMPLE 1

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M100Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. The resulting cooled dispersion comprising small particles containing fenofibrate of size less than 1.0 micron in diameter is then dried by freezing to about −40° C. and lyophilization under vacuum to produce dried small particles containing fenofibrate.

EXAMPLE 2

A mixture of 60 parts of Lipoid E80 as the surface active substance and 200 parts of a poorly water soluble drug, fenofibrate, is homogeneously dispersed in 1440 parts of 10 mM pH 8.0+/− 0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 80° C. to form a heated homogenate containing the drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug are of a size less than 1.0 micron in diameter and are then dried by freezing and lyophilization under vacuum to produce dried small particles containing fenofibrate.

EXAMPLE 3

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer containing 240 parts of trehalose using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to 95° C. to form a heated homogenate containing the drug. After 10 passes, the heated homogenate is cooled by passage through a heat exchanger chilled with ice water, kept at 4° C. for 30 minutes in an ice/water bath, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is then dried by freezing in liquid nitrogen and lyophilization under vacuum to produce dried small particles containing fenofibrate.

EXAMPLE 4

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug of size less than 1.0 micron in diameter is treated with a solution of 200 parts of sucrose plus 100 parts of sorbitol as bulking agents in additional aqueous carrier and is then dried by freezing in liquid nitrogen and lyophilization under vacuum to produce dried small particles containing fenofibrate.

EXAMPLE 5

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing the drug of size less than 1.0 micron in diameter is treated with a solution of bulking agents equivalent to 300 parts of sucrose plus 100 parts of sorbitol in additional aqueous carrier is then dried by freezing and lyophilization to produce dried small particles containing fenofibrate.

EXAMPLE 6

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is treated with 100 parts of sucrose plus 20 parts of glycerol as bulking agents, then dried to produce dried small particles containing fenofibrate.

EXAMPLE 7

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 85° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles containing drug of size less than 1.0 micron in diameter is treated with a cooled solution of 200 parts of trehalose plus 100 parts of PVP17 as bulking agents in additional aqueous carrier and then dried by freezing and lyophilization or by spray drying to produce dried small particles containing fenofibrate.

EXAMPLE 8

A mixture of 60 parts of Lipoid E80 as the surface active substance and 200 parts of a poorly water soluble drug, fenofibrate, is homogeneously dispersed in 1440 parts of 10 mM pH 8.0+/−0.2 aqueous phosphate buffer containing 200 parts of sucrose and 100 parts of sorbitol using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y homogenizer operated at 3,400 to 3,600 psig while maintained at 80° C. to form a heated homogenate containing drug. After 10 passes, the heated homogenate is cooled by passage through a heat exchanger chilled with ice water, kept at 4° C. for 30 min, and the transiently stable cooled homogenate is further homogenized for 10 to 20 batch volume cycles or passes using a Microfluidics M110 EH homogenizer operated at 18,000 psig (peak) while maintained between 4° C. and 15° C. The resulting cooled dispersion comprising small particles of size less than 1.0 micrometers in diameter is then dried to produce dried small particles containing fenofibrate.

EXAMPLE 9

An admixture of a formulation comprising 60 parts of a hydrogenated soybean phosphatidylcholine (i.e., phospholipon 100H) as a surface active substance and 200 parts of a poorly water soluble drug, fenofibrate, in 1400 parts of aqueous carrier (10 mM phosphate buffer at pH 8) is heated to 85° C. and homogenized for 10 volume passes to form a heated homogenate containing drug containing the drug, cooled to room temperature according to method 1 to form a transiently stable cooled homogenate containing the drug, and then sonicated for 1 minute using a 550 Sonic Dismembrator Probe Sonicator from Fisher Scientific (10 s pulses at power level 5) to form a cooled dispersion. The mean particle diameter of the sonicated material (cooled dispersion) is only slightly larger than that of the heated homogenate material, both being between 2-4 micrometers. Microscopically, the heated homogenate particles are non-crystalline while the cooled dispersion particles are crystalline. Importantly, while stirring induces significant particle growth in the cooled homogenate, stirring does not induce significant particle growth in the cooled dispersion. The cooled dispersion thus produced is more robust toward particle growth than the cooled homogenate.

EXAMPLE 10

A mixture of 60 parts of a phospholipid as a surface active substance and 200 parts of a poorly water soluble drug is homogeneously dispersed in 1440 parts of 10 mM pH 8.0+/−0.2 aqueous phosphate buffer using a ProScientific 400 high shear mixer at 2,000 to 3,600 rpm at ambient temperature for 30 minutes, and then heated above the melting point of the drug during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained above the melting point of the drug to form a heated homogenate containing drug. After 10 passes, the heated homogenate is cooled by passage through a heat exchanger chilled with ice water, and the transiently stable cooled homogenate is further homogenized for 10 to 20 batch volume cycles or passes using a Microfluidics M110 EH homogenizer operated at 18,000 psig (peak) while maintained at 4° C. to 15° C. The resulting cooled dispersion comprising particles containing the poorly water soluble drug is then dried by freezing and lyophilization to produce dried small particles containing the poorly water soluble drug.

EXAMPLE 11

Cooled dispersions prepared according to examples 1 to 9 are placed into 10 ml vials and individually frozen and lyophilized to provide dried small particles containing fenofibrate.

EXAMPLE 12

Cooled dispersions prepared according to examples 1 to 9 are individually spray dried to provide dried small particles containing fenofibrate.

EXAMPLE 13

The cooled dispersion prepared according to example 10 is placed in 10 ml vials, frozen and lyophilized to provide dried small particles containing fenofibrate.

EXAMPLE 14

The cooled dispersion prepared according to example 10 is spray dried to provide dried small particles containing fenofibrate.

EXAMPLE 15

A mixture of 225 parts of Lipoid E80 as the surface active substance, 750 parts of fenofibrate, 375 parts of sorbitol, and 750 parts of sucrose is homogeneously dispersed in 6000 parts of 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension is then recirculatively homogenized for 10 batch volume cycles or passes using a Microfluidizer M110Y operated at 3,400 to 3,600 psig while maintained at 85° C. to 99° C. to form a heated homogenate containing the drug. After 10 passes, the heated homogenate is cooled by passage through a heat exchanger cooled by chilled water at 5° C. to 10° C. and the transiently stable cooled homogenate is further homogenized for 10 to 20 batch volume cycles or passes using a Microfluidics M110 EH homogenizer operated at 18,000 psig (peak) while maintained at 4° C. to 13° C. The resulting cooled dispersion comprising small particles containing fenofibrate of size less than 1.0 micron in diameter is then dried by freezing to about −40° C. and lyophilization under vacuum to produce dried small particles containing fenofibrate.

EXAMPLE 16

The dried small particles containing fenofibrate prepared in Example 15 are blended with 0.2% Cabosil, 5% sucrose, and 0.25% magnesium stearate. After thorough blending, the mixture is compressed into tablets for oral dosing. The tablets are prepared at the following dosage levels of fenofibrate and are sized according to volumes encountered.
50 mg
51 mg
52 mg
53 mg
54 mg
67 mg
100 mg
102 mg
104 mg
106 mg
134 mg
150 mg
153 mg
156 mg
159 mg
160 mg
200 mg
213 mg
250 mg
300 mg

EXAMPLE 17

Gelatin capsules are filled with the dried small particles containing fenofibrate prepared in Example 15 and sealed to provide capsules for oral dosing. The capsules are filled at the following dosage levels of fenofibrate and are sized according to volumes encountered.
50 mg
51 mg
52 mg
53 mg
54 mg
67 mg
100 mg
102 mg
104 mg
106 mg
134 mg
150 mg
153 mg
156 mg
159 mg
160 mg
200 mg
213 mg
250 mg
300 mg

EXAMPLE 18

Oral bioavailability of a microfluidized phospholipid-stabilized microparticle formulation of fenofibrate in human subjects.

An oral capsule dosage form of a formulation of microfluidized Phospholipon 100H-stabilized fenofibrate microparticles (67 mg dose of fenofibrate) prepared with Tween 80 and mannitol was administered to human volunteers. The study consisted of oral administration of capsules containing a formulation of microfluidized Phospholipon 100H-stabilized fenofibrate microparticles to eight human volunteers in a single dose crossover design, using a commercially marketed formulation of micronized fenofibrate as a reference. The dose administered was 67 mg. Blood samples were collected before and after each administration at various time points over 120 hours. The drug concentration in blood samples was determined by high-pressure liquid chromatography by monitoring for the level of the metabolite, fenofibric acid. The pharmacokinetic results are presented in Table 5. The ratio of the least-squares means (ln-transformed data) was 1.49±0.24, and demonstrate the superior bioavailability of fenofibrate in the microfluidized phospholipid-stabilized fenofibrate microparticle formulation over the commercially available product.

TABLE 5

$C_{max}$ and $AUC_{0-inf}$ for Fenofibric Acid

| | $C_{max}$ (ng · ml$^{-1}$) | $AUC_{0-\infty}$ (ng · ml$^{-1}$ · h) |
|---|---|---|
| Microfluidized phospholipid-stabilized fenofibrate microparticle formulation (67 mg) | 2528 | 57236 |
| Commercially available micronized fenofibrate (67 mg) product | 1372 | 38629 |
| Dunnett's t-test (log-transformed data) | p < 0.05 | p < 0.05 |

EXAMPLE 19

Elimination of the food effect associated with marketed formulations of fenofibrate using a microfluidized phospholipid-stabilized microparticle formulation of fenofibrate in human subjects.

The oral bioavailability of a capsule dosage form of a microfluidized phospholipid-stabilized microparticle formulation of fenofibrate comprising Phospholipon 100H-stabilized fenofibrate microparticles prepared by microfluidization, Tween 80, and mannitol was tested and compared with the marketed micronized formulation of fenofibrate in fasting and fed states in a single dose pharmacokinetic study. The study consisted of the oral administration of capsules of the test formulations to 8 human subjects in a single dose, crossover design with four treatment periods. Both drug formulations were administered as 67 mg capsules. Blood samples were collected before and after each administration at various time points over 120 hours. The drug concentration in blood samples was determined by high-pressure liquid chromatography by monitoring for the level of the metabolite, fenofibric acid. The bioavailability ($AUC_{0-\infty}$) under the different conditions is presented in Table 6. The food effect is represented by the ratio of the $AUC_{0-\infty}$ under fed and fasted conditions. The results demonstrate a significant ($p<0.05$) food effect with the marketed micronized fenofibrate product (+73%), while the food effect with the microfluidized phospholipid stabilized microparticle fenofibrate was only 13% (NS), demonstrating the virtual elimination of the dependence on food for optimal bioavailability.

TABLE 6

$AUC_{0-\infty}$ for fenofibric acid under fasted and fed conditions

| $AUC_{0-\infty}$ (ng · ml$^{-1}$ · h) | Microfluidized phospholipid stabilized microparticle fenofibrate (67 mg) | Marketed micronized fenofibrate product (67 mg) |
|---|---|---|
| Fasting state | 57236 | 38629 |
| Fed state | 64585 | 66969 |
| $F_{rel}$ (fed/fasted) | 1.13 | 1.73 |
| Dunnett's t-test (ln-transformed data) | NS | p < 0.05 |

EXAMPLE 20

Demonstration of the absence of food effect with a microfluidized phospholipid-stabilized microparticle formulation of fenofibrate (IDD-P™ fenofibrate) in human subjects An IDD-P™ fenofibrate formulation prepared by a hot melt microfluidization process described herein under GMP conditions according to the method of Example 15 was dried by lyophilization and formulated into tablets containing 160 mg of fenofibrate. In the formulation, the IDD-P™ fenofibrate was in the form of microfluidized microparticles stabilized by phospholipid Lipoid E80 and was prepared by microfluidization in the presence of sucrose and sorbitol. The oral bioavailability of the tableted IDD-P™ fenofibrate formulation was tested in the fasting and fed states in a single dose pharmacokinetic study. The study consisted of the administration of a single IDD-P™ fenofibrate tablet containing 160 mg of fenofibrate in 8 human subjects using a crossover design with randomized sequences. The fed condition was obtained with a high fat meal containing 1000 Kcal and 50 g fat. The blood samples were collected before and after each administration at various time points over 96 hours. The drug concentration in blood samples was determined by high-pressure liquid chromatography by monitoring for the level of the metabolite, fenofibric acid. The bioavailability of the drug from a dosage form such as an orally administered composition of the drug is given by the accumulated amount of drug versus time detected in a patient, and is calculated as the area under the curve of a plot of fenofibric acid concentrations detected in blood versus time. The bioavailability ($AUC_{0-\infty}$) data obtained under the fed and fasted conditions are presented in Table 7. The food effect is represented by the ratio of the $AUC_{0-\infty}$ under fed and fasted conditions. The ratio of 95% (fasted/fed) demonstrates the essential absence of food effect on the bioavailability of IDD-P™ fenofibrate. The ratio of the $AUC_{0-\infty}$ under fasted/fed conditions is 1.07. Thus the bioavailability of microfluidized phospholipid stabilized microparticles of fenofibrate increases by less than 8% between fasted and fed conditions in this example.

TABLE 7

$AUC_{0-\infty}$ for fenofibric acid under fasted and fed conditions

| | $AUC_{0-\infty}$ (ng · ml$^{-1}$ · h) |
|---|---|
| Fasting state | 126282 |
| Fed state | 135201 |
| $F_{rel}$ (fasted/fed)[1] | 0.95 |

[1]Ratio of the least-squares means using ln-transformed data

EXAMPLE 21

The following formulations were prepared according to the method of example 10 leading to a suspension before drying:
21-1) 10% fenofibrate, 3% Lipoid E80, 10% sucrose;
21-2) 10% fenofibrate, 3% Lipoid E80, 10% sucrose, 5% sorbitol;
21-3) 10% fenofibrate, 3% Lipoid E80, 10% sucrose, 1% sorbitol;
21-4) 9% fenofibrate, 2.7% Lipoid E80, 19% sucrose, 4.5% sorbitol.

The formulations were spray dried in a commercially available spray dryer consisting of a chamber with inside diameter of 1.22 meters and a cylindrical height of 1.14 meters with a 60° conical bottom. Electrically heated air was used as the process gas admitted via a ceiling disperser. Each spray dried formulation was isolated initially as a dried powder that could be handled in a dry atmosphere without caking. A sample of spray dried powder prepared from formulation 21-2 that had an initial volume weighted average particle size of 1.7 microns in suspension before spray drying was reconstituted with mild sonication in simulated gastric fluid comprised of 2g NaCl and 7 ml of conc. HCl per liter and found to have an average particle size of 1.9 microns.

EXAMPLE 22

A mixture of Lipoid E80 and fenofibrate was homogeneously dispersed in 10 mM pH 8.0+/−0.2 aqueous phosphate buffer using a ProScientific 400 high shear mixer at 2,000 to 3,600 rpm at ambient temperature for 30 minutes, and then heated to 95° C., 15° C. above the melting point of the drug, during continuous high shear mixing at 2,500 to 4,000 rpm. The heated suspension was then batchwise homogenized in 3 to 10 batch volume cycles using a Microfluidizer M110Y operated at 3,400 to 3,600 psig while maintained at 85° C. to 99° C. to form a heated homogenate containing the drug. The heated homogenate was cooled by passage through a heat exchanger cooled by chilled water at 5° C. to 10° C. and the transiently stable cooled homogenate was further homogenized for 10 to 20 batch volume cycles using a Microfluidics M110 EH homogenizer operated at 18,000 psig (peak) while maintained below 13° C. The resulting cooled dispersion comprising small particles containing fenofibrate stabilized with phospholipid was then treated with bulking agents and excipients, mixed at ambient temperature, and then dried by spray drying. The following compositions (in wt %) were prepared by this method as powders having volume weighted diameter after reconstitution with mild sonication of 1 to 2 microns with smallest mode (vol. wt) unsonicated as 1.5 microns. The powders produced were easily flowing, easily transferable by pouring, and exhibited no sticking. Water content in these powders was found to be less than 2.5%, and in some cases such as 22-e, about 1%.

| Suspension No. | Fenofibrate | Lipoid E80 | Sucrose | Mannitol | Ac-Di-Sol | Cab-O-Sil (colloidal silica) |
|---|---|---|---|---|---|---|
| 22-a | 10.0 | 0.5 | 17.5 | | | |
| 22-b | 10.0 | 0.5 | 17.5 | | 1.8 | |
| 22-c | 10.0 | 0.5 | 17.5 | | | 0.5 |
| 22-d | 10.0 | 0.5 | 7 | | 3 | 0.5 |
| 22-e | 10.0 | 0.5 | | 7 | 3 | 0.5 |
| 22-f | 10.0 | 0.5 | 17.5 | | 1.8 | 0.5 |

Spray dried powders (100 parts) were blended with excipients Avicel-PH102 (18.5 parts), Ac-Di-Sol (3.95 parts), Cab-O-Sil (0.62 parts), and magnesium stearate (0.25 parts), processed into 1 mm granules or slugs by preliminary compression of the blend followed by crushing and seiving (USP Standard #14 sieve), blended with additional magnesium sterarate, and then compressed into tablet dosage forms. Hardness of the tablets produced in different batches ranged from 2 to 9 KPa either in an automatic tableting machine or by manual compression using a CMS-15 tablet press (Cadmach Machinaries). Disintegration times of these tablets were in the range of 3 to 10 minutes.

EXAMPLE 23

A two-treatment, two-period, two-sequence crossover clinical study was performed to evaluate the relative bioavailability of fenofibric acid in blood in 24 healthy volunteers after single dose oral administration of a tablet formulation of this invention comprising phospholipid stabilized microparticles of fenofibrate. The fenofibrate tablet dosage form consisted of 160 mg of fenofibrate and was derived from a dried lyophilized powder of this invention that contained between 0.1% and 3% moisture, and that was obtained from a suspension of microparticles consisting of 10% fenofibrate, 3% Lipoid E80, 10% sucrose, and 5% sorbitol, and that was further blended with sucrose at 5% by weight of the powder plus magnesium stearate at 0.2% plus colloidal silica at 0.2%. The bioavailability of fenofibric acid from the formulation of this invention was compared relative to that of commercially available micronized fenofibrate (Tricor®) in a 200 mg capsule. Each dosage form was taken orally within 5 minutes after a low-fat test meal. The study was divided into 2 study periods, study period 1 and study period 2. At each period a single fenofibrate dose was administered to the subjects. There was a washout period of 10 days between the 2 administrations. Plasma samples were collected before each administration and during the 96 hours following each administration. Assay of fenofibric acid was performed with a validated analytical method (HPLC-UV) on the plasma samples. Relevant pharmacokinetic parameters were determined to evaluate the bioavailability of fenofibric acid after 5 administration of each formulation, and the test formulation was compared to the reference formulation. The following results demonstrate bioequivalence between the formulation of this invention and the commercially available micronized fenofibrate (Tricor®) under low fat fed conditions.

| Parameters (N = 24) | 160 mg fenofibrate formulation of this invention fed with a low fat meal | | | 200 mg Tricor ® fed with a low fat meal | | |
|---|---|---|---|---|---|---|
| | Mean | +/−SD | CV (%) | Mean | +/−SD | CV (%) |
| $AUC_{0-t}$ = experimental area under the curve calculated according to the linear trapezoidal rule (ng · h/mL) | 137587.71 | 48203.28 | 35.03 | 149272.07 | 58621.21 | 39.27 |
| $AUC_{0-\infty}$ = area under the curve extrapolated to the infinite (ng · h/mL) | 140067.57 | 49380.22 | 35.25 | 152599.13 | 60529.39 | 39.67 |
| $C_{max}$ = maximal plasma concentration (ng/mL) | 11204.05 | 2507.73 | 22.38 | 10401.84 | 3039.54 | 29.22 |
| % extrapolated | 1.76 | 1.13 | 63.91 | 2.12 | 1.22 | 57.83 |
| $t_{max}$ = time to reach the maximal plasma concentration (hours, h) | 3.21 | 1.10 | 34.36 | 4.75 | 0.90 | 18.88 |
| $k_{el}$ = elimination rate constant ($h^{-1}$) | 0.0507 | 0.0220 | 43.51 | 0.0449 | 0.0177 | 39.37 |
| $t_{1/2\ el}$ = half-life of elimination (h) | 15.72 | 5.47 | 34.76 | 17.77 | 6.51 | 36.63 |
| $F_{rel}$ = relative bioavailability (%) | 94.05 | 12.36 | 13.14 | 100.00 | 0.00 | — |

| | $AUC_{0-t}$ | $AUC_{0-\infty}$ | $C_{max}$ |
|---|---|---|---|
| Ratio of LS Means calculated using least squares means (ln-transformed data) | 94.09% | 93.69% | 110.73% |
| Ratio of Arithmetic Means calculated using arithmetic means (untransformed data) | 92.17% | 91.79% | 107.71% |
| 90% Geometric Confidence Interval using ln-transformed data | 89.15% to 99.31% | 89.09% to 98.53% | 101.84% to 120.39% |
| Intra-Subject CV | 10.27% | 9.58% | 15.98% |

FIG. 3A is a graph of fenofibric acid mean plasma concentration (in ng/ml) versus time (in hours) found after oral administration of a 160 mg fenofibrate-containing tablet prepared according to this invention compared to that of a commercially available 200 mg Tricor® capsule each taken proximal to ingestion of a low fat meal (n=24). Data were derived from the present study described in this Example and demonstrate statistical bioequivalence between the two dosage forms under low fat fed conditions.

FIG. 3B is a graph of fenofibric acid Ln mean plasma concentration (in ng/ml) versus time (in hours) found after oral administration of a 160 mg fenofibrate-containing tablet prepared according to this invention compared to that of a commercially available 200 mg Tricor® capsule each taken proximal to ingestion of a low fat meal (n=24). Data were derived from the present study described in this Example and demonstrate statistical bioequivalence between the two dosage forms under low fat fed conditions.

EXAMPLE 24

Low Temperature Film coating of temperature and moisture sensitive tablets.

This example describes a method and composition comprising a protective coating utilizing a conventional coating technique to prevent or substantially retard tablet ingredient property changes such as morphological changes such as changes from amorphous to crystalline state induced by the effects of moisture and/or temperature on moisture and temperature sensitive tablets of this invention and to protect the tablets from becoming tacky post compression.

Tablets of a model formulation containing two temperature sensitive, lyophilized, milled, highly hygroscopic ingredients (sorbitol and sucrose, together with fenofibrate particles coated and stabilized with an egg phospholipid) were film coated at a scale of 800-1000 g using a conventional film coater equipped with a 15" perforated pan. A solvent based seal-coating system (Opagloss$^R$—shellac based polymer) and two aqueous based systems (Opadry$^R$ AMB—PVA based anti-moisture barrier and Opadry$^R$ II—HPMC based) were evaluated. Coating parameters such as suspension delivery rate, and inlet air temperature, volume and humidity were optimized to provide a film coat of uniform coverage and thickness. The quality of the coated tablets was evaluated for physical appearance, disintegration time and dissolution testing. Under film coating conditions prescribed by the supplier of the coating materials, the tablets immediately became tacky and agglomerated, a result attributed to the water in the coatings and to the temperature used. Agglomeration was prevented by seal coating the tablets at 25-30° C. using the non-aqueous Opagloss$^R$ system. Although smooth and non-agglomerated tablets were produced, the rate of dissolution of the seal coated tablets was significantly reduced even with 0.75% coating level. A series of aqueous coating trials resulted in satisfactory coated tablets being generated with both Opadry$^R$ AMB and Opadry$^R$ II using the following coating parameters: tablet bed temperature 20-25° C. (standard recommended by supplier was 40-45° C.); spray rate of 5-7 g/min (standard recommended by supplier was 10-15 g/min); inlet air dew point of −20° C. (standard recommended by supplier was 0-5° C.); and inlet air volume of 190 cfm (standard recommended by supplier was 90-100 cfm). It was observed that Opadry$^R$ II produced a uniform continuous film as compared with that produced using Opadry$^R$ AMB. This may be due to the higher minimum film forming temperature of Opadry$^R$ AMB. The Opadry$^R$ II coated tablets also provided an acceptable dissolution profile. Thus, a low-temperature aqueous film coating process was successfully developed using Opadry$^R$ II to improve the stability and physical acceptability of temperature and moisture sensitive products. The tablets exhibit dissolution profiles immediately after preparation and before coating that are unchanged immediately after coating and that are unchanged after one month at room temperature (about 20° C. to about 25° C.) at ambient humidity (from about 1% to about 70% relative humidity).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all -examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pharmaceutically acceptable oral dosage form of fenofibrate comprising fenofibrate present in an amount of from about 15% w/w to about 20% w/w of the dosage form;
phospholipid present in an amount of from about 1% w/w to about 8% w/w of the dosage form;
a buffer salt present in an amount of from about 0.1% w/w to about 0.5% w/w of the dosage forth;
one or more water-soluble bulking agent selected from maltodextrin and mannitol present in an amount of from about 7% w/w to about 20% w/w of the dosage form;
a cellulosic additive present in an amount of from about 3% w/w to about 8% w/w of the dosage form;
beads or crystals of a pharmaceutically acceptable water-soluble excipient support material present in an amount of from about 12% w/w to 16% w/w of the dosage form;

a polyvinylpyrrolidone or crospovidone present in an amount of from about 5% w/w to about 30% w/w of the dosage form;

croscarmellose sodium present in an amount of from about 1% w/w to about 6% w/w of the dosage form;

granular mannitol present in an amount of from about 3% w/w to about 30% w/w of the dosage form;

sodium dodecyl sulfate present in an amount of from about 1% w/w to about 4% of the dosage form;

silicon dioxide present in an amount of up to about 1% w/w of the dosage form; and a stearate present in an amount of up to about 1% w/w of the dosage form;

wherein the fenofibrate is in the form of microparticles coated with phospholipid, wherein the phospholipid coated microparticles are embedded in a matrix comprising the water-soluble bulking agent, phospholipid that is not coated on the microparticles, the buffer salt and the cellulosic additive, and wherein the surface of the beads or crystals of the pharmaceutically acceptable water-soluble excipient is coated with the matrix.

2. The dosage form of claim 1, wherein the fenofibrate is present in an amount of from about 18% w/w to about 19.5% w/w of the tablet.

3. The dosage form of claim 1, wherein the phospholipid is present in an amount of from about 2% w/w to about 6% w/w of the tablet.

4. The dosage form of claim 1, wherein the buffer salt is present in an amount of from 0.1% w/w to about 0.2% w/w of the tablet.

5. The dosage form of claim 1, wherein the bulking agent is maltodextrin present in an amount of from about 9% w/w to about 20% w/w of the tablet.

6. The dosage form of claim 1, wherein the bulking agent is mannitol present in an amount of from about 7% w/w to about 20% w/w of the tablet.

7. The dosage form of claim 1, wherein the cellulosic additive is a carboxymethylcellulose.

8. The dosage form of claim 1, wherein the cellulosic additive is sodium carboxymethylcellulose.

9. The dosage form of claim 1, wherein the cellulosic additive is present in an amount of from about 4% w/w to about 6% w/w of the tablet.

10. The dosage form of claim 1, wherein the water-soluble excipient support material present is present in an amount of from about 14% w/w to about 15% w/w of the tablet.

11. The dosage form of claim 1, wherein the polyvinylpyrrolidone or crospovidone is present in an amount of from about 6% w/w to about 26% w/w of the tablet.

12. The dosage form of claim 1, wherein the croscarmellose sodium is present in an amount of from about 2% w/w to about 5% w/w of the tablet.

13. The dosage form of claim 1, wherein the granular mannitol is present in an amount of from about 5% w/w to about 27% w/w of the tablet.

14. The dosage form of claim 1, wherein the sodium dodecyl sulfate is present in an amount of from about 2% w/w to about 3% w/w of the tablet.

15. The dosage form of claim 1, wherein the silicon dioxide is colloidal silicon dioxide present in an amount of from about 0.5% w/w to about 0.8% w/w of the tablet.

16. The dosage form of claim 1, wherein the stearate is magnesium stearate present in an amount of from about 0.2% w/w to about 0.5% w/w of the tablet.

17. A method of treating dislipidemia or dislipoproteinemia in a mammal comprising administering to said mammal a therapeutically effective oral dosage form of claim 1.

18. The method of claim 17, wherein the dosage form provides into the blood of said mammal in a fasted state a therapeutically effective amount of said fenofibrate that is at least 90% of the area under the curve (AUC) amount of the fenofibrate provided by the dosage form into the blood of said mammal in a fed state.

19. The dosage form of claim 1, wherein fenofibrate is present in an amount of from 45 to 51 mg per tablet dosage form.

20. The dosage form of claim 19, wherein fenofibrate is present in an amount of 48 mg per tablet dosage form.

21. The dosage form of claim 1, wherein fenofibrate is present in an amount of from 135 to 155 mg per tablet dosage form.

22. The dosage form of claim 21, wherein fenofibrate is present in an amount of 144 or 145 mg per tablet dosage form.

23. The dosage form of claim 1, wherein fenofibrate is present in an amount of from 120 to 130 mg per tablet dosage form.

24. The dosage form of claim 1, which is free of food effect.

25. A suspension of microparticles consisting of
9%-10% fenofibrate,
2.7%-3% Lipoid E80,
10%-19% sucrose, and
0%-5% sorbitol.

26. A powder comprising a lyophilized preparation of the suspension of claim 25, wherein said lyophilized preparation has a moisture content of between 0.1% and 0.3%.

27. A pharmaceutically acceptable tablet dosage form comprising the powder of claim 26, blended with 0.5% sucrose, 0.2% magnesium stearate, and 0.2% colloidal silica.

* * * * *

UNITED STATES PATENT AND TRADEMARK OFFICE
CERTIFICATE OF CORRECTION

| | | |
|---|---|---|
| PATENT NO. | : 8,586,094 B2 | Page 1 of 4 |
| APPLICATION NO. | : 10/428007 | |
| DATED | : November 19, 2013 | |
| INVENTOR(S) | : Michael Vachon et al. | |

It is certified that error appears in the above-identified patent and that said Letters Patent is hereby corrected as shown below:

In the Drawings:

In Figure 3A, sheet 3 of 3, side bar description, please correct the word "Connection" to read "Concentration".

In the Specification:

At column 1, line number 58, please correct the word "milling" to read "milled".

At column 2, line number 19, remove hyphen in "presence".

At column 2, line number 20, remove hyphen in "substance".

At column 2, line number 34, please delete "1000 calories" and replace it with "1000 kcal".

At column 3, line number 6, please correct the word "triglyercides" to read "triglycerides".

At column 3, line number 67, please correct the word "reduciton" to read "reduction".

At column 4, line number 40, please correct the word "reduciton" to read "reduction".

At column 5, line number 27, please correct "(EMDG)" to read "(DEGEE)".

At column 5, line number 47, please correct the words "poly(vinyl pyrrolidone)" with "polyvinyl pyrrolidone".

At column 6, line number 18, please correct the word "phospholipon" to "Phospholipon".

Signed and Sealed this
Twenty-fifth Day of February, 2014

Michelle K. Lee
*Deputy Director of the United States Patent and Trademark Office*

At column 6, line number 51, please delete the word "oxide" and replace it with the word "dioxide".

At column 7, line number 51, please delete the word "and" and replace it with "an".

At column 8, line number 39, please correct the hyphenated word "nanom-eters" to "nano-meters".

At column 8, line number 53, please correct the word "formulation" to read "formulations".

At column 9, line number 39, please delete the word "microparticles" and replace it with the word "particles".

At column 17, line number 16, please correct the hyphenated word "microflu-idized" to "micro-fluidized".

At column 17, line number 28, please correct the word "take" to "taken".

At column 18, line number 36, please correct the hyphenated word "admin-istration" to "adminis-tration".

At column 18, line number 55, please delete "1000 calories" and replace it with "1000 kcal".

At column 19, line number 36, remove hyphen in "diameter".

At column 20, line number 24, remove hyphen in "hypnotics".

At column 20, line number 29, please correct the word "antarrhythmics" to read "antiarrhythmics".

At column 22, line number 45, please correct the words "tetracane HI" to read "tetracaine HCl".

At column 23, line number 19, please correct the word "trimethylarnmonium" to "trimethylammonium".

At column 23, line number 25, remove hyphen in "substance".

At column 23, line number 26, please correct the hyphenated word "polax-omers" to read "poloxamers".

At column 24, line number 1, remove hyphen in "Lipids".

At column 27, line number 5, remove hyphen in "microfluidization".

CERTIFICATE OF CORRECTION (continued)
U.S. Pat. No. 8,586,094 B2

At column 31, line number 5, remove hyphen in "examined".

At column 31, line number 43, please correct the word "phospholipon" to "Phospholipon".

At column 31, line number 44, please correct the word "phospholipon" to "Phospholipon".

At column 31, line number 49, please correct the word "phospholipon" to "Phospholipon".

At column 31, line number 53, please correct the word "phospholipon" to "Phospholipon".

At column 31, line number 56, please correct the word "phospholipon" to "Phospholipon".

At column 31, line number 57, please correct the word "phospholipon" to "Phospholipon".

At column 32, line number 4, remove hyphen in "according".

At column 38, line number 61, please correct the word "comprise" to "comprises".

At column 39, line number 46, remove hyphen in "preferably".

At column 41, line number 57, remove hyphen in "energizing".

At column 42, line number 9, please correct the word "Microfluidix" to read "Microfluidics".

At column 43, line number 23, please correct the word "phospholipon" to "Phospholipon".

At column 43, line number 31, please correct the word "phospholipon" to "Phospholipon".

At column 43, line number 40, remove hyphen in "microfluidization".

At column 47, line number 35, please correct the hyphenated word "multi-player" to read "multi-layer".

At column 50, line number 64, please delete "1000 calories" and replace it with "1000 kcal".

At column 51, line number 10, please delete "1000 calories" and replace it with "1000 kcal".

At column 51, line number 23, please delete "1000 calories" and replace it with "1000 kcal".

At column 54, line number 13, please delete "W/w" and replace it with "w/w".

At column 54, line number 42, please correct the hyphenation of the word "carboxymeth-ylcellulose" to "carboxy-methylcellulose".

CERTIFICATE OF CORRECTION (continued)
U.S. Pat. No. 8,586,094 B2

At column 55, line number 40, please correct the hyphenated word "carboxym-ethylcellulose" to "carboxy-methylcellulose".

At column 56, line number 64, please correct the hyphenated word "Microflu-idics" to "Micro-fluidics".

At column 63, line number 33, please correct the hyphenated word "microf-luidized" to "micro-fluidized".

At column 63, line number 50, please correct "1000 Kcal" with "1000 kcal".